(12) United States Patent
Satoh et al.

(10) Patent No.: US 10,550,198 B2
(45) Date of Patent: *Feb. 4, 2020

(54) ANTI-GARP ANTIBODY

(71) Applicant: DAIICHI SANKYO COMPANY, LIMITED, Tokyo (JP)

(72) Inventors: Kazuki Satoh, Tokyo (JP); Kazuki Hirahara, Tokyo (JP); Ichiro Watanabe, Tokyo (JP); Masato Amano, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/044,196

(22) Filed: Jul. 24, 2018

(65) Prior Publication Data
US 2018/0327511 A1   Nov. 15, 2018

Related U.S. Application Data

(63) Continuation of application No. 15/761,045, filed as application No. PCT/JP2016/078067 on Sep. 23, 2016.

(30) Foreign Application Priority Data
Sep. 24, 2015 (JP) .................. 2015-187488

(51) Int. Cl.
| | |
|---|---|
| *C07K 16/28* | (2006.01) |
| *C07K 16/32* | (2006.01) |
| *A61K 39/395* | (2006.01) |
| *C12N 5/12* | (2006.01) |
| *C12N 5/10* | (2006.01) |
| *C12N 1/20* | (2006.01) |
| *C12N 15/02* | (2006.01) |
| *A61K 39/00* | (2006.01) |
| *A61P 35/00* | (2006.01) |

(52) U.S. Cl.
CPC ............ *C07K 16/32* (2013.01); *A61K 39/395* (2013.01); *C07K 16/28* (2013.01); *C12N 1/20* (2013.01); *C12N 5/10* (2013.01); *C12N 5/12* (2013.01); *C12N 15/02* (2013.01); *A61K 2039/505* (2013.01); *A61P 35/00* (2018.01); *C07K 2317/51* (2013.01); *C07K 2317/515* (2013.01); *C07K 2317/565* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,815,526 B2 | 8/2014 | Garaczi et al. | |
| 2009/0311183 A1 | 12/2009 | Devy et al. | |
| 2010/0178296 A1 | 7/2010 | Presta et al. | |
| 2010/0260668 A1 | 10/2010 | Ghayur et al. | |
| 2010/0317546 A1 | 12/2010 | Enzelberger et al. | |
| 2011/0086367 A1 | 4/2011 | Probst-Kepper et al. | |
| 2011/0287036 A1 | 11/2011 | Matsumura et al. | |
| 2012/0034215 A1 | 2/2012 | Kawaida et al. | |
| 2012/0117670 A1 | 5/2012 | Wirtz et al. | |
| 2012/0141486 A1 | 6/2012 | Watanabe et al. | |
| 2013/0156769 A1 | 6/2013 | Kufer et al. | |
| 2014/0004120 A1 | 1/2014 | Ohtsuka et al. | |

FOREIGN PATENT DOCUMENTS

| | | |
|---|---|---|
| JP | 2014-141434 A | 8/2014 |
| WO | WO-2006/089678 A2 | 8/2006 |
| WO | WO-2006/103639 A2 | 10/2006 |
| WO | WO-2012/147713 A1 | 11/2012 |
| WO | WO-2013/147212 A1 | 10/2013 |
| WO | WO-2013/154206 A1 | 10/2013 |
| WO | WO-2014/061277 A1 | 4/2014 |
| WO | WO-2015/015003 A1 | 2/2015 |
| WO | WO-2016/125017 A1 | 8/2016 |

OTHER PUBLICATIONS

Paul, Fundamental Immunology, 3rd Edition, 1993, pp. 292-295.*
Abel et al, Strong Impact of CD4 Foxp3 Regulatory T Cells and Limited Effect of T Cell-Derived IL-10 on Pathogen Clearance during Plasmodium yoeli Infection, The Journal of Immunology, 2012, vol. 188(11), pp. 5467-5477.
Bharat et al, Disseminated Ureaplasma infection as a cause of fatal hyperammonemia in humans, Science Translational Medicine, 2015, vol. 7 (284).
Dietze et al, Combining Regulatory T Cell Depletion and Inhibitory Receptor Blockade Improves Reactivation of Exhausted Virus-Specific CD8 T Cells and Efficiently Reduces Chronic Retroviral Loads, PLos Pathogens, 2013, vol. 9(12).
Govindaraj et al, Impaired Th1 immunity in ovarian cancer patients is mediated by TNFR2 Tregs within the tumor microenvironment, Clinical Immunology, 2013, vol. 149(1), pp. 97-110.
Hahn et al, Soluble GARP has potent antiinflammatory and immunomodulatory impact on human CD41 T cells, Blood, 2013, vol. 122(7), p. 1182-1191.

(Continued)

*Primary Examiner* — Hong Sang
(74) *Attorney, Agent, or Firm* — Foley & Lardner LLP

(57) ABSTRACT

The present invention relates to an antibody that binds to GARP and is useful as a therapeutic agent for a tumor, and a method for treating a tumor using the aforementioned antibody. It is an object of the present invention to provide an antibody, which inhibits the function of Treg in a tumor and is thereby used as a pharmaceutical product having therapeutic effects, a method for treating a tumor using the aforementioned antibody, and the like. An anti-GARP antibody that binds to GARP and exhibits inhibitory activity to Treg function and exhibits ADCC activity is obtained, and moreover a pharmaceutical composition for use in tumor therapy, comprising the aforementioned antibody, etc. is obtained.

48 Claims, 35 Drawing Sheets

Specification includes a Sequence Listing.

(56) References Cited

OTHER PUBLICATIONS

Kalathil et al, Higher Frequencies of GARP CTLA-4 Foxp3 T Regulatory Cells and Myeloid-Derived Suppressor Cells in Hepatocellular Carcinoma Patients Are Associated with Impaired T-Cell Functionality, Cancer Research, 2013, vol. 73.
Nishikawa et al, Regulatory T cells in tumor immunity, International Journal of Cancer, 2010, vo. 127(4), pp. 759-767.
Saison et al,Association between discordant immunological response to highly active anti-retroviral therapy, regulatory T cell percentage, immune cell activation and very low-level viraemia in HIV-infected patients, 2014, vol. 176(3), pp. 401-409.
Schuler et al, Phenotypic and functional characteristics of CD4 CD39 FOXP3 and CD4 CD39 FOXP3neg T-cell subsets in cancer patients, European Journal of Immunology, 2012, vol. 42(7), pp. 1876-1885.
Stockis et al, Comparison of stable human Treg and Th clones by transcriptional profiling, European Journal of Immunology, 2009, vol. 39(12), pp. 869-882.
Stockis et al,Membrane protein GARP is a receptor for latent TGF-b on the surface of activated human Treg, European Journal of Immunology, 2009, vol. 39(12), pp. 3315-3322.
Todryk et al, Correlation of Memory T Cell Responses against TRAP with Protection from Clinical Malaria, and CD4 CD25high T Cells with Susceptibility in Kenyans, PLos One, 2008, vol. 3(4).
Tran et al, GARP (LRRC32) is essential for the surface expression of latent TGF- on platelets and activated FOXP3 regulatory T cells, PNAS, 2009, vol. 106(32), pp. 13445-13450.
Wang et al, GARP regulates the bioavailability and activation of TGF, Molecular Biology of the Cell, 2012, vol. 23(6), pp. 1129-1139.
Wang et al,Identification of a Regulatory T Cell Specific Cell Surface Molecule that Mediates Suppressive Signals and Induces Foxp3 Expression, PLos One, 2008, vol. 3(7).
European Patent Office, "Communication with extended European Search Report," issued in connection with European Patent Application No. 16848676.9, dated May 13, 2019.
Cuende et al., "Monoclonal antibodies against GARP/TGF-β1 complexes inhibit the immunosuppressive activity of human regulatory T cells in vivo," Science Translational Medicine, vol. 7, Issue 284, 284ra56, Apr. 22, 2015, pp. 1-12.
Biolegend, "PE anti-human GARP (LRRC32) Antibody," revised on Nov. 30, 2012.
Enzo, Product Data Sheet: "LRRC32 monoclonal antibody (Plato-1)," ALX-804-867-C100, revised on Mar. 15, 2019.
Vermeersch et al., "Deletion of GARP on mouse regulatory T cells is not sufficient to inhibit the growth of transplanted tumors," Cellular Immunology, vol. 332, Jul. 30, 2018, pp. 129-133.
BD-Pharmingen, Technical Data Sheet for "PE Mouse anti-Human GARP," 2011.
Invitrogen, Product Details, Catalog No. 12-9882-42: "GARP Monoclonal Antibody (G14D9), PE, eBioscience™." Nov. 2018.
CO Office Action issued in the corresponding Colombian Patent Application Ser. No. NC2018/0003542, dated Jul. 4, 2019.
"Purified anti-mouse GARP (LRRC32) Antibody," 2013, BioLegend, (2 pages).

* cited by examiner

[Figure 1]
Amino acid sequence of Glycoprotein-A Repetitions Predominant (GARP) (SEQ ID NO: 1)

MRPQILLLLALLTLGLAAQHQDKVPCKMVDKKVSCQVLGLLQVPSVLPPDTETLDLSGNQLR
SILASPLGFYTALRHLDLSTNEISFLQPGAFQALTHLEHLSLAHNRLAMATALSAGGLGPLP
RVTSLDLSGNSLYSGLLERLLGEAPSLHTLSLAENSLTRLTRHTFRDMPALEQLDLHSNVLM
DIEDGAFEGLPRLTHLNLSRNSLTCISDFSLQQLRVLDLSCNSIEAFQTASQPQAEFQLTWL
DLRENKLLHFPDLAALPRLIYLNLSNNLIRLPTGPPQDSKGIHAPSEGWSALPLSAPSGNAS
GRPLSQLLNLDLSYNEIELIPDSFLEHLTSLCFLNLSRNCLRTFEARRLGSLPCLMLLDLSH
NALETLELGARALGSLRTLLLQGNALRDLPPYTFANLASLQRLNLQGNRVSPCGGPDEPGPS
GCVAFSGITSLRSLSLVDNEIELLRAGAFLHTPLTELDLSSNPGLEVATGALGGLEASLEVL
ALQGNGLMVLQVDLPCFICLKRLNLAENRLSHLPAWTQAVSLEVLDLRNNSFSLLPGSAMGG
LETSLRRLYLQGNPLSCCGNGWLAAQLHQGRVDVDATQDLICRFSSQEEVSLSHVRPEDCEK
GGLKNINLIIILTFILVSAILLTTLAACCCVRRQKFNQQYKA

[Figure 2]
Amino acid sequence of 105F antibody heavy chain (SEQ ID NO: 2)

EVQLLESGGGLVQPGGSLRLSCAASGFTFSDYYMSWIRQAPGKGLEWVSGVSWNGSRTHYAD
SVKGRFTISRDNSKNTLYLQMNSLRAEDTAVYYCARQRQLAEFDYWGQGTLVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFSCSVMHEALH
NHYTQKSLSLSPGK

[Figure 3]
Amino acid sequence of 105F antibody light chain (SEQ ID NO: 3)

QSVLTQPPSASGTPGQRVTISCTGSSSNIGAGYVVHWYQQLPGTAPKLLIYADTNRPSGVPD
RFSGSKSGTSASLAISGLRSEDEADYYCQSYDSSLRGWVFGGGTKLTVLGQPKAAPSVTLFP
PSSEELQANKATLVCLISDFYPGAVTVAWKADSSPVKAGVETTTPSKQSNNKYAASSYLSLT
PEQWKSHRSYSCQVTHEGSTVEKTVAPTECS

[Figure 4]
Amino acid sequence of 110F antibody heavy chain (SEQ ID NO: 4)

EVQLLESGGGLVQPGGSLRLSCAASGFTFSSYGMHWVRQAPGKGLEWVAGISWNSAITVYAD
SVKGRFTISRDNSKNTLYLQMNSLRAEDTAVYYCAKDAGGRYSGSYYFDYWGQGTLVTVSSA
STKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSVM
HEALHNHYTQKSLSLSPGK

[Figure 5]
Amino acid sequence of 110F antibody light chain (SEQ ID NO: 5)

QSVLTQPPSASGTPGQRVTISCTGSSSNIGAGYDVHWYQQLPGTAPKLLIYGNSNRPSGVPD
RFSGSKSGTSASLAISGLRSEDEADYYCQSYDRSLNWVFGGGTKLTVLGQPKAAPSVTLFPP
SSEELQANKATLVCLISDFYPGAVTVAWKADSSPVKAGVETTTPSKQSNNKYAASSYLSLTP
EQWKSHRSYSCQVTHEGSTVEKTVAPTECS

[Figure 6]
Nucleotide sequence of 105F antibody heavy chain (SEQ ID NO: 6)

GAGGTGCAGCTGTTGGAGTCTGGGGGAGGCTTGGTACAGCCTGGGGGGTCCCTGAGACTCTC
CTGTGCAGCCTCTGGATTCACCTTCAGTGACTACTACATGAGCTGGATCCGCCAGGCTCCAG
GCAAGGGGCTGGAGTGGGTATCGGGTGTTAGTTGGAATGGCAGTAGGACGCACTATGCAGAC
TCTGTGAAGGGCCGATTCACCATCTCCAGAGACAATTCCAAGAACACGCTGTATCTGCAAAT
GAACAGCCTGAGAGCCGAGGACACTGCCGTGTATTACTGTGCCAGACAGAGGCAGCTGGCTG
AATTTGACTACTGGGGCCAAGGTACCCTGGTCACCGTGAGCTCAGCCTCCACCAAGGGCCCA
AGCGTCTTCCCCCTGGCACCCTCCTCCAAGAGCACCTCTGGCGGCACAGCCGCCCTGGGCTG
CCTGGTCAAGGACTACTTCCCCGAACCCGTGACCGTGAGCTGGAACTCAGGCGCCCTGACCA
GCGGCGTGCACACCTTCCCCGCTGTCCTGCAGTCCTCAGGACTCTACTCCCTCAGCAGCGTG
GTGACCGTGCCCTCCAGCAGCTTGGGCACCCAGACCTACATCTGCAACGTGAATCACAAGCC
CAGCAACACCAAGGTGGACAAGAGAGTTGAGCCCAAATCTTGTGACAAAACTCACACATGCC
CACCCTGCCCAGCACCTGAACTCCTGGGGGGACCCTCAGTCTTCCTCTTCCCCCCAAAACCC
AAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGA
CAAAGCCCCGGGAGGAGCAGTACAACAGCACGTACCGGGTGGTCAGCGTCCTCACCGTCCTG
CACCAGGACTGGCTGAATGGCAAGGAGTACAAGTGCAAGGTCTCCAACAAAGCCCTCCCAGC
CCCCATCGAGAAAACCATCTCCAAAGCCAAAGGCCAGCCCCGGGAACCACAGGTGTACACCC
TGCCCCCATCCCGGGAGGAGATGACCAAGAACCAGGTCAGCCTGACCTGCCTGGTCAAAGGC
TTCTATCCCAGCGACATCGCCGTGGAGTGGGAGAGCAATGGCCAGCCCGAGAACAACTACAA
GACCACCCCTCCCGTGCTGGACTCCGACGGCTCCTTCTTCCTCTACAGCAAGCTCACCGTGG
ACAAGAGCAGGTGGCAGCAGGGCAACGTCTTCTCATGCTCCGTGATGCATGAGGCTCTGCAC
AACCACTACACCCAGAAGAGCCTCTCCCTGTCTCCGGCAAA

[Figure 7]
Nucleotide sequence of 105F antibody light chain (SEQ ID NO: 7)

CAGTCTGTGCTGACTCAGCCACCCTCAGCGTCTGGGACCCCCGGGCAGAGGGTCACCATCTC
CTGCACTGGGAGCAGCTCCAACATTGGGGCGGGTTATGTTGTACATTGGTATCAGCAGCTCC
CAGGAACGGCCCCCAAACTCCTCATCTATGCTGACACCAATCGGCCCTCAGGGGTCCCTGAC
CGATTCTCTGGCTCCAAGTCTGGCACCTCAGCCTCCTGGCCATCAGTGGGCTCCGGTCCGA
GGATGAGGCTGATTATTACTGCCAGTCCTATGACAGCAGCCTGAGAGGTTGGGTGTTCGGCG
GAGGAACCAAGCTGACGGTCCTAGGTCAGCCTAAGGCTGCCCCTAGCGTGACCCTGTTCCCT
CCTTCCAGCGAGGAGCTTCAAGCTAACAAGGCCACCCTGGTGTGTCTTATCTCTGACTTCTA
CCCTGGCGCTGTGACCGTGGCCTGGAAGGCTGACAGCTCCCCTGTGAAGGCCGGAGTGGAGA
CCACCACACCTAGCAAGCAGTCTAACAACAAGTACGCTGCCAGCTCCTACCTGAGCCTTACC
CCTGAGCAGTGGAAGTCTCACAGAAGCTACTCCTGTCAAGTGACCCACGAGGGCAGCACCGT
GGAGAAGACCGTGGCTCCTACCGAGTGTTCC

[Figure 8]
Nucleotide sequence of 110F antibody heavy chain (SEQ ID NO: 8)

GAGGTGCAGCTGTTGGAGTCTGGGGGAGGCTTGGTACAGCCTGGGGGGTCCCTGAGACTCTC
CTGTGCAGCCTCTGGATTCACCTTCAGTAGCTATGGCATGCACTGGGTCCGCCAGGCTCCAG
GCAAGGGGCTGGAGTGGGTCGCCGGAATTAGTTGGAACAGTGCCATCACAGTCTATGCGGAC
TCTGTGAAGGGCCGGTTCACCATCTCCAGAGACAATTCCAAGAACACGCTGTATCTGCAAAT
GAACAGCCTGAGAGCCGAGGACACTGCCGTGTATTACTGTGCAAAAGATGCCGGGGGCCGGT
ATAGTGGGAGCTACTACTTTGACTACTGGGGCCAAGGTACCCTGGTCACCGTGAGCTCAGCC
TCCACCAAGGGCCCAAGCGTCTTCCCCCTGGCACCCTCCTCCAAGAGCACCTCTGGCGGCAC
AGCCGCCCTGGGCTGCCTGGTCAAGGACTACTTCCCCGAACCCGTGACCGTGAGCTGGAACT
CAGGCGCCCTGACCAGCGGCGTGCACACCTTCCCCGCTGTCCTGCAGTCCTCAGGACTCTAC
TCCCTCAGCAGCGTGGTGACCGTGCCCTCCAGCAGCTTGGGCACCCAGACCTACATCTGCAA
CGTGAATCACAAGCCCAGCAACACCAAGGTGGACAAGAGAGTTGAGCCCAAATCTTGTGACA
AAACTCACACATGCCCACCCTGCCCAGCACCTGAACTCCTGGGGGGACCCTCAGTCTTCCTC
TTCCCCCCAAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGGCGTGGAGG
TGCATAATGCCAAGACAAAGCCCCGGGAGGAGCAGTACAACAGCACGTACCGGGTGGTCAGC
GTCCTCACCGTCCTGCACCAGGACTGGCTGAATGGCAAGGAGTACAAGTGCAAGGTCTCCAA
CAAAGCCCTCCCAGCCCCCATCGAGAAAACCATCTCCAAAGCCAAAGGCCAGCCCCGGGAAC
CACAGGTGTACACCCTGCCCCCATCCCGGGAGGAGATGACCAAGAACCAGGTCAGCCTGACC
TGCCTGGTCAAAGGCTTCTATCCCAGCGACATCGCCGTGGAGTGGGAGAGCAATGGCCAGCC
CGAGAACAACTACAAGACCACCCCTCCCGTGCTGGACTCCGACGGCTCCTTCTTCCTCTACA
GCAAGCTCACCGTGGACAAGAGCAGGTGGCAGCAGGGCAACGTCTTCTCATGCTCCGTGATG
CATGAGGCTCTGCACAACCACTACACCCAGAAGAGCCTCTCCCTGTCTCCGGCAAA

[Figure 9]
Nucleotide sequence of 110F antibody light chain (SEQ ID NO: 9)

CAGTCTGTGCTGACTCAGCCACCCTCAGCGTCTGGGACCCCCGGGCAGAGGGTCACCATCTC
CTGCACTGGGAGCAGCTCCAACATCGGGGCAGGTTATGATGTACACTGGTATCAGCAGCTCC
CAGGAACGGCCCCCAAACTCCTCATCTATGGTAACAGCAATCGGCCCTCAGGGGTCCCTGAC
CGATTCTCTGGCTCCAAGTCTGGCACCTCAGCCTCCTGGCCATCAGTGGGCTCCGGTCCGA
GGATGAGGCTGATTATTACTGCCAGTCCTATGACAGAAGCCTGAATTGGGTGTTCGGCGGAG
GAACCAAGCTGACGGTCCTAGGTCAGCCTAAGGCTGCCCCTAGCGTGACCCTGTTCCCTCCT
TCCAGCGAGGAGCTTCAAGCTAACAAGGCCACCCTGGTGTGTCTTATCTCTGACTTCTACCC
TGGCGCTGTGACCGTGGCCTGGAAGGCTGACAGCTCCCTGTGAAGGCCGGAGTGGAGACCA
CCACACCTAGCAAGCAGTCTAACAACAAGTACGCTGCCAGCTCCTACCTGAGCCTTACCCCT
GAGCAGTGGAAGTCTCACAGAAGCTACTCCTGTCAAGTGACCCACGAGGGCAGCACCGTGGA
GAAGACCGTGGCTCCTACCGAGTGTTCC

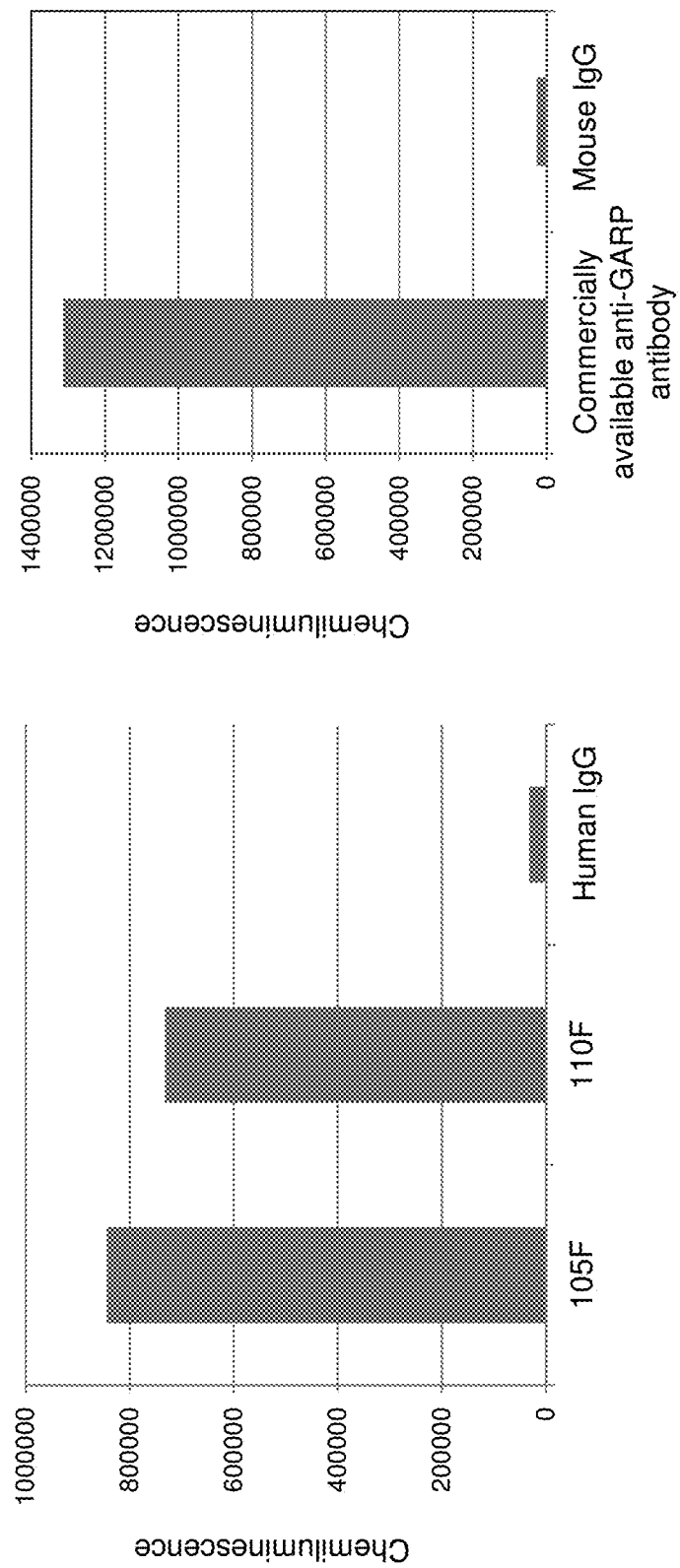
[Figure 10]

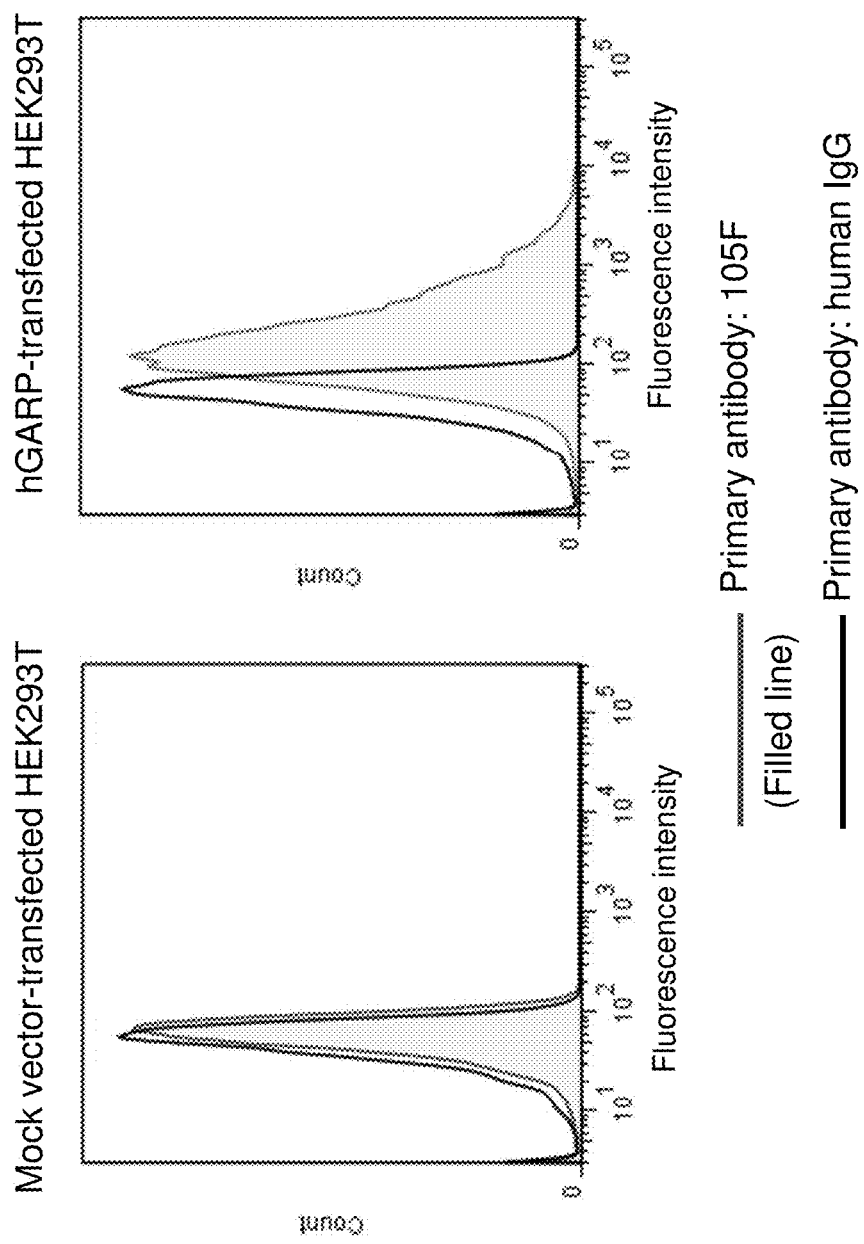
[Figure 11]

[Figure 12]
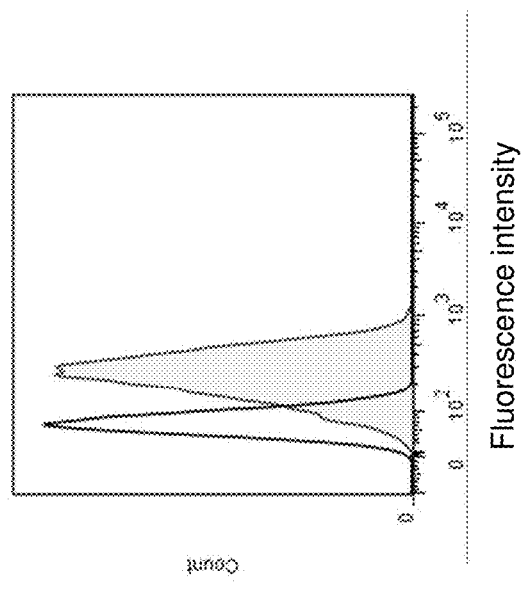

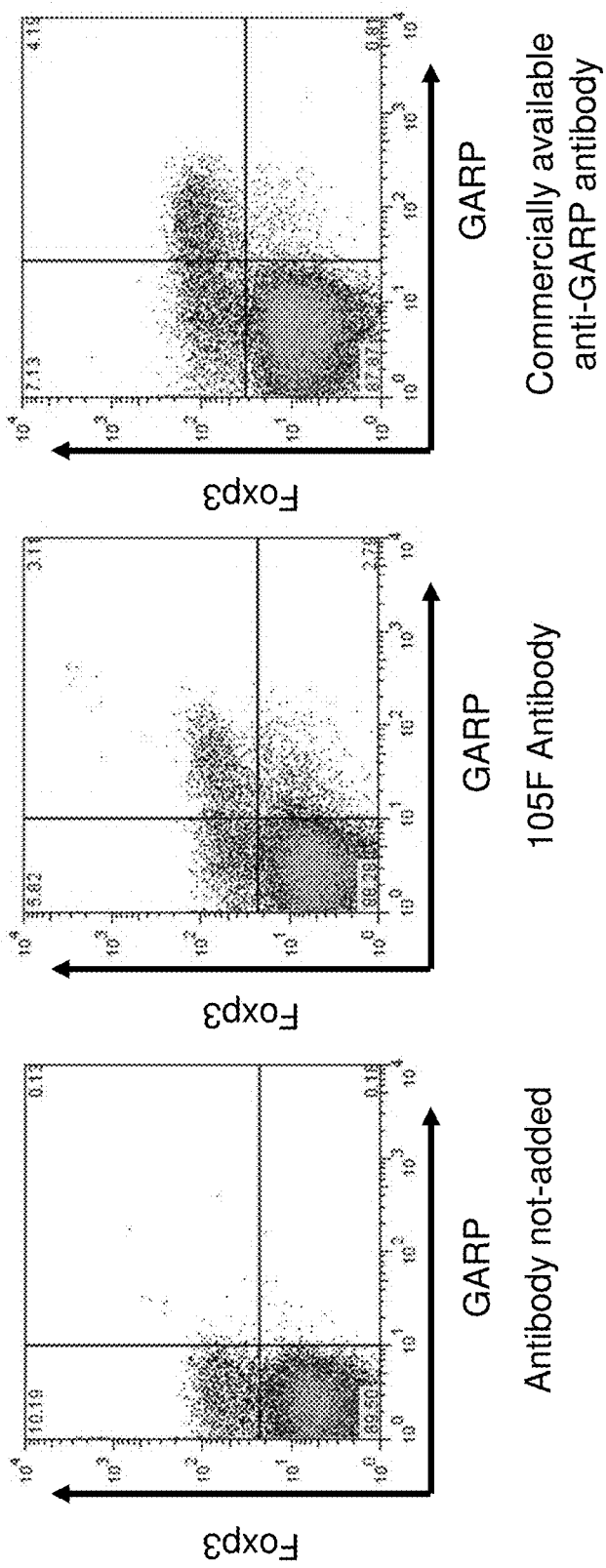
[Figure 13]

[Figure 14]
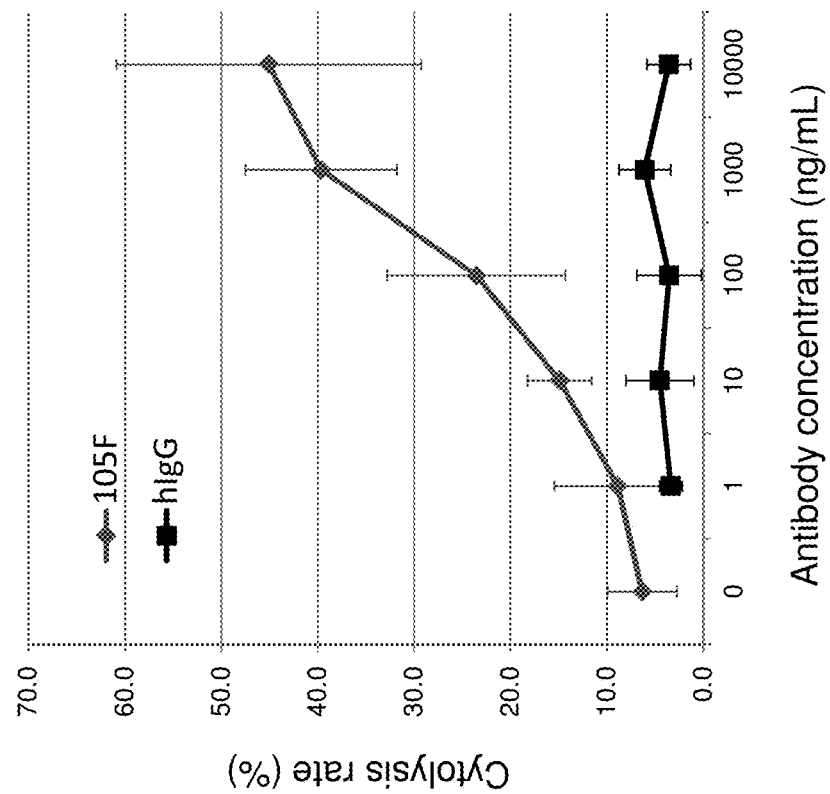

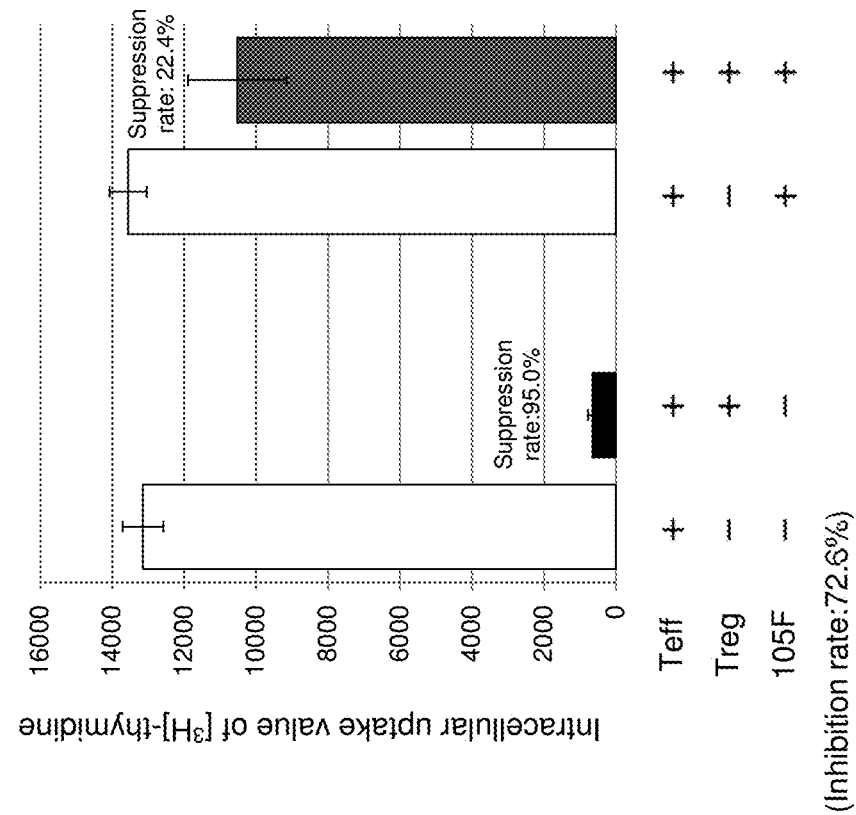
[Figure 15]

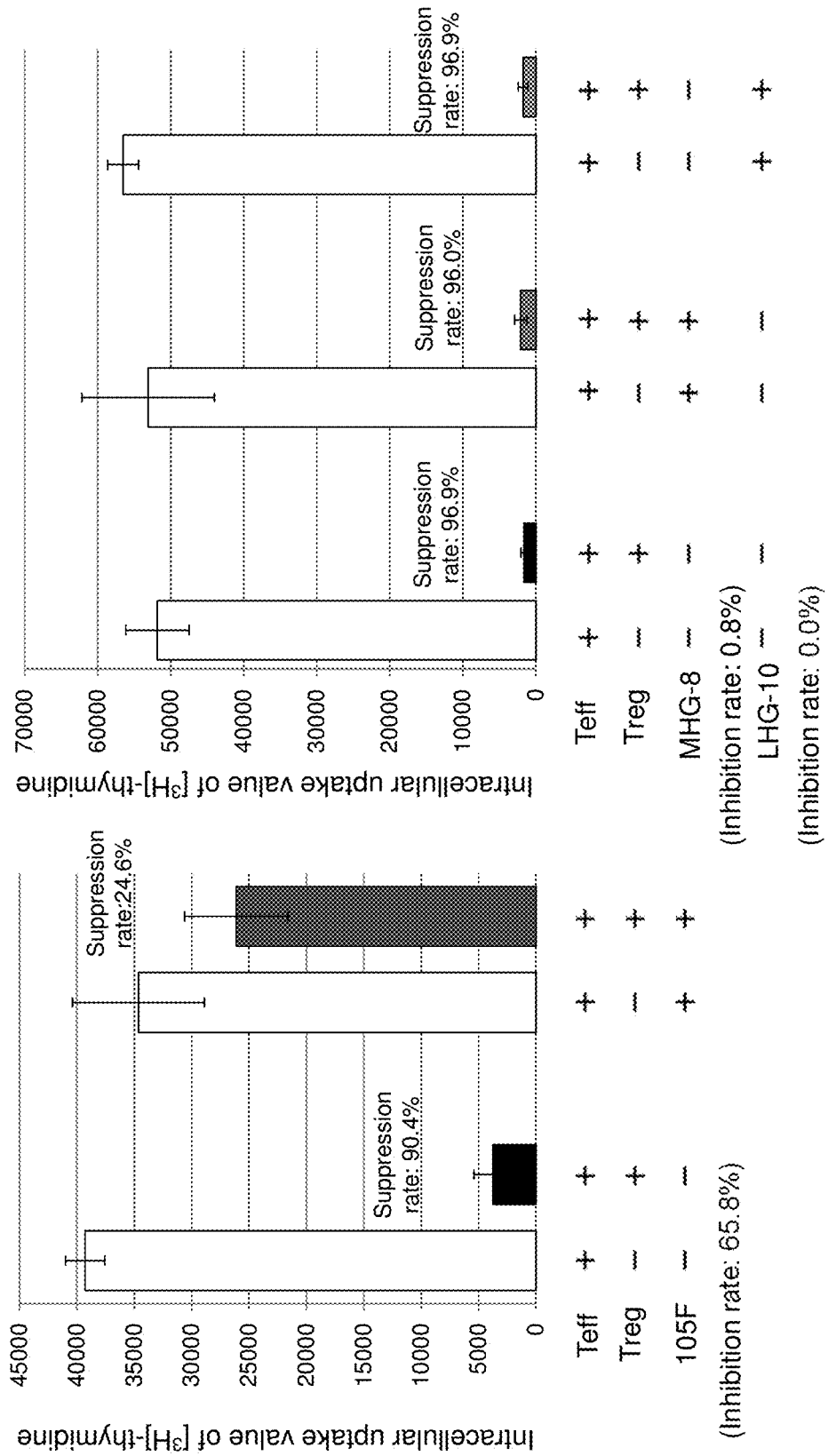
[Figure 16]

[Figure 17]
Amino acid sequence of c151D antibody heavy chain (SEQ ID NO: 25)

MKHLWFFLLLVAAPRWVLSEVQLVESGGGLVQPGRSKKLSCSASGFTFSNYYMAWVRQAPTQ
GLEWVASIGTVGGNTYYRDSVKGRFTISRDDAKSTLYLQMDSLRSEDTATYYCAREDYGGFP
HWGQGVMVTVSSASTKGPSVFPLAPSSKSTSGGTAALGCLVKDYFPEPVTVSWNSGALTSGV
HTFPAVLQSSGLYSLSSVVTVPSSSLGTQTICNVNHKPSNTKVDKRVEPKSCDKTHTCPPCP
APELLGGPSVFLFPPKPDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGPREPQVYTLPPSRE
EMTKNQVSLTCLVKGFYPSDIAVEWESNGQPENNYTTPPVLDSDGSFFLYSKLTVDKSRWQQ
GNVFSCSVMHEALHNHYTQKSLLSPGK

[Figure 18]
Amino acid sequence of c151D antibody light chain (SEQ ID NO: 27)

SEQ ID NO: 27: amino acid sequence of human chimeric antibody
c151D light chain
MVLQTQVFISLLLWISGAYGNIVMTQSPTSMFISVGDRVTMNCKASQNVGTNVDWYQQKTGQ
SPKLLIYGASNRYTGVPDRFTGSGSGTDFTLTISNMQAEDLAVYDCLQYKYNPYTFGTGTKL
ELNRAVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

[Figure 19]
Amino acid sequence of c198D antibody heavy chain (SEQ ID NO: 29)

MKHLWFFLLLVAAPRWVLSQVQLRESGPGLVQPSQTLSLTCTVSGFSLTSFHVSWVRQPPEK
GLEWIATISSGGGTYYNSALKSRLSISRDTSKSQVFLKMSTLQTEDTAMYFCARISGWGHYY
VMDVWGQGASVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTHTC
PPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK

[Figure 20]
Amino acid sequence of c198D antibody light chain (SEQ ID NO: 31)

MVLQTQVFISLLLWISGAYGDIQMTQSPASLSGSLGETVTIQCQASEDIYSGLAWYQQKPGK
SPQLLIYGAGSLQDGVPSRFSGGGSGTHYSLKISSMQTEDEGVYFCQQGLKFPLTFGSGTKL
EIKRAVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

[Figure 21]
Amino acid sequence of h151D-H1 heavy chain (SEQ ID NO: 33)

MKHLWFFLLLVAAPRWVLSEVQLVESGGGLVQPGGSLRLSCAASGFTFSNYYMAWVRQAPGK
GLEWVSSIGTVGGNTYYADSVKGRFTISRDDSKNTLYLQMNSLRAEDTAVYYCAREDYGGFP
HWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK

[Figure 22]
Amino acid sequence of h151D-L1 light chain (SEQ ID NO: 37)

MVLQTQVFISLLLWISGAYGNIVMTQSPDSLAVSLGERATINCKASQNVGTNVDWYQQKPGQ
SPKLLIYGASNRYTGVPDRFSGSGSGTDFTLTISSLQAEDVAVYDCLQYKYNPYTFGQGTKV
EIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

[Figure 23]
Amino acid sequence of h151D-H4 heavy chain (SEQ ID NO: 35)

MKHLWFFLLLVAAPRWVLSEVQLVESGGGLVQPGGSLRLSCAASGFTFSNYYMAWVRQAPGK
GLEWVASIGTVGGNTYYRDSVKGRFTISRDDSKSTLYLQMNSLRAEDTAVYYCAREDYGGFP
HWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK

[Figure 24]
Amino acid sequence of h151D-L4 light chain (SEQ ID NO: 39)

MVLQTQVFISLLLWISGAYGNIVMTQSPSSLSASVGDRVTINCKASQNVGTNVDWYQQKPGK
SPKLLIYGASNRYTGVPDRFSGSGSGTDFTLTISSLQPEDFATYDCLQYKYNPYTFGQGTKV
EIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

[Figure 25]
Amino acid sequence of h198D-H3 heavy chain (SEQ ID NO: 41)

MKHLWFFLLLVAAPRWVLSEVQLVESGGGLVKPSQTLSLTCTVSGFSLTSFHVSWVRQPPGK
GLEWIATISSGGGTYYNPSLKSRVTISRDTSKNQVSLKLSSVTAADTAVYYCARISGWGHYY
VMDVWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTHTC
PPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK

[Figure 26]
Amino acid sequence of h198D-L4 light chain (SEQ ID NO: 43)

MVLQTQVFISLLLWISGAYGDIQMTQSPSSLSASVGDRVTITCQASEDIYSGLAWYQQKPGK
SPKLLIYGAGSLQDGVPSRFSGSGSGTHYTLTISSLQPEDFATYFCQQGLKFPLTFGQGTKV
EIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

[Figure 27]
Nucleotide sequence of c151D antibody heavy chain (SEQ ID NO: 24)

ATGAAACACCTGTGGTTCTTCCTCCTGCTGGTGGCAGCTCCCAGATGGGTGCTGAGCGAGGT
GCAGCTGGTGGAGTCTGGGGGAGGCTTAGTGCAGCCTGGAAGGTCCAAGAAACTCTCCTGTT
CAGCCTCAGGATTCACTTTCAGTAACTATTACATGGCCTGGGTCCGCCAGGCTCCAACGCAG
GGTCTGGAGTGGGTCGCATCCATTGGTACTGTTGGTGGTAACACTTACTATCGAGACTCCGT
GAAGGGCCGATTCACTATCTCCAGAGATGATGCAAAAGCACCCTATACCTGCAAATGGACA
GTCTGAGGTCTGAGGACACGGCCACTTATTACTGTGCAAGAGAGGATTACGGAGGGTTTCCC
CACTGGGGCCAAGGAGTCATGGTCACAGTCAGCTCAGCCTCCACCAAGGGCCCAAGCGTCTT
CCCCCTGGCACCCTCCTCCAAGAGCACCTCTGGCGGCACAGCCGCCCTGGGCTGCCTGGTCA
AGGACTACTTCCCCGAACCCGTGACCGTGAGCTGGAACTCAGGCGCCCTGACCAGCGGCGTG
CACACCTTCCCCGCTGTCCTGCAGTCCTCAGGACTCTACTCCCTCAGCAGCGTGGTGACCGT
GCCCTCCAGCAGCTTGGGCACCCAGACCTACATCTGCAACGTGAATCACAAGCCCAGCAACA
CCAAGGTGGACAAGAGAGTTGAGCCCAAATCTTGTGACAAAACTCACACATGCCCACCCTGC
CCAGCACCTGAACTCCTGGGGGGACCCTCAGTCTTCCTCTTCCCCCCAAAACCCAAGGACAC
CCTCATGATCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGACAAAGCCC
CGGGAGGAGCAGTACAACAGCACGTACCGGGTGGTCAGCGTCCTCACCGTCCTGCACCAGGA
CTGGCTGAATGGCAAGGAGTACAAGTGCAAGGTCTCCAACAAAGCCCTCCCAGCCCCCATCG
AGAAAACCATCTCCAAAGCCAAAGGCCAGCCCCGGGAACCACAGGTGTACACCCTGCCCCCA
TCCCGGGAGGAGATGACCAAGAACCAGGTCAGCCTGACCTGCCTGGTCAAAGGCTTCTATCC
CAGCGACATCGCCGTGGAGTGGGAGAGCAATGGCCAGCCCGAGAACAACTACAAGACCACCC
CTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTA
CACCCAGAAGAGCCTCTCCCTGTCTCCCGGCAAA

[Figure 28]
Nucleotide sequence of c151D antibody light chain (SEQ ID NO: 26)

ATGGTGCTGCAGACCCAGGTGTTCATCTCCCTGCTGCTGTGGATCTCCGGCGCGTACGGCAA
TATTGTGATGACTCAGTCTCCCACATCCATGTTCATATCAGTCGGAGACAGGGTCACCATGA
ACTGTAAGGCCAGTCAGAATGTGGGAACTAATGTAGACTGGTACCAGCAGAAAACAGGGCAG
TCTCCTAAACTGCTTATCTATGGGCGTCCAACCGCTACACTGGAGTCCCTGATCGCTTCAC
AGGCAGTGGATCTGGAACAGATTTCACTCTCACCATCAGCAACATGCAGGCTGAAGACCTGG
CTGTTTATGACTGTCTACAGTATAAGTACAATCCATACACGTTTGGAACTGGGACCAAGCTG
GAACTGAACCGGGCTGTGGCCGCCCCTCCGTGTTCATCTTCCCCCCCTCCGACGAGCAGCT
GAAGTCCGGCACCGCCTCCGTGGTGTGCCTGCTGAATAACTTCTACCCCAGAGAGGCCAAGG
TGCAGTGGAAGGTGGACAACGCCCTGCAGTCCGGGAACTCCCAGGAGAGCGTGACCGAGCAG
GACAGCAAGGACAGCACCTACAGCCTGAGCAGCACCCTGACCCTGAGCAAAGCCGACTACGA
GAAGCACAAGGTGTACGCCTGCGAGGTGACCCACCAGGGCCTGAGCTCCCCGTCACCAAGA
GCTTCAACAGGGGGGAGTGT

[Figure 29]
Nucleotide sequence of c198D antibody heavy chain (SEQ ID NO: 28)

ATGAAACACCTGTGGTTCTTCCTCCTGCTGGTGGCAGCTCCCAGATGGGTGCTGAGCCAGGT
GCAGCTGAGGGAGTCAGGACCTGGTCTGGTGCAGCCCTCACAGACCCTGTCCCTCACCTGCA
CTGTCTCTGGGTTCTCACTAACCAGCTTTCATGTAAGCTGGGTTCGCCAGCCTCCAGAGAAG
GGTCTGGAGTGGATTGCAACAATTTCAAGTGGTGGAGGTACATATTATAATTCAGCTCTCAA
ATCCCGACTGAGCATCAGCAGGGACACCTCCAAGAGCCAAGTTTTCTTAAAGATGAGCACTC
TGCAAACTGAAGACACAGCCATGTACTTCTGTGCCCGGATTTCGGGCTGGGGCCATTACTAT
GTTATGGATGTCTGGGGTCAAGGAGCTTCAGTCACTGTCAGCTCAGCCTCCACCAAGGGCCC
AAGCGTCTTCCCCCTGGCACCCTCCTCAAGAGCACCTCTGGCGGCACAGCCGCCCTGGGCT
GCCTGGTCAAGGACTACTTCCCCGAACCCGTGACCGTGAGCTGGAACTCAGGCGCCCTGACC
AGCGGCGTGCACACCTTCCCCGCTGTCCTGCAGTCCTCAGGACTCTACTCCCTCAGCAGCGT
GGTGACCGTGCCCTCCAGCAGCTTGGGCACCCAGACCTACATCTGCAACGTGAATCACAAGC
CCAGCAACACCAAGGTGGACAAGAGAGTTGAGCCCAAATCTTGTGACAAAACTCACACATGC
CCACCCTGCCCAGCACCTGAACTCCTGGGGGGACCCTCAGTCTTCCTCTTCCCCCCAAAACC
CAAGGACACCCTCATGATCTCCCGGACCCCTGAGGTCACATGCGTGGTGGTGGACGTGAGCC
ACGAAGACCCTGAGGTCAAGTTCAACTGGTACGTGGACGGCGTGGAGGTGCATAATGCCAAG
ACAAAGCCCCGGGAGGAGCAGTACAACAGCACGTACCGGGTGGTCAGCGTCCTCACCGTCCT
GCACCAGGACTGGCTGAATGGCAAGGAGTACAAGTGCAAGGTCTCCAACAAAGCCCTCCCAG
CCCCCATCGAGAAAACCATCTCCAAAGCCAAAGGCCAGCCCCGGGAACCACAGGTGTACACC
CTGCCCCCATCCCGGGAGGAGATGACCAAGAACCAGGTCAGCCTGACCTGCCTGGTCAAAGG
CTTCTATCCCAGCGACATCGCCGTGGAGTGGGAGAGCAATGGCCAGCCCGAGAACAACTACA
AGACCACCCCTCCCGTGCTGGACTCCGACGGCTCCTTCTTCCTCTACAGCAAGCTCACCGTG
GACAAGAGCAGGTGGCAGCAGGGCAACGTCTTCTCATGCTCCGTGATGCATGAGGCTCTGCA
CAACCACTACACCCAGAAGAGCCTCTCCCTGTCTCCGGCAAA

[Figure 30]
Nucleotide sequence of c198D antibody light chain (SEQ ID NO: 30)

ATGGTGCTGCAGACCCAGGTGTTCATCTCCCTGCTGCTGTGGATCTCCGGCGCGTACGGCGA
CATCCAGATGACACAGTCTCCAGCTTCCCTGTCTGGATCTCTGGGAGAAACTGTCACCATCC
AATGTCAAGCAAGTGAGGACATTTACAGTGGTTTAGCGTGGTATCAGCAGAAGCCAGGGAAA
TCTCCTCAGCTCCTGATCTATGGTGCAGGTAGCTTACAAGACGGCGTCCCATCACGATTCAG
TGGCGGTGGATCTGGCACACATTATTCTCTCAAGATCAGCAGCATGCAAACTGAAGATGAAG
GGGTTTATTTCTGTCAACAGGGTTTAAAGTTTCCGCTCACGTTCGGTTCTGGGACCAAGCTG
GAGATCAAACGGGCTGTGGCCGCCCCTCCGTGTTCATCTTCCCCCCTCCGACGAGCAGCT
GAAGTCCGGCACCGCCTCCGTGGTGTGCCTGCTGAATAACTTCTACCCCAGAGAGGCCAAGG
TGCAGTGGAAGGTGGACAACGCCCTGCAGTCCGGGAACTCCCAGGAGAGCGTGACCGAGCAG
GACAGCAAGGACAGCACCTACAGCCTGAGCAGCACCCTGACCCTGAGCAAAGCCGACTACGA
GAAGCACAAGGTGTACGCCTGCGAGGTGACCCACCAGGGCCTGAGCTCCCCGTCACCAAGA
GCTTCAACAGGGGGGAGTGT

[Figure 31]
Nucleotide sequence of h151D-H1 heavy chain (SEQ ID NO: 32)

ATGAAGCACCTGTGGTTCTTTCTGCTGCTGGTGGCCGCTCCCAGATGGGTGCTGTCTGAAGT
GCAGCTGGTGGAATCCGGCGGAGGCCTGGTGCAGCCTGGCGGATCTCTGAGACTGTCTTGTG
CCGCCTCCGGCTTCACCTTCTCCAACTACTACATGGCCTGGGTGCGACAGGCCCCTGGCAAG
GGACTGGAATGGGTGTCCTCTATCGGCACCGTGGGCGGCAACACCTACTACGCCGATTCTGT
GAAGGGCCGGTTCACCATCTCCCGGGACGACTCCAAGAACACCCTGTACCTGCAGATGAACT
CCCTGCGGGCCGAGGACACCGCCGTGTACTACTGTGCCAGAGAGGACTACGGCGGCTTCCCT
CATTGGGGCCAGGGCACACTCGTGACCGTGTCCTCTGCTTCCACCAAGGGCCCCTCCGTGTT
TCCTCTGGCCCCTTCCAGCAAGTCCACCTCTGGCGGAACAGCCGCTCTGGGCTGCCTCGTGA
AGGACTACTTCCCCGAGCCCGTGACAGTGTCTTGGAACTCTGGCGCCCTGACCTCCGGCGTG
CACACCTTTCCAGCTGTGCTGCAGTCCTCCGGCCTGTACTCCCTGTCCTCCGTCGTGACTGT
GCCCTCCAGCTCTCTGGGCACCCAGACCTACATCTGCAACGTGAACCACAAGCCCTCCAACA
CCAAGGTGGACAAGCGGGTGGAACCCAAGTCCTGCGACAAGACCCACACCTGTCCCCCTTGT
CCTGCCCCTGAACTGCTGGGCGGACCTTCCGTGTTCCTGTTCCCCCCAAAGCCTAAGGACAC
CCTGATGATCTCCCGGACCCCCGAAGTGACCTGCGTGGTGGTGGATGTGTCCCACGAGGACC
CTGAAGTGAAGTTCAATTGGTACGTGGACGGCGTGGAAGTGCACAACGCCAAGACCAAGCCT
AGAGAGGAACAGTACAACTCCACCTACCGGGTGGTGTCCGTGCTGACCGTGCTGCATCAGGA
CTGGCTGAACGGCAAAGAGTACAAGTGCAAGGTGTCCAACAAGGCCCTGCCTGCCCCCATCG
AAAAGACCATCTCCAAGGCCAAGGGCCAGCCCCGGGAACCCCAGGTGTACACACTGCCCCCT
AGCCGGGAAGAGATGACCAAGAACCAGGTGTCCCTGACCTGTCTCGTGAAAGGCTTCTACCC
CTCCGATATCGCCGTGGAATGGGAGAGCAACGGCCAGCCCGAGAACAACTACAAGACCACCC
CCCCTGTGCTGGACTCCGACGGCTCATTCTTCCTGTACAGCAAGCTGACAGTGGACAAGTCC
CGGTGGCAGCAGGGCAACGTGTTCTCCTGCTCCGTGATGCACGAGGCCCTGCACAACCACTA
CACCCAGAAGTCCCTGTCCCTGAGCCCCGGCAAA

[Figure 32]
Nucleotide sequence of h151D-L1 light chain (SEQ ID NO: 36)

ATGGTGCTGCAGACCCAGGTGTTCATCTCCCTGCTGCTGTGGATCTCCGGCGCCTACGGCAA
CATCGTGATGACCCAGTCCCCCGACTCCCTGGCTGTGTCTCTGGGCGAGAGAGCCACCATCA
ACTGCAAGGCCTCCCAGAACGTGGGCACCAACGTGGACTGGTATCAGCAGAAGCCCGGCCAG
TCCCCTAAGCTGCTGATCTACGGCGCCAGCAACCGGTACACCGGCGTGCCCGATAGATTCTC
CGGCTCTGGCTCTGGCACCGACTTTACCCTGACAATCAGCTCTCTGCAGGCCGAGGACGTGG
CCGTGTACGACTGCCTGCAGTACAAGTACAACCCCTACACCTTCGGCCAGGGCACAAAGGTG
GAAATCAAGCGGACCGTGGCCGCTCCCTCCGTGTTTATCTTCCCACCCTCCGACGAGCAGCT
GAAGTCCGGCACAGCTTCCGTCGTGTGCCTGCTGAACAACTTCTACCCCGCGAGGCCAAGG
TGCAGTGGAAGGTGGACAACGCCCTGCAGTCCGGCAACTCCCAGGAATCCGTGACCGAGCAG
GACTCCAAGGACAGCACCTACTCCCTGTCCTCCACCCTGACCCTGTCCAAGGCCGACTACGA
GAAGCACAAGGTGTACGCCTGCGAAGTGACCCACCAGGGCCTGTCTAGCCCCGTGACCAAGT
CTTTCAACCGGGGCGAGTGC

[Figure 33]
Nucleotide sequence of h151D-H4 heavy chain (SEQ ID NO: 34)

ATGAAGCACCTGTGGTTCTTTCTGCTGCTGGTGGCCGCTCCCAGATGGGTGCTGTCTGAAGT
GCAGCTGGTGGAATCCGGCGGAGGCCTGGTGCAGCCTGGCGGATCTCTGAGACTGTCTTGTG
CCGCCTCCGGCTTCACCTTCTCCAACTACTACATGGCCTGGGTGCGACAGGCCCCTGGCAAG
GGACTGGAATGGGTGGCCTCTATCGGCACCGTGGGCGGCAACACCTACTACCGGGATTCTGT
GAAGGGCCGGTTCACCATCTCCCGGGACGACTCCAAGTCCACCCTGTACCTGCAGATGAACT
CCCTGCGGGCCGAGGACACCGCCGTGTACTACTGTGCCAGAGAGGACTACGGCGGCTTCCCT
CATTGGGGCCAGGGCACACTCGTGACCGTGTCCTCTGCTTCCACCAAGGGCCCCTCCGTGTT
TCCTCTGGCCCCTTCCAGCAAGTCTACCTCCGGCGGAACAGCCGCTCTGGGCTGCCTCGTGA
AGGACTACTTCCCCGAGCCCGTGACAGTGTCTTGGAACTCTGGCGCCCTGACCAGCGGCGTG
CACACCTTTCCAGCTGTGCTGCAGTCCTCCGGCCTGTACTCCCTGTCCTCCGTCGTGACTGT
GCCCTCCAGCTCTCTGGGCACCCAGACCTACATCTGCAACGTGAACCACAAGCCCTCCAACA
CCAAGGTGGACAAGCGGGTGGAACCCAAGTCCTGCGACAAGACCCACACCTGTCCCCCTTGT
CCTGCCCCTGAACTGCTGGGCGGACCTTCCGTGTTCCTGTTCCCCCCAAAGCCCAAGGACAC
CCTGATGATCTCCCGGACCCCCGAAGTGACCTGCGTGGTGGTGGATGTGTCCCACGAGGACC
CTGAAGTGAAGTTCAATTGGTACGTGGACGGCGTGGAAGTGCACAACGCCAAGACCAAGCCT
AGAGAGGAACAGTACAACTCCACCTACCGGGTGGTGTCCGTGCTGACCGTGCTGCATCAGGA
CTGGCTGAACGGCAAAGAGTACAAGTGCAAGGTGTCCAACAAGGCCCTGCCTGCCCCCATCG
AAAAGACCATCTCCAAGGCCAAGGGCCAGCCCCGGGAACCCCAGGTGTACACACTGCCCCCT
AGCCGGGAAGAGATGACCAAGAACCAGGTGTCCCTGACCTGTCTCGTGAAAGGCTTCTACCC
CTCCGATATCGCCGTGGAATGGGAGTCCAACGGCCAGCCTGAGAACAACTACAAGACCACCC
CCCCTGTGCTGGACTCCGACGGCTCATTCTTCCTGTACAGCAAGCTGACAGTGGACAAGTCC
CGGTGGCAGCAGGGCAACGTGTTCTCCTGCTCCGTGATGCACGAGGCCCTGCACAACCACTA
CACCCAGAAGTCCCTGTCCCTGAGCCCCGGCAAA

[Figure 34]
Nucleotide sequence of h151D-L4 light chain (SEQ ID NO: 38)

ATGGTGCTGCAGACCCAGGTGTTCATCTCCCTGCTGCTGTGGATCTCCGGCGCCTACGGCAA
CATCGTGATGACCCAGTCCCCCTCCAGCCTGTCTGCTTCCGTGGGCGACAGAGTGACCATCA
ACTGCAAGGCCTCCCAGAACGTGGGCACCAACGTGGACTGGTATCAGCAGAAGCCCGGCAAG
TCCCCCAAGCTGCTGATCTACGGCGCCAGCAACAGATACACCGGCGTGCCCGACAGATTCTC
CGGCTCTGGCTCTGGCACCGACTTTACCCTGACCATCAGCTCCCTGCAGCCCGAGGACTTCG
CCACCTACGACTGCCTGCAGTACAAGTACAACCCCTACACCTTCGGCCAGGGCACAAAGGTG
GAAATCAAGCGGACCGTGGCCGCTCCCTCCGTGTTTATCTTCCCACCCTCCGACGAGCAGCT
GAAGTCCGGCACAGCTTCTGTCGTGTGCCTGCTGAACAACTTCTACCCCGCGAGGCCAAGG
TGCAGTGGAAGGTGGACAACGCCCTGCAGTCCGGCAACTCCCAGGAATCCGTGACCGAGCAG
GACTCCAAGGACAGCACCTACTCCCTGTCCTCCACCCTGACCCTGTCCAAGGCCGACTACGA
GAAGCACAAGGTGTACGCCTGCGAAGTGACCCACCAGGGCCTGTCTAGCCCCGTGACCAAGT
CTTTCAACCGGGGCGAGTGC

[Figure 35]
Nucleotide sequence of h198D-H3 heavy chain (SEQ ID NO: 40)

ATGAAGCACCTGTGGTTCTTTCTGCTGCTGGTGGCCGCTCCCAGATGGGTGCTGTCTGAAGT
GCAGCTGGTGGAATCCGGCGGAGGCCTCGTGAAGCCTTCCCAGACCCTGTCTCTGACCTGCA
CCGTGTCCGGCTTCTCCCTGACCTCCTTCCACGTGTCATGGGTGCGACAGCCTCCAGGCAAG
GGCCTGGAATGGATCGCCACCATCTCCTCTGGCGGCGGAACCTACTACAACCCCAGCCTGAA
GTCCAGAGTGACCATCTCCCGGGACACCTCCAAGAACCAGGTGTCCCTGAAGCTGTCCTCCG
TGACCGCCGCTGATACCGCCGTGTACTACTGCGCCAGAATCTCCGGCTGGGGCCACTACTAC
GTGATGGACGTGTGGGGCCAGGGCACCCTCGTGACAGTGTCCTCTGCTTCCACCAAGGGCCC
CTCCGTGTTTCCTCTGGCCCCTTCCAGCAAGTCTACCTCCGGCGGAACAGCCGCTCTGGGCT
GCCTCGTGAAAGACTACTTCCCCGAGCCCGTGACCGTGTCTTGGAACTCTGGCGCTCTGACC
AGCGGCGTGCACACCTTTCCAGCTGTGCTGCAGTCCTCCGGCCTGTACTCCCTGTCCAGCGT
CGTGACTGTGCCCTCCAGCTCTCTGGGCACCCAGACCTACATCTGCAACGTGAACCACAAGC
CCTCCAACACCAAGGTGGACAAGCGGGTGGAACCCAAGTCCTGCGACAAGACCCACACCTGT
CCCCCTTGTCCTGCCCCTGAACTGCTGGGCGGACCTTCCGTGTTCCTGTTCCCCCCAAAGCC
CAAGGACACCCTGATGATCTCCCGGACCCCCGAAGTGACCTGCGTGGTGGTGGATGTGTCCC
ACGAGGACCCTGAAGTGAAGTTCAATTGGTACGTGGACGGCGTGGAAGTGCACAACGCCAAG
ACCAAGCCTAGAGAGGAACAGTACAACTCCACCTACCGGGTGGTGTCCGTGCTGACCGTGCT
GCACCAGGATTGGCTGAACGGCAAAGAGTACAAGTGCAAGGTGTCCAACAAGGCCCTGCCTG
CCCCCATCGAAAAGACCATCAGCAAGGCCAAGGGCCAGCCCCGGGAACCCCAGGTGTACACA
CTGCCCCCTAGCCGGGAAGAGATGACAAAAAATCAGGTGTCACTGACCTGTCTCGTGAAGGG
CTTCTACCCCTCCGATATCGCCGTGGAATGGGAGTCCAACGGCCAGCCTGAGAACAACTACA
AGACCACCCCCCCTGTGCTGGACTCCGACGGCTCATTCTTCCTGTACAGCAAGCTGACAGTG
GACAAGTCCCGGTGGCAGCAGGGCAACGTGTTCTCCTGCTCCGTGATGCACGAGGCCCTGCA
CAACCACTACACCCAGAAGTCCCTGTCCCTGAGCCCCGGCAAA

[Figure 36]
Nucleotide sequence of h198D-L4 light chain (SEQ ID NO: 42)

ATGGTGCTGCAGACCCAGGTGTTCATCTCCCTGCTGCTGTGGATCTCCGGCGCCTACGGCGA
CATCCAGATGACCCAGAGCCCTTCCAGCCTGTCCGCTTCCGTGGGCGACAGAGTGACCATCA
CCTGTCAGGCCTCCGAGGACATCTACTCCGGCCTGGCCTGGTATCAGCAGAAGCCCGGCAAG
TCCCCCAAGCTGCTGATCTACGGCGCTGGATCTCTGCAGGACGGCGTGCCCTCTAGATTCTC
CGGCTCTGGATCCGGCACCCACTACACCCTGACCATCTCCAGCCTGCAGCCCGAGGACTTCG
CTACCTACTTCTGTCAGCAAGGCCTGAAGTTCCCCCTGACCTTCGGCCAGGGCACCAAGGTG
GAAATCAAGCGGACCGTGGCCGCTCCCTCCGTGTTTATCTTCCCACCCTCCGACGAGCAGCT
GAAGTCCGGCACAGCTTCTGTCGTGTGCCTGCTGAACAACTTCTACCCCGCGAGGCCAAGG
TGCAGTGGAAGGTGGACAACGCCCTGCAGTCCGGCAACTCCCAGGAATCCGTGACCGAGCAG
GACTCCAAGGACAGCACCTACTCCCTGTCCTCTACCCTGACCCTGTCCAAGGCCGACTACGA
GAAGCACAAGGTGTACGCCTGCGAAGTGACCCACCAGGGCCTGTCTAGCCCCGTGACCAAGT
CTTTCAACCGGGGCGAGTGC

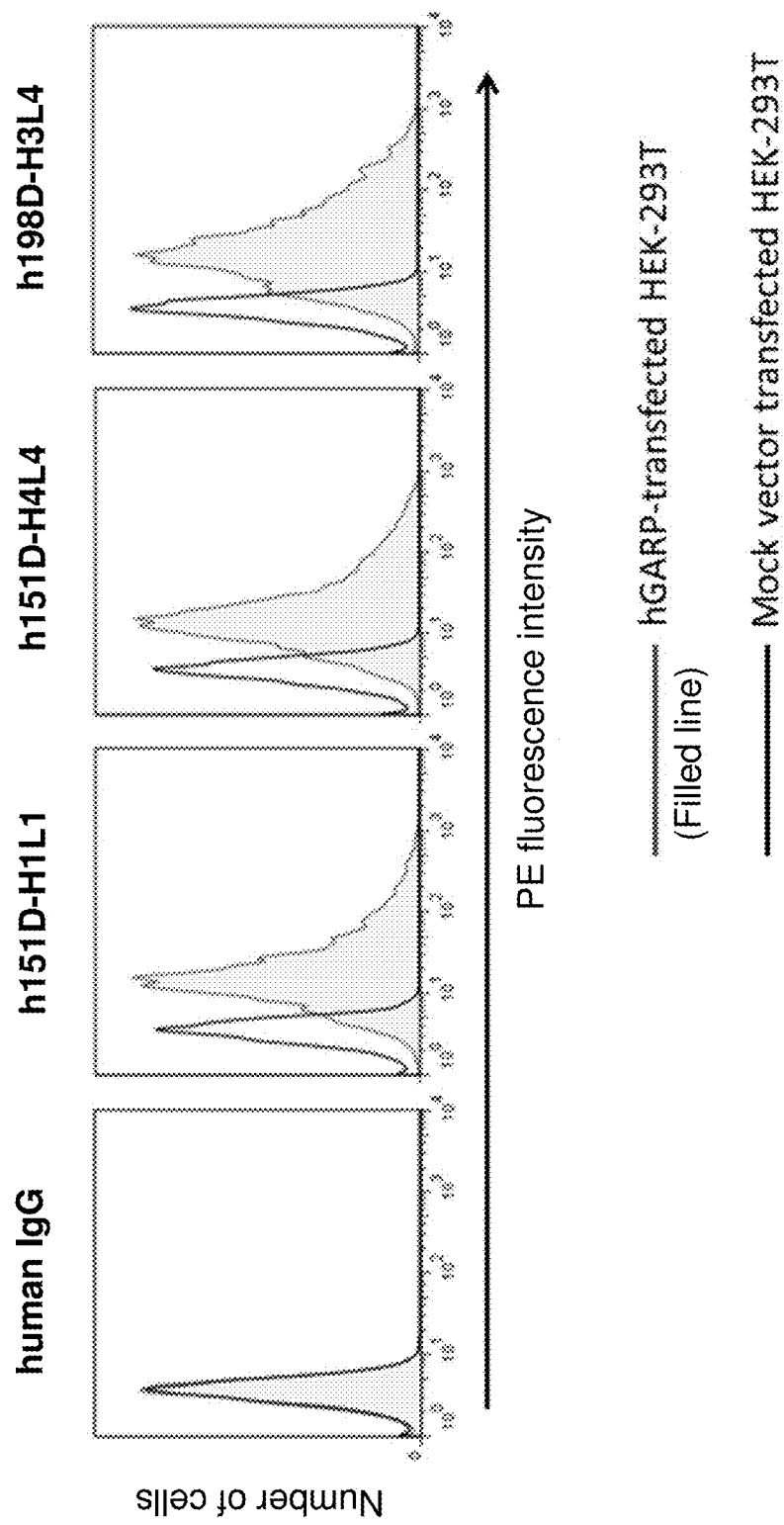
[Figure 37]

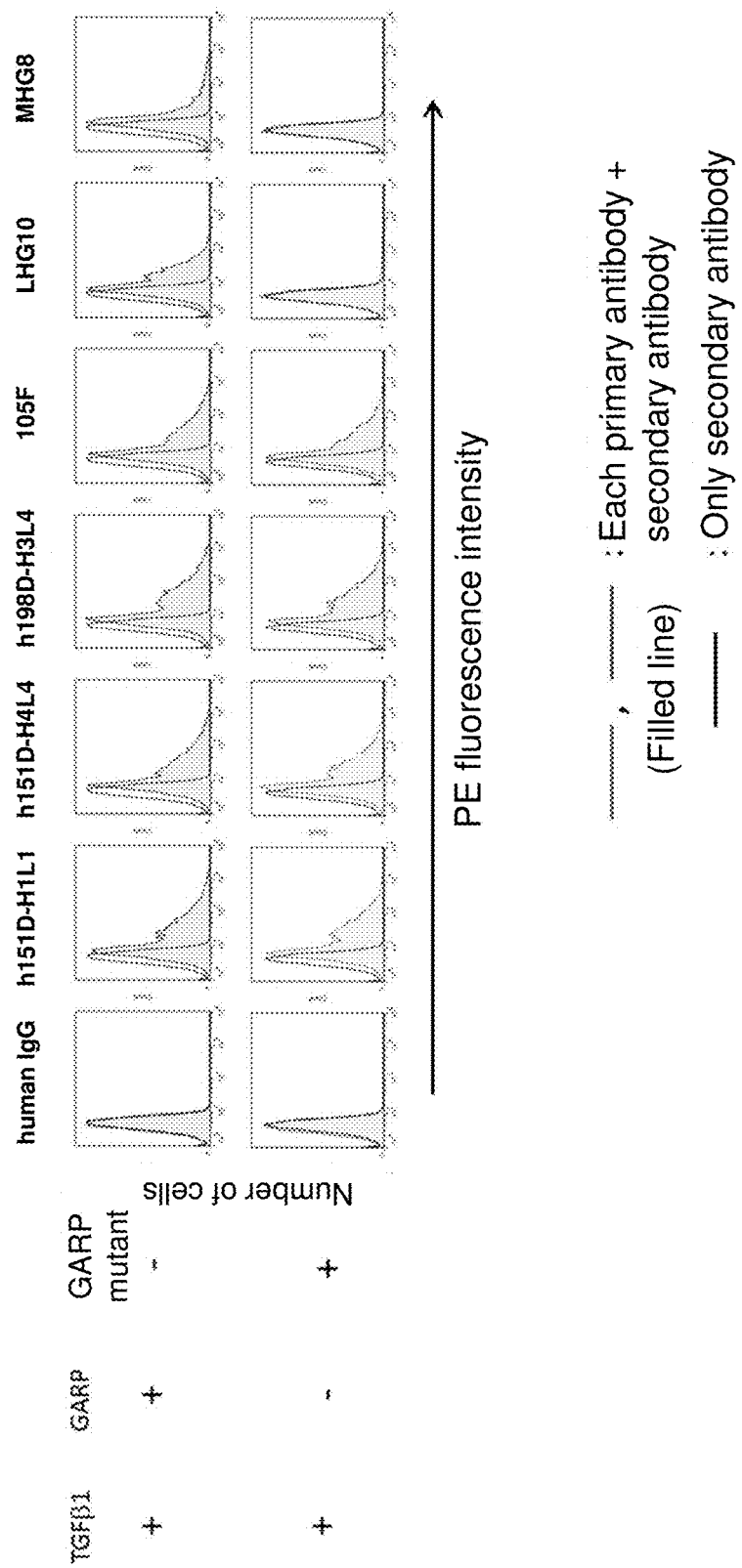
[Figure 38]

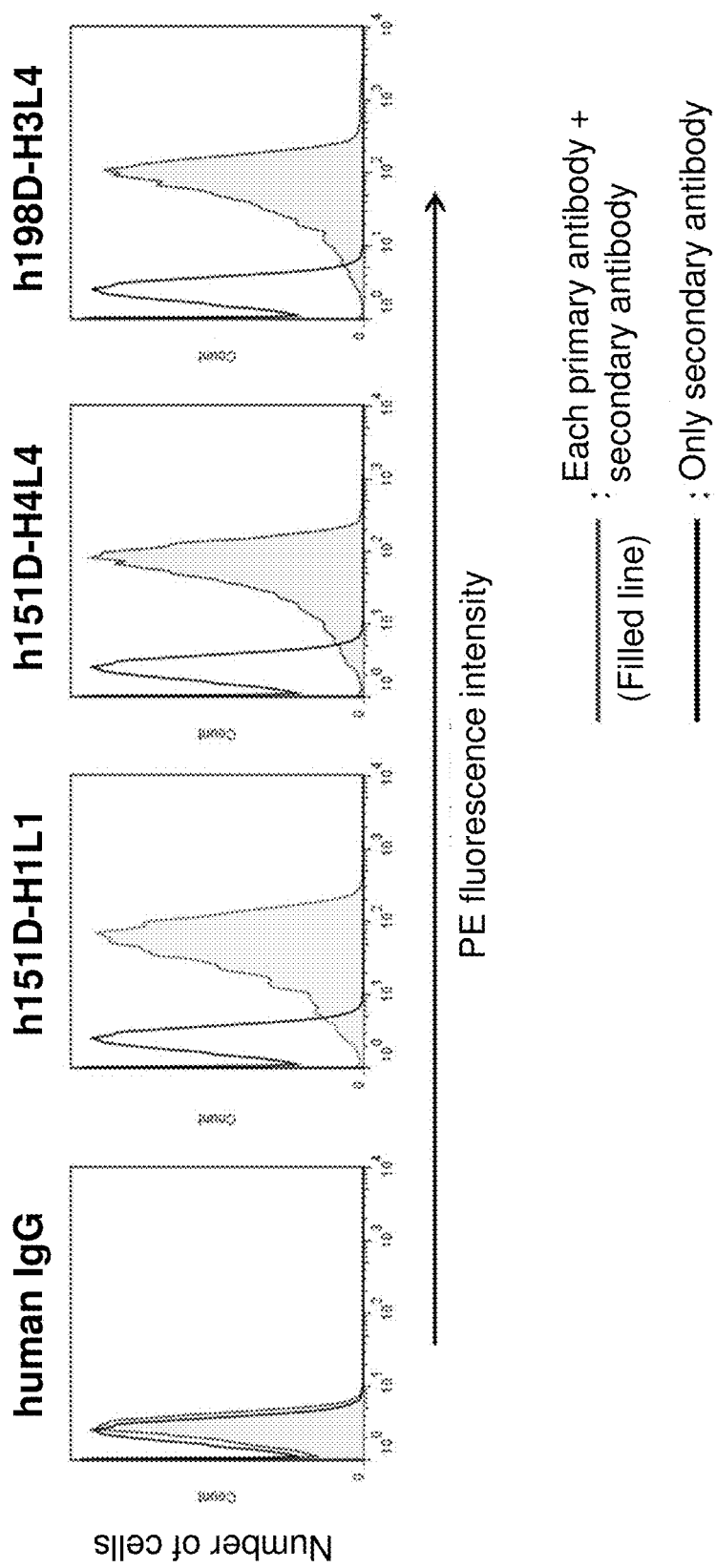
[Figure 39]

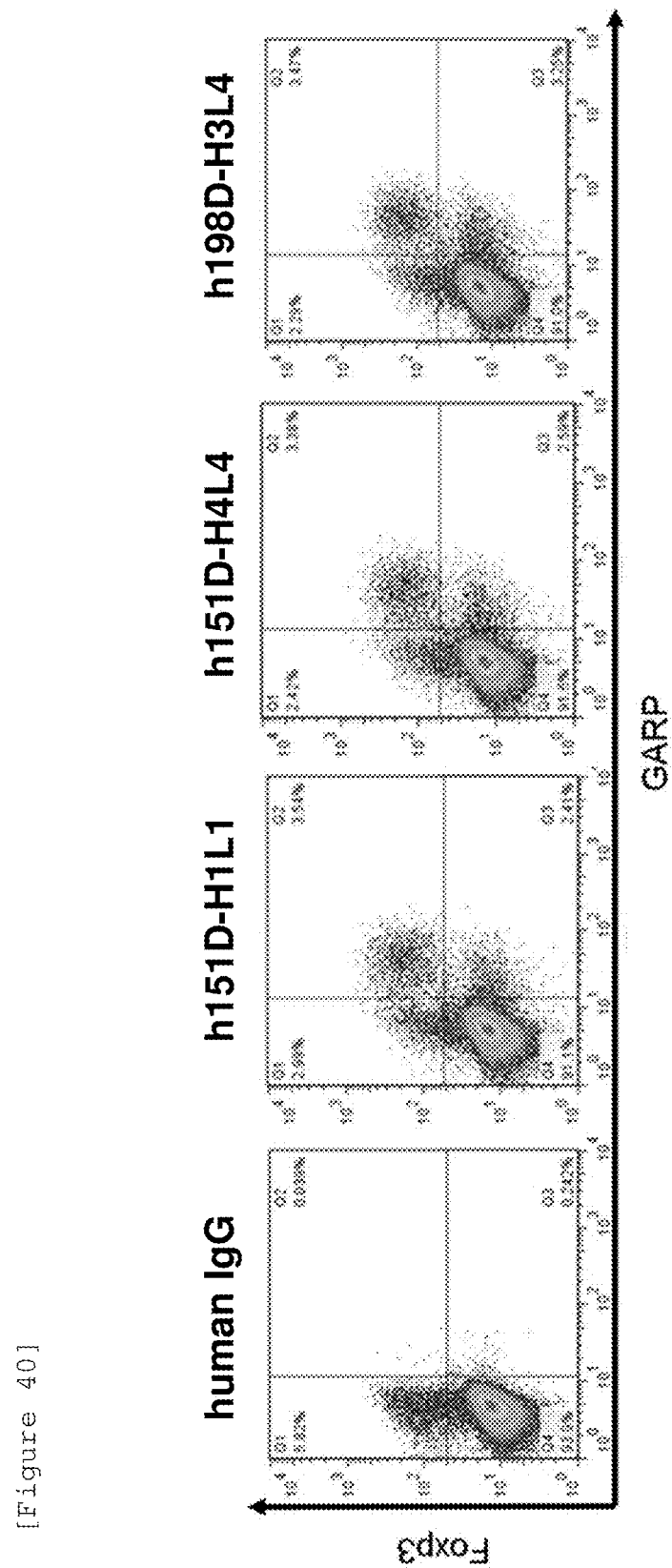
[Figure 40]

[Figure 41]
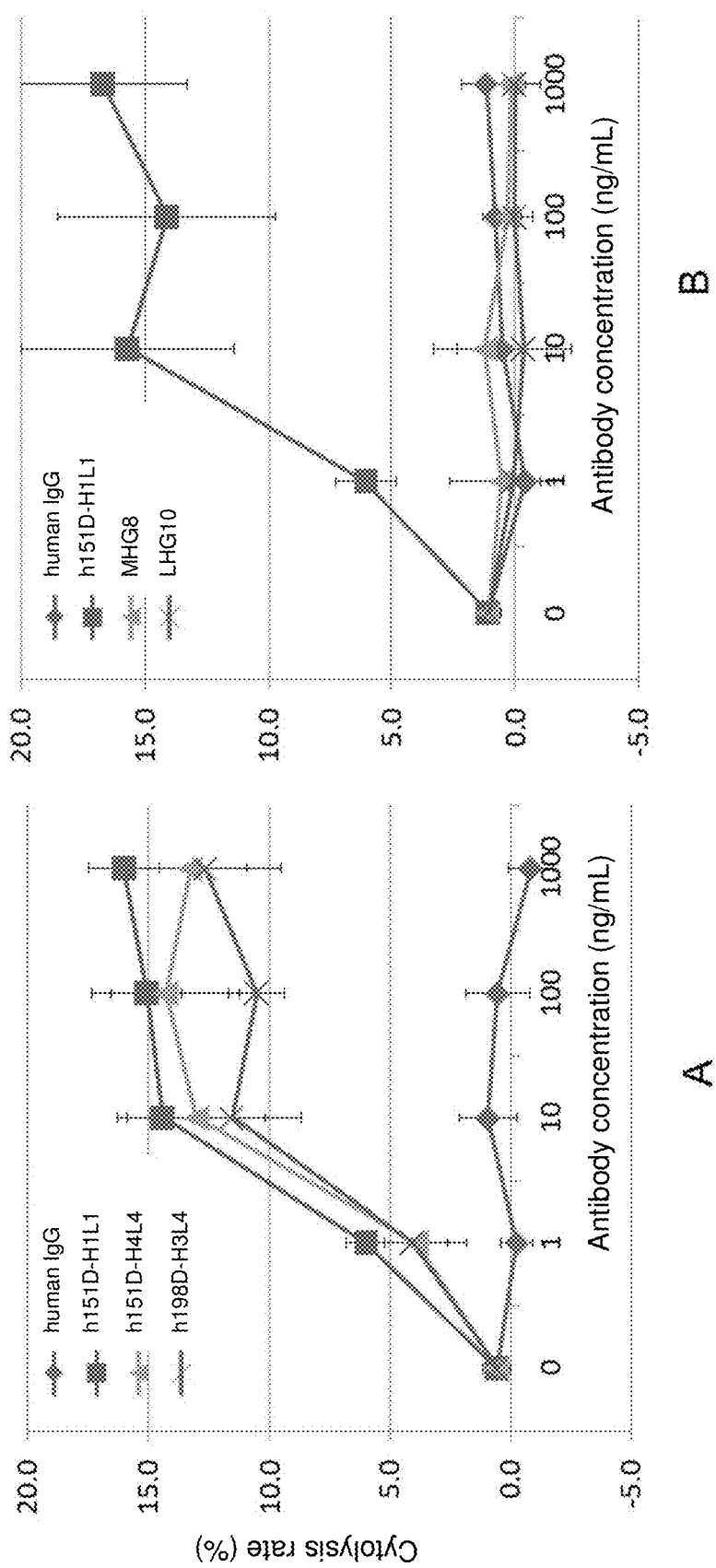

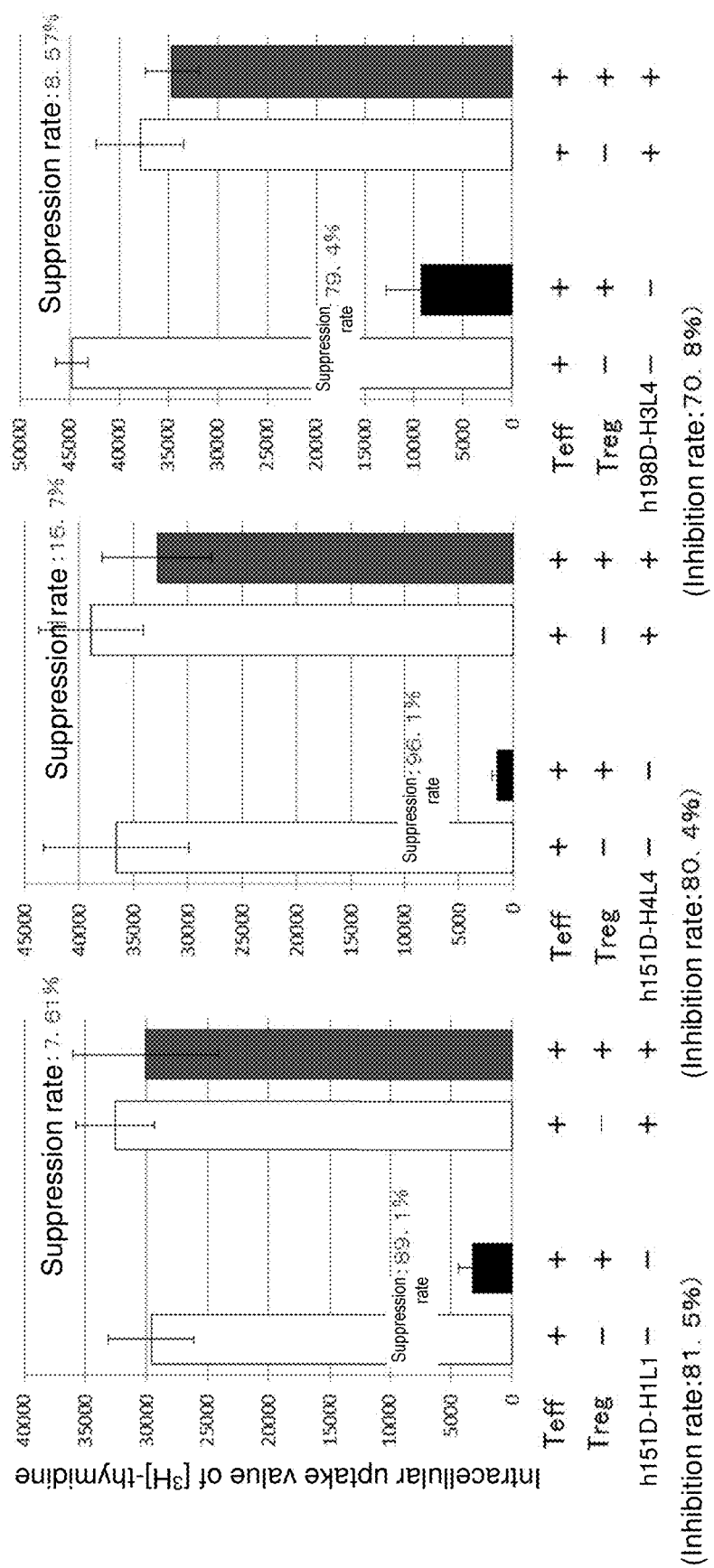

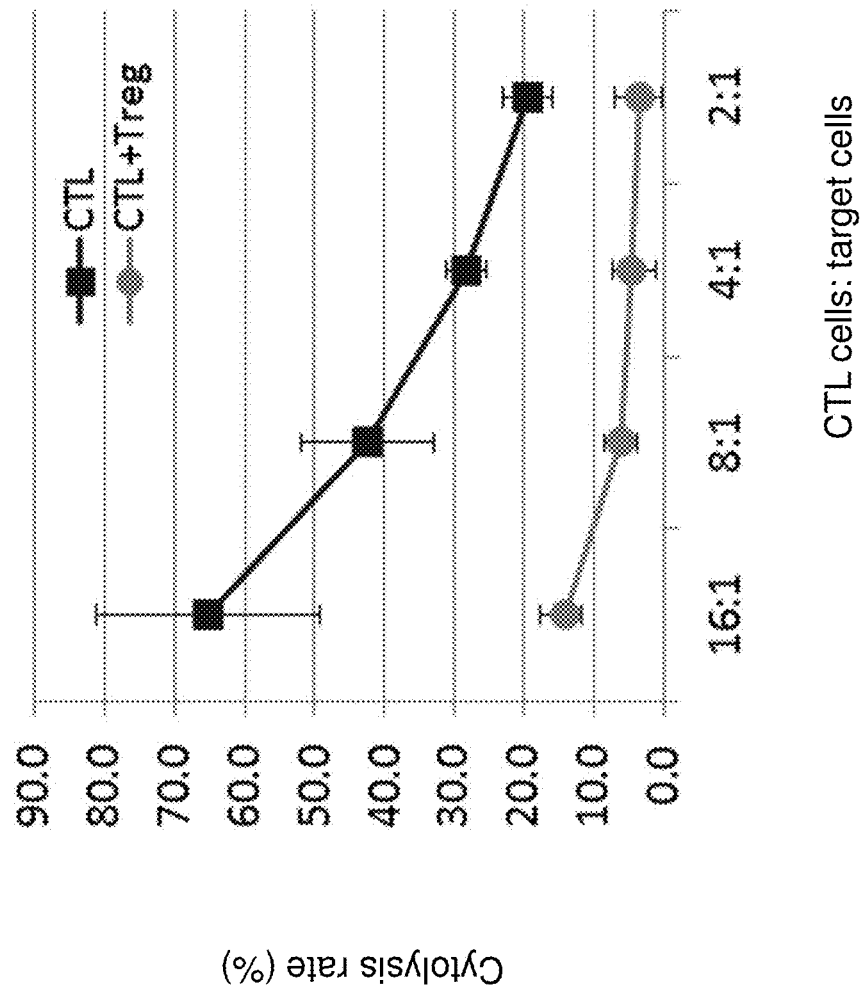
[Figure 43]

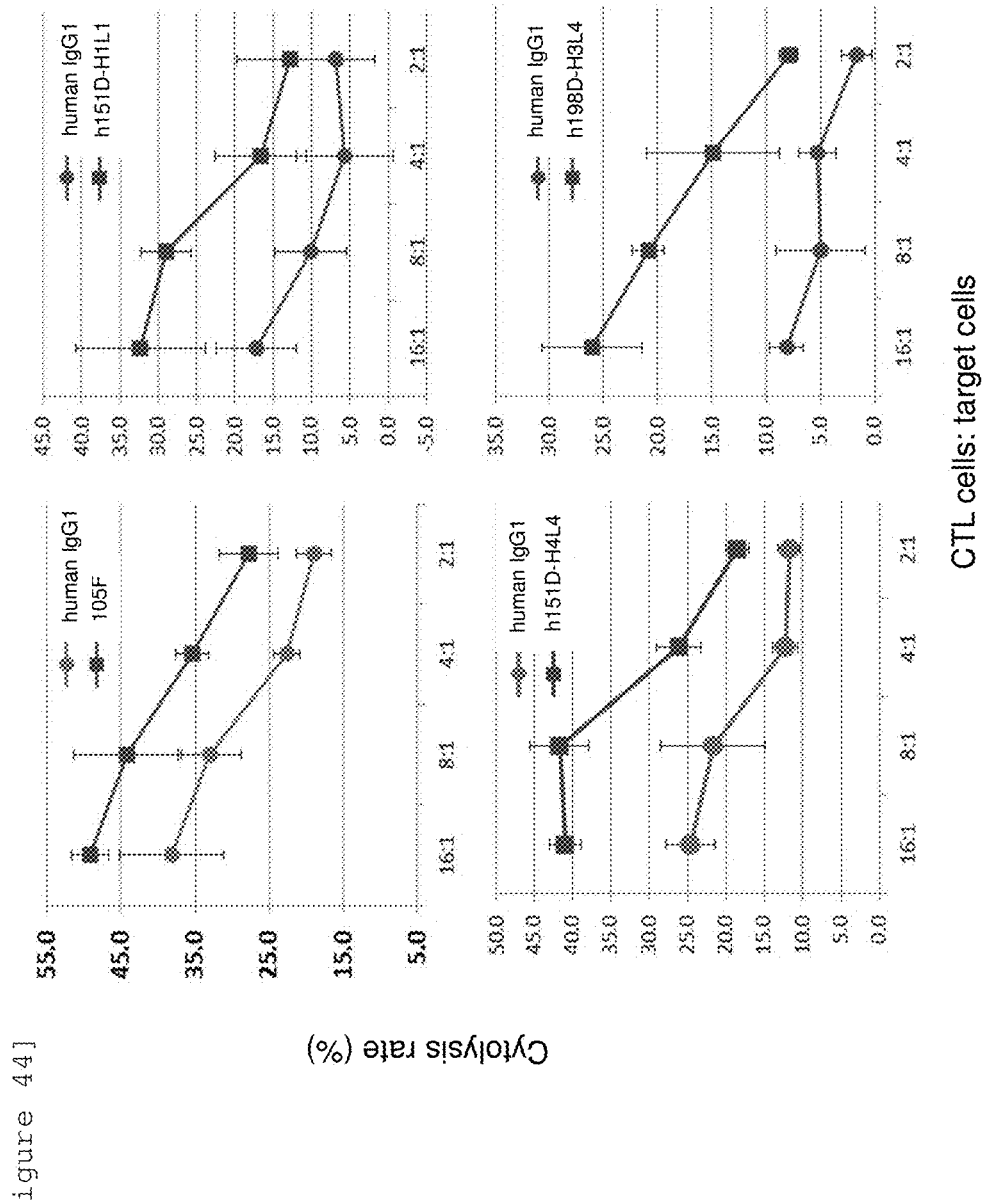
[Figure 44]

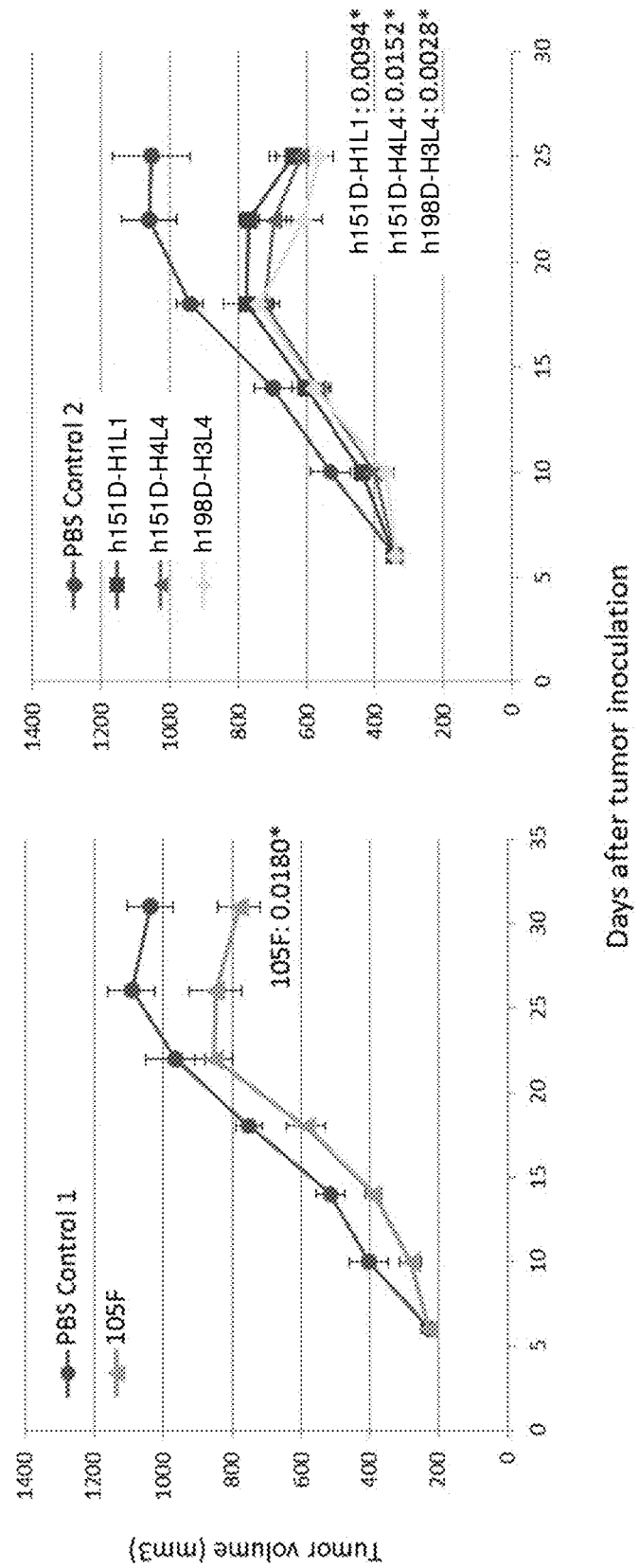
[Figure 45]

ANTI-GARP ANTIBODY

CROSS-REFERENCE TO RELATED APPLICATIONS

The present application is a continuation of U.S. patent application Ser. No. 15/761,045, filed on Mar. 16, 2018, which is a U.S. national stage application of International Patent Application No. PCT/JP2016/078067, filed Sep. 23, 2016, which claims the benefit of priority to Japanese Patent Application No. 2015-187488, filed Sep. 24, 2015, the entireties of which are incorporated herein by reference.

TECHNICAL FIELD

The present invention relates to an antibody that binds to GARP and is useful as a therapeutic agent for a tumor, and a method for treating a tumor using the aforementioned antibody.

BACKGROUND ART

Regulatory T cells (Treg) are the main causative cells inducing immune tolerance that is observed in the tumor area of cancer patients. That is to say, in cancer patients, groups of immune cells that intrinsically work to kill tumors are rendered into a state of immune suppression by activated Treg in the tumor, and this leads to the malignant progression of the tumor [Non Patent Literature 1].

Glycoprotein-A Repetitions Predominant (GARP) is a protein with a single-pass transmembrane structure [Non Patent Literature 2], and this protein is expressed on the cell surface of activated Treg and forms a complex with latent TGF-β (a precursor of TGF-β which is an important molecule for inducing immune tolerance) [Non Patent Literature 3].

As a result of the cell-cell interaction between Treg and target cells to which the Treg induces immunosuppression, TGF-β is matured from latent TGF-β by GARP on the cell surface of Treg and secreted from Treg, and the immunosuppressive signals of TGF-β are directly transmitted to the target cells [Non Patent Literature 4, 5]. It has been demonstrated that the membrane-bound GARP expressed on the cell surface is necessary for such maturation of TGF-β [Non Patent Literature 5]. On the other hand, it has also been demonstrated that soluble GARP that lacks a transmembrane region suppresses proliferation of CD4 positive T cells when it is directly added to the cell culture [Non Patent Literature 6]. Thus, it cannot be ruled out that there is an immunosuppressive mechanism of GARP which does not require TGF-β maturation on the cell membrane.

GARP is not only expressed by Treg from peripheral blood when they get activated, but also in a clinical setting by tumor infiltrating T cells at tumor sites of cancer patients [Non Patent Literature 7], by Treg existing in ascites [Non Patent Literature 8], and also by Treg circulating in the peripheral blood of cancer patients [Non Patent Literature 9].

In a report investigating the effect of inhibition of GARP expression on the function of Treg, siRNA-targeting GARP inhibited the immunosuppressive function of Treg on the proliferative responses of helper T cells, but such an inhibitory effect was partial [Non Patent Literature 10].

In another report, anti-GARP antibodies (MHG-8 and LHG-10) which had been obtained for their abilities to inhibit TGF-β maturation inhibited the suppressive function of A1 cells, which is a Treg cell line [Non Patent Literature 11] established from hemochromatosis patients, on the proliferative responses of helper T cells [Patent Literature 1 and Non Patent Literature 12]. However, it is not known whether or not the aforementioned antibodies effectively exhibit such inhibitory effects on Treg in a tumor microenvironment, and to date, no anti-GARP antibody having such effects has been reported so far. An antibody recognizing both GARP and TGF-β is also known [Patent Literature 2].

It has been demonstrated that the excessive presence and the activation of Treg in patients having malaria and HIV infection exhibit a correlation with the disease state [Non Patent Literatures 13 and 14], and that the removal of Treg resulted in remission of the disease state in murine models for the diseases [Non Patent Literatures 15 and 16].

CITATION LIST

Patent Literature

Patent Literature 1: WO2015/015003
Patent Literature 2: WO2016/125017

Non Patent Literature

Non Patent Literature: 1: Int J Cancer. 2010 Aug. 15; 127(4): 759-67.
Non Patent Literature: 2: PLoS One. 2008; 3(7): e2705.
Non Patent Literature: 3: Proc Natl Acad Sci USA. 2009; 106(32): 13445-50.
Non Patent Literature: 4: Eur J Immunol. 2009; 39(12): 3315-22.
Non Patent Literature: 5: Mol Biol Cell. 2012; 23(6): 1129-39.
Non Patent Literature: 6: Blood. 2013; 122(7): 1182-91.
Non Patent Literature: 7: Eur J Immunol. 2012 Jul; 42(7): 1876-85.
Non Patent Literature: 8: Clin Immunol. 2013 October; 149(1): 97-110.
Non Patent Literature: 9: Cancer Res. 2013; 73: 2435.
Non Patent Literature: 10: Proc Natl Acad Sci USA. 2009 Aug. 11; 106(32): 13445-50.
Non Patent Literature: 11: Eur J Immunol. 2009; 39(12): 869-82.
Non Patent Literature: 12: Sci Transl Med. 2015 Apr. 22; 7(284)
Non Patent Literature: 13: PLoS One. 2008 Apr. 30; 3(4): e2027.
Non Patent Literature: 14: Clin Exp Immunol. 2014 June; 176(3): 401-9.
Non Patent Literature: 15: J Immunol. 2012 Jun. 1; 188(11): 5467-77.
Non Patent Literature: 16: PLoS Pathog. 2013; 9(12): e1003798.

SUMMARY OF INVENTION

Technical Problem

It is an object of the present invention to provide an antibody, which inhibits the function of Treg in a tumor and is thereby used as a pharmaceutical product having therapeutic effects, a method for treating a tumor using the aforementioned antibody, and the like.

Solution to Problem

The present inventors have conducted intensive studies directed towards achieving the aforementioned object. As a result, the inventors have found an antibody that specifically binds to GARP and exhibits an activity of inhibiting the function of Treg via antibody-dependent cellular cytotoxicity, thereby completing the present invention. Specifically, the present invention includes the following aspects of the invention.

(1) An antibody having the following properties:
(a) specifically binding to Glycoprotein-A Repetitions Predominant (GARP);
(b) having an inhibitory activity to the immunosuppressive function of regulatory T cells;
(c) having antibody-dependent cellular cytotoxic (ADCC) activity; and
(d) having in vivo antitumor activity.
(2) The antibody according to the above (1), wherein the GARP is a molecule consisting of the amino acid sequence shown in SEQ ID NO: 1.
(3) The antibody according to the above (1) or (2), which binds to:
(a) amino acid sequence portions at amino acid positions 366 to 377, 407 to 445 and 456 to 470 shown in SEQ ID NO: 1,
(b) amino acid sequence portions at amino acid positions 54 to 112 and 366 to 392 shown in SEQ ID NO: 1,
(c) amino acid sequence portions at amino acid positions 352 to 392 shown in SEQ ID NO: 1, or
(d) amino acid sequence portions at amino acid positions 18 to 112 shown in SEQ ID NO: 1.
(4) The antibody according to any one of the above (1) to (3), which has competitive inhibitory activity, for binding to GARP, against an antibody having:
(a) a heavy chain consisting of the amino acid sequence shown in SEQ ID NO: 2 and a light chain consisting of the amino acid sequence shown in SEQ ID NO: 3,
(b) a heavy chain consisting of the amino acid sequence shown in SEQ ID NO: 4 and a light chain consisting of the amino acid sequence shown in SEQ ID NO: 5,
(c) a heavy chain consisting of the amino acid sequence shown in SEQ ID NO: 25 and a light chain consisting of the amino acid sequence shown in SEQ ID NO: 27, or
(d) a heavy chain consisting of the amino acid sequence shown in SEQ ID NO: 29 and a light chain consisting of the amino acid sequence shown in SEQ ID NO: 31.
(5) The antibody according to any one of the above (1) to (4), wherein the tumor is a cancer.
(6) The antibody according to the above (5), wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.
(7) The antibody according to any one of the above (1) to (6), which has:
(a) CDRH1 consisting of the amino acid sequence at amino acid positions 26 to 35 shown in SEQ ID NO: 2, CDRH2 consisting of the amino acid sequence at amino acid positions 50 to 66 shown in SEQ ID NO: 2 and CDRH3 consisting of the amino acid sequence at amino acid positions 99 to 107 shown in SEQ ID NO: 2, and CDRL1 consisting of the amino acid sequence at amino acid positions 23 to 36 shown in SEQ ID NO: 3, CDRL2 consisting of the amino acid sequence at amino acid positions 52 to 58 shown in SEQ ID NO: 3 and CDRL3 consisting of the amino acid sequence at amino acid positions 91 to 101 shown in SEQ ID NO: 3,
(b) CDRH1 consisting of the amino acid sequence at amino acid positions 26 to 35 shown in SEQ ID NO: 4, CDRH2 consisting of the amino acid sequence at amino acid positions 50 to 66 shown in SEQ ID NO: 4 and CDRH3 consisting of the amino acid sequence at amino acid positions 99 to 112 shown in SEQ ID NO: 4, and CDRL1 consisting of the amino acid sequence at amino acid positions 23 to 36 shown in SEQ ID NO: 5, CDRL2 consisting of the amino acid sequence at amino acid positions 52 to 58 shown in SEQ ID NO: 5 and CDRL3 consisting of the amino acid sequence at amino acid positions 91 to 100 shown in SEQ ID NO: 5,
(c) CDRH1 consisting of the amino acid sequence at amino acid positions 45 to 54 shown in SEQ ID NO: 25, CDRH2 consisting of the amino acid sequence at amino acid positions 69 to 78 shown in SEQ ID NO: 25 and CDRH3 consisting of the amino acid sequence at amino acid positions 118 to 125 shown in SEQ ID NO: 25, and CDRL1 consisting of the amino acid sequence at amino acid positions 44 to 54 shown in SEQ ID NO: 27, CDRL2 consisting of the amino acid sequence at amino acid positions 70 to 76 shown in SEQ ID NO: 27 and CDRL3 consisting of the amino acid sequence at amino acid positions 109 to 117 shown in SEQ ID NO: 27, or
(d) CDRH1 consisting of the amino acid sequence at amino acid positions 45 to 54 shown in SEQ ID NO: 29, CDRH2 consisting of the amino acid sequence at amino acid positions 69 to 77 shown in SEQ ID NO: 29 and CDRH3 consisting of the amino acid sequence at amino acid positions 117 to 128 shown in SEQ ID NO: 29, and CDRL1 consisting of the amino acid sequence at amino acid positions 44 to 54 shown in SEQ ID NO: 31, CDRL2 consisting of the amino acid sequence at amino acid positions 70 to 76 shown in SEQ ID NO: 31 and CDRL3 consisting of the amino acid sequence at amino acid positions 109 to 117 shown in SEQ ID NO: 31.
(8) The antibody according to any one of the above (1) to (7), which has:
(a) a heavy chain variable region consisting of the amino acid sequence at amino acid positions 1 to 118 shown in SEQ ID NO: 2, and a light chain variable region consisting of the amino acid sequence at amino acid positions 1 to 112 shown in SEQ ID NO: 3,
(b) a heavy chain variable region consisting of the amino acid sequence at amino acid positions 1 to 123 shown in SEQ ID NO: 4, and a light chain variable region consisting of the amino acid sequence at amino acid positions 1 to 111 shown in SEQ ID NO: 5,
(c) a heavy chain variable region consisting of the amino acid sequence at amino acid positions 20 to 136 shown in SEQ ID NO: 25, and a light chain variable region consisting of the amino acid sequence at amino acid positions 21 to 129 shown in SEQ ID NO: 27, or
(d) a heavy chain variable region consisting of the amino acid sequence at amino acid positions 20 to 139 shown in SEQ ID NO: 29, and a light chain variable region consisting of the amino acid sequence at amino acid positions 21 to 129 shown in SEQ ID NO: 31.
(9) The antibody according to any one of the above (1) to (8), wherein the constant region is a human-derived constant region. (10)The antibody according to any one of the above (1) to (9), which has:
(a) a heavy chain consisting of the amino acid sequence shown in SEQ ID NO: 2, and a light chain consisting of the amino acid sequence shown in SEQ ID NO: 3,
(b) a heavy chain consisting of the amino acid sequence shown in SEQ ID NO: 4, and a light chain consisting of the amino acid sequence shown in SEQ ID NO: 5, (c) a heavy chain consisting of the amino acid sequence at amino acid positions 20 to 466 shown in SEQ ID NO: 25, and a light chain consisting of the amino acid sequence at amino acid positions 21 to 234 shown in SEQ ID NO: 27, or
(d) a heavy chain consisting of the amino acid sequence at amino acid positions 20 to 469 shown in SEQ ID NO: 29, and a light chain consisting of the amino acid sequence at amino acid positions 21 to 234 shown in SEQ ID NO: 31.
(11) The antibody according to any one of the above (1) to (10), which is humanized.
(12) The antibody according to the above (11), which has:
a heavy chain variable region consisting of an amino acid sequence selected from the group consisting of:
(a) the amino acid sequence at amino acid positions 20 to 136 shown in SEQ ID NO: 33,
(b) the amino acid sequence at amino acid positions 20 to 136 shown in SEQ ID NO: 35,
(c) the amino acid sequence at amino acid positions 20 to 139 shown in SEQ ID NO: 41,
(d) an amino acid sequence having homology of at least 95% or more to the sequence of a framework region other than at each CDR sequence in the sequences of (a) to (c), and
(e) an amino acid sequence comprising a deletion, substitution or addition of one or several amino acids in the sequence of a framework region other than at each CDR sequence in the sequences of (a) to (c), and
a light chain variable region consisting of an amino acid sequence selected from the group consisting of:
(f) the amino acid sequence at amino acid positions 21 to 129 shown in SEQ ID NO: 37,
(g) the amino acid sequence at amino acid positions 21 to 129 shown in SEQ ID NO: 39,
(h) the amino acid sequence at amino acid positions 21 to 129 shown in SEQ ID NO: 43,
(i) an amino acid sequence having homology of at least 95% or more to the sequence of a framework region other than at each CDR sequence in the sequences of (f) to (h), and
(j) an amino acid sequence comprising a deletion, substitution or addition of one or several amino acids in the sequence of a framework region other than at each CDR sequence in the sequences of (f) to (h).
(13) The antibody according to the above (11) or (12), which has:
(a) a heavy chain variable region consisting of the amino acid sequence at amino acid positions 20 to 136 shown in SEQ ID NO: 33, and a light chain variable region consisting of the amino acid sequence at amino acid positions 21 to 129 shown in SEQ ID NO: 37,
(b) a heavy chain variable region consisting of the amino acid sequence at amino acid positions 20 to 136 shown in SEQ ID NO: 35, and a light chain variable region consisting of the amino acid sequence at amino acid positions 21 to 129 shown in SEQ ID NO: 39, or
(c) a heavy chain variable region consisting of the amino acid sequence at amino acid positions 21 to 139 shown in SEQ ID NO: 41, and a light chain variable region consisting of the amino acid sequence at amino acid positions 21 to 129 shown in SEQ ID NO: 43.
(14) The antibody according to any one of the above (11) to (13), which has:
(a) a heavy chain selected from the group consisting of a heavy chain having the amino acid sequence at amino acid positions 20 to 466 shown in SEQ ID NO: 33, a heavy chain having the amino acid sequence at amino acid positions 20 to 466 shown in SEQ ID NO: 35, and a heavy chain having the amino acid sequence at amino acid positions 20 to 469 shown in SEQ ID NO: 41, and
(b) a light chain selected from the group consisting of a light chain having the amino acid sequence at amino acid positions 21 to 234 shown in SEQ ID NO: 37, a light chain having the amino acid sequence at amino acid positions 21 to 234 shown in SEQ ID NO: 39, and a light chain having the amino acid sequence at amino acid positions 21 to 234 shown in SEQ ID NO: 43.
(15) The antibody according to any one of the above (11) to (14), which has:
(a) a heavy chain having the amino acid sequence at amino acid positions 20 to 466 shown in SEQ ID NO: 33, and a light chain having the amino acid sequence at amino acid positions 21 to 234 shown in SEQ ID NO: 37,
(b) a heavy chain having the amino acid sequence at amino acid positions 20 to 466 shown in SEQ ID NO: 35, and a light chain having the amino acid sequence at amino acid positions 21 to 234 shown in SEQ ID NO: 39, or
(c) a heavy chain having the amino acid sequence at amino acid positions 20 to 469 shown in SEQ ID NO: 41, and a light chain having the amino acid sequence at amino acid positions 21 to 234 shown in SEQ ID NO: 43.
(16) A polynucleotide encoding the antibody according to any one of the above (1) to (15).
(17) The polynucleotide according to the above (16), which has:
(a) a polynucleotide of CDRH1 consisting of the nucleotide sequence at nucleotide positions 76 to 105 shown in SEQ ID NO: 6, a polynucleotide of CDRH2 consisting of the nucleotide sequence at nucleotide positions 148 to 198 shown in SEQ ID NO: 6 and a polynucleotide of CDRH3 consisting of the nucleotide sequence at nucleotide positions 295 to 321 shown in SEQ ID NO: 6, and a polynucleotide of CDRL1 consisting of the nucleotide sequence at nucleotide positions 67 to 108 shown in SEQ ID NO: 7, a polynucleotide of CDRL2 consisting of the nucleotide sequence at nucleotide positions 154 to 174 shown in SEQ ID NO: 7 and a polynucleotide of CDRL3 consisting of the nucleotide sequence at nucleotide positions 271 to 303 shown in SEQ ID NO: 7,
(b) a polynucleotide encoding CDRH1 consisting of the nucleotide sequence at nucleotide positions 76 to 105 shown in SEQ ID NO: 8, a polynucleotide of CDRH2 consisting of the nucleotide sequence at nucleotide positions 148 to 198 shown in SEQ ID NO: 8 and a polynucleotide of CDRH3 consisting of the nucleotide sequence at nucleotide positions 295 to 336 shown in SEQ ID NO: 8, and a polynucleotide of CDRL1 consisting of the nucleotide sequence at nucleotide positions 67 to 108 shown in SEQ ID NO: 9, a polynucleotide of CDRL2 consisting of the nucleotide sequence at nucleotide positions 154 to 174 shown in SEQ ID NO: 9 and a polynucleotide of CDRL3 consisting of the nucleotide sequence at nucleotide positions 271 to 300 shown in SEQ ID NO: 9,
(c) a polynucleotide of CDRH1 consisting of the nucleotide sequence at nucleotide positions 133 to 162 shown in SEQ ID NO: 24, a polynucleotide of CDRH2 consisting of the nucleotide sequence at nucleotide positions 205 to 234 shown in SEQ ID NO: 24 and a polynucleotide of CDRH3 consisting of the nucleotide sequence at nucleotide positions 352 to 375 shown in SEQ ID NO: 24, and a polynucleotide of CDRL1 consisting of the nucleotide sequence at nucleotide positions 130 to 162 shown in SEQ ID NO: 26, a polynucleotide of CDRL2 consisting of the nucleotide sequence at nucleotide positions 208 to 228 shown in SEQ ID NO: 26 and a polynucleotide of CDRL3 consisting of the nucleotide sequence at nucleotide positions 325 to 351 shown in SEQ ID NO: 26, or (d) a polynucleotide of CDRH1 consisting of the nucleotide sequence at nucleotide positions 133 to 162 shown in SEQ ID NO: 28, a polynucleotide of CDRH2 consisting of the nucleotide sequence at nucleotide positions 205 to 231 shown in SEQ ID NO: 28 and a polynucleotide of CDRH3 consisting of the nucleotide sequence at nucleotide positions 349 to 384 shown in SEQ ID NO: 28, and a polynucleotide of CDRL1 consisting of the nucleotide sequence at nucleotide positions 130 to 162 shown in SEQ ID NO: 30, a polynucleotide of CDRL2 consisting of the nucleotide sequence at nucleotide positions 208 to 228 shown in SEQ ID NO: 30 and a polynucleotide of CDRL3 consisting of the nucleotide sequence at nucleotide positions 325 to 351 shown in SEQ ID NO: 30.

(18) The polynucleotide according to the above (16) or (17), which has:

(a) a polynucleotide of a heavy chain variable region consisting of the nucleotide sequence at nucleotide positions 1 to 354 shown in SEQ ID NO: 6, and a polynucleotide of a light chain variable region consisting of the nucleotide sequence at nucleotide positions 1 to 336 shown in SEQ ID NO: 7, (b) a polynucleotide of a heavy chain variable region consisting of the nucleotide sequence at nucleotide positions 1 to 369 shown in SEQ ID NO: 8, and a polynucleotide of a light chain variable region consisting of the nucleotide sequence at nucleotide positions 1 to 333 shown in SEQ ID NO: 9, (c) a polynucleotide of a heavy chain variable region consisting of the nucleotide sequence at nucleotide positions 58 to 408 shown in SEQ ID NO: 24, and a polynucleotide of a light chain variable region consisting of the nucleotide sequence at nucleotide positions 61 to 387 shown in SEQ ID NO: 26, or (d) a polynucleotide of a heavy chain variable region consisting of the nucleotide sequence at nucleotide positions 58 to 417 shown in SEQ ID NO: 28, and a polynucleotide of a light chain variable region consisting of the nucleotide sequence at nucleotide positions 61 to 387 shown in SEQ ID NO: 30.

(19) The polynucleotide according to any one of the above (16) to (18), which has:

(a) a polynucleotide of a heavy chain consisting of the nucleotide sequence shown in SEQ ID NO: 6, and a polynucleotide of a light chain consisting of the nucleotide sequence shown in SEQ ID NO: 7, (b) a polynucleotide of a heavy chain consisting of the nucleotide sequence shown in SEQ ID NO: 8, and a polynucleotide of a light chain consisting of the nucleotide sequence shown in SEQ ID NO: 9, (c) a polynucleotide of a heavy chain consisting of the nucleotide sequence at nucleotide positions 58 to 1398 shown in SEQ ID NO: 24, and a polynucleotide of a light chain consisting of the nucleotide sequence at nucleotide positions 61 to 702 shown in SEQ ID NO: 26, or (d) a polynucleotide of a heavy chain consisting of the nucleotide sequence at nucleotide positions 58 to 1407 shown in SEQ ID NO: 28, and a polynucleotide of a light chain consisting of the nucleotide sequence at nucleotide positions 61 to 702 shown in SEQ ID NO: 30.

(20) The polynucleotide according to the above (16) or (17), which has:

(a) a polynucleotide of a heavy chain variable region selected from the group consisting of a polynucleotide of a heavy chain variable region consisting of the nucleotide sequence at nucleotide positions 58 to 408 shown in SEQ ID NO: 32, a polynucleotide of a heavy chain variable region consisting of the nucleotide sequence at nucleotide positions 58 to 408 shown in SEQ ID NO: 34, and a polynucleotide of a heavy chain variable region consisting of the nucleotide sequence at nucleotide positions 58 to 417 shown in SEQ ID NO: 40, and (b) a polynucleotide of a light chain variable region selected from the group consisting of a polynucleotide of a light chain variable region consisting of the nucleotide sequence at nucleotide positions 61 to 387 shown in SEQ ID NO: 36, a polynucleotide of a light chain variable region consisting of the nucleotide sequence at nucleotide positions 61 to 387 shown in SEQ ID NO: 38, and a polynucleotide of a light chain variable region consisting of the nucleotide sequence at nucleotide positions 61 to 387 shown in SEQ ID NO: 42.

(21) The polynucleotide according to the above (16), (17) or (20), which has:

(a) a polynucleotide of a heavy chain variable region consisting of the nucleotide sequence at nucleotide positions 58 to 408 shown in SEQ ID NO: 32, and a polynucleotide of a light chain variable region consisting of the nucleotide sequence at nucleotide positions 61 to 387 shown in SEQ ID NO: 36, (b) a polynucleotide of a heavy chain variable region consisting of the nucleotide sequence at nucleotide positions 58 to 408 shown in SEQ ID NO: 34, and a polynucleotide of a light chain variable region consisting of the nucleotide sequence at nucleotide positions 61 to 387 shown in SEQ ID NO: 38, or (c) a polynucleotide of a heavy chain variable region consisting of the nucleotide sequence at nucleotide positions 58 to 417 shown in SEQ ID NO: 40, and a polynucleotide of a light chain variable region consisting of the nucleotide sequence at nucleotide positions 61 to 387 shown in SEQ ID NO: 42.

(22) The polynucleotide according to the above (16), (17), (20) or (21), which has:

(a) a polynucleotide of a heavy chain selected from the group consisting of a polynucleotide of a heavy chain consisting of the nucleotide sequence at nucleotide positions 58 to 1398 shown in SEQ ID NO: 32, a polynucleotide of a heavy chain consisting of the nucleotide sequence at nucleotide positions 58 to 1398 shown in SEQ ID NO: 34, and a polynucleotide of a heavy chain consisting of the nucleotide sequence at nucleotide positions 58 to 1407 shown in SEQ ID NO: 40, and (b) a polynucleotide of a light chain selected from the group consisting of a polynucleotide of a light chain consisting of the nucleotide sequence at nucleotide positions 61 to 702 shown in SEQ ID NO: 36, a polynucleotide of a light chain consisting of the nucleotide sequence at nucleotide positions 61 to 702 shown in SEQ ID NO: 38, and a polynucleotide of a light chain consisting of the nucleotide sequence at nucleotide positions 61 to 702 shown in SEQ ID NO: 42.

(23) The polynucleotide according to any one of the above (16), (17) and (20) to (22), which has:

(a) a polynucleotide of a heavy chain consisting of the nucleotide sequence at nucleotide positions 58 to 1398 shown in SEQ ID NO: 32, and a polynucleotide of a light chain consisting of the nucleotide sequence at nucleotide positions 61 to 702 shown in SEQ ID NO: 36, (b) a polynucleotide of a heavy chain consisting of the nucleotide sequence at nucleotide positions 58 to 1398 shown in SEQ ID NO: 34, and a polynucleotide of a light chain consisting of the nucleotide sequence at nucleotide positions 61 to 702 shown in SEQ ID NO: 38, or (c) a polynucleotide of a heavy chain consisting of the nucleotide sequence at nucleotide positions 58 to 1407 shown in SEQ ID NO: 40, and a polynucleotide of a light chain consisting of the nucleotide sequence at nucleotide positions 61 to 702 shown in SEQ ID NO: 42.

(24) An expression vector comprising the polynucleotide according to any one of the above (16) to (23).

(25) Host cells transformed with the expression vector according to the above (24).

(26) A method for producing an antibody of interest or a fragment thereof, which comprises a step of culturing the host cells according to the above (25), and a step of collecting an antibody of interest from the culture obtained by the aforementioned step.

(27) An antibody obtained by the production method according to the above (26).

(28) The antibody according to any one of the above (1) to (15) and (27), comprising one or two or more modifications selected from the group consisting of N-linked glycosylation, O-linked glycosylation, N-terminal processing, C-terminal processing, deamidation, isomerization of aspartic acid, oxidation of methionine, addition of a methionine residue to the N-terminus, amidation of a proline residue, and a heavy chain comprising a deletion of one or two amino acids at the carboxyl terminus.

(29) The antibody according to the above (28), wherein one or two amino acids are deleted at the carboxyl terminus of a heavy chain thereof.

(30) The antibody according to the above (29), wherein one amino acid is deleted at each of the carboxyl termini of both of the heavy chains thereof.

(31) The antibody according to any one of the above (28) to (30), wherein a proline residue at the carboxyl terminus of a heavy chain thereof is further amidated.

(32) The antibody according to any one of the above (1) to (15) and (27) to (31), wherein sugar chain modification is regulated in order to enhance antibody-dependent cellular cytotoxicity.

(33) A pharmaceutical composition comprising at least one of the antibodies according to the above (1) to (15) and (27) to (32).

(34) The pharmaceutical composition according to the above (33), which is for use in tumor therapy.

(35) The pharmaceutical composition according to the above (34), wherein the tumor is a cancer.

(36) The pharmaceutical composition according to the above (35), wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

(37) A method for treating a tumor, which comprises administering at least one of the antibodies according to the above (1) to (15) and (27) to (32) to an individual.

(38) The treatment method according to the above (37), wherein the tumor is a cancer.

(39) The treatment method according to the above (38), wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

Advantageous Effects of Invention

According to the present invention, there can be obtained a therapeutic agent for cancer comprising an antibody binding to GARP and having an antitumor activity caused by ADCC-mediated inhibition of Treg. In addition, the excessive presence and the activation of Treg in patients having malaria and HIV infection exhibit a correlation with that disease state, and the removal of Treg induces remission of the disease state in murine models for the diseases. Accordingly, it can be expected that effective inhibition of Treg function will have therapeutic effects also on refractory infectious diseases such as those caused by malaria and HIV.

BRIEF DESCRIPTION OF DRAWINGS

FIG. 1 shows the amino acid sequence (SEQ ID NO: 1) of GARP.

FIG. 2 shows the amino acid sequence (SEQ ID NO: 2) of a 105F antibody heavy chain.

FIG. 3 shows the amino acid sequence (SEQ ID NO: 3) of a 105F antibody light chain.

FIG. 4 shows the amino acid sequence (SEQ ID NO: 4) of a 110F antibody heavy chain.

FIG. 5 shows the amino acid sequence (SEQ ID NO: 5) of a 110F antibody light chain.

FIG. 6 shows the nucleotide sequence (SEQ ID NO: 6) of a 105F antibody heavy chain.

FIG. 7 shows the nucleotide sequence (SEQ ID NO: 7) of a 105F antibody light chain.

FIG. 8 shows the nucleotide sequence (SEQ ID NO: 8) of a 110F antibody heavy chain.

FIG. 9 shows the nucleotide sequence (SEQ ID NO: 9) of a 110F antibody light chain.

FIG. 10 shows the binding of antibodies to GARP. The 105F antibody and the 110F antibody exhibited the binding thereof to GARP according to an ELISA method.

FIG. 11 shows the specific binding of antibodies to GARP. The 105F antibody did not bind to HEK293T cells, into which an empty vector had been introduced, and exhibited the binding thereof to HEK293T cells, in which GARP had been transiently expressed.

FIG. 12 shows the specific binding of an antibody to GARP. The 105F antibody exhibited a binding activity to L428 cells endogenously expressing GARP.

FIG. 13 shows the specific binding of antibodies to GARP. The 105F antibody exhibited a binding activity to activated Treg.

FIG. 14 shows the ADCC activity of antibodies. When L428 cells endogenously expressing GARP were targeted, an increase in the ADCC activity was found in a 105F antibody concentration-dependent manner.

FIG. 15 shows the inhibitory activity of an antibody to the Treg function. The 105F antibody (50 μg/mL) inhibited the proliferation-suppressive function of Treg against helper T cells.

FIG. 16 shows the inhibitory activity of antibody to the Treg function. The 105F antibody (10 μg/mL) inhibited the proliferation-suppressive function of Treg against helper T cells. On the other hand, the MHG-8 and LHG-10 antibodies did not exhibit the effect on the proliferation-suppressive function of Treg against helper T cells.

FIG. 17 shows the amino acid sequence (SEQ ID NO: 25) of a c151D antibody heavy chain.

FIG. 18 shows the amino acid sequence (SEQ ID NO: 27) of a c151D antibody light chain.

FIG. 19 shows the amino acid sequence (SEQ ID NO: 29) of a c198D antibody heavy chain.

FIG. 20 shows the amino acid sequence (SEQ ID NO: 31) of a c198D antibody light chain.

FIG. 21 shows the amino acid sequence (SEQ ID NO: 33) of an h151D-H1 heavy chain.

FIG. 22 shows the amino acid sequence (SEQ ID NO: 37) of an h151D-L1 light chain.

FIG. 23 shows the amino acid sequence (SEQ ID NO: 35) of an h151D-H4 heavy chain.

FIG. 24 shows the amino acid sequence (SEQ ID NO: 39) of an h151D-L4 light chain.

FIG. 25 shows the amino acid sequence (SEQ ID NO: 41) of an h198D-H3 heavy chain.

FIG. 26 shows the amino acid sequence (SEQ ID NO: 43) of an h198D-L4 light chain.

FIG. 27 shows the nucleotide sequence (SEQ ID NO: 24) of a c151D antibody heavy chain.

FIG. 28 shows the nucleotide sequence (SEQ ID NO: 26) of a c151D antibody light chain.

FIG. 29 shows the nucleotide sequence (SEQ ID NO: 28) of a c198D antibody heavy chain.

FIG. 30 shows the nucleotide sequence (SEQ ID NO: 30) of a c198D antibody light chain.

FIG. 31 shows the nucleotide sequence (SEQ ID NO: 32) of a h151D-H1 antibody heavy chain.

FIG. 32 shows the nucleotide sequence (SEQ ID NO: 36) of a h151D-L1 antibody heavy chain.

FIG. 33 shows the nucleotide sequence (SEQ ID NO: 34) of an h151D-H4 heavy chain.

FIG. 34 shows the nucleotide sequence (SEQ ID NO: 38) of an h151D-L4 light chain.

FIG. 35 shows the nucleotide sequence (SEQ ID NO: 40) of an h198D-H3 heavy chain.

FIG. 36 shows the nucleotide sequence (SEQ ID NO: 42) of an h198D-L4 light chain.

FIG. 37 shows the binding activity of each antibody to GARP-expressing cells. h151D-H1L1, h151D-H4L4 and h198D-H3L4 exhibited a specific binding activity to GARP.

FIG. 38 shows the binding activity of each antibody to GARP-TGF β1 co-expressing cells. Individual antibodies 105F, h151D-H1L1, h151D-H4L4 and h198D-H3L4 bound to both GARP and a GARP mutant, which were co-expressed with TGFβ1, and these antibodies exhibited a binding activity to a different region in GARP from the case of known antibodies MHG8 and LHG10.

FIG. 39 shows the binding activity of each antibody to L428 cells. Individual antibodies h151D-H1L1, h151D-H4L4 and h198D-H3L4 exhibited a binding activity to endogenously expressed GARP.

FIG. 40 shows the binding activity of each antibody to Treg. Individual antibodies h151D-H1L1, h151D-H4L4 and h198D-H3L4 exhibited a binding activity to FoxP3-positive Treg.

FIG. 41 shows the ADCC activity of each antibody. Individual antibodies h151D-H1L1, h151D-H4L4 and h198D-H3L4 exhibited an ADCC activity.

FIG. 42 shows inhibitory activity of each antibody to the Treg function. Individual antibodies h151D-H1L1, h151D-H4L4 and h198D-H3L4 exhibited inhibitory activity to the Treg function.

FIG. 43 shows suppressive activity of Treg on the target cell lysis activity of CTL.

FIG. 44 shows an increase in antitumor activity of each antibody. Individual antibodies 105F, h151D-H1L1, h151D-H4L4, and h198D-H3L4 inhibited the suppressive function of Treg on cell lysis activity of CTL.

FIG. 45 shows the in vivo antitumor activity of each antibody. Individual antibodies 105F, h151D-H1L1, h151D-H4L4, and h198D-H3L4 exhibited an antitumor activity in in vivo models.

DESCRIPTION OF EMBODIMENTS

In the present description, the term "cancer" is used to have the same meaning as that of the term "tumor".

In the present description, the term "gene" is used to include, not only DNA but also its mRNA and cDNA, and the cRNA thereof.

In the present description, the term "polynucleotide" is used to have the same meaning as that of a nucleic acid, and it includes DNA, RNA, a probe, an oligonucleotide, and a primer.

In the present description, the term "polypeptide" is used such that it is not distinguished from the term "protein."

In the present description, the term "cell" includes cells in an individual animal, and cultured cells.

In the present description, the term "GARP" is used to have the same meaning as that of GARP protein.

In the present description, the term "cytotoxicity" is used to mean that a pathologic change is caused to cells in any given way. It does not only mean a direct trauma, but also means all types of structural or functional damage caused to cells, such as DNA cleavage, formation of a base dimer, chromosomal cleavage, damage to cell mitotic apparatus, and a reduction in the activities of various types of enzymes.

In the present description, the term "cytotoxic activity" is used to mean an activity that causes the above described cytotoxicity.

In the present description, the term "antibody-dependent cellular cytotoxicity" is used to mean an "antibody dependent cellular cytotoxic (ADCC) activity," and this activity means the effect or the activity of damaging target cells such as tumor cells by NK cells mediated by an antibody.

In the present description, the term "epitope" is used to mean the partial peptide or partial three-dimensional structure of GARP, to which a specific anti-GARP antibody binds. Such an epitope, which is a partial peptide of the above described GARP, can be determined by a method well known to a person skilled in the art, such as an immunoassay, for example, by the following method. First, various partial structures of an antigen are produced. As regards production of such partial structures, a known oligopeptide synthesis technique can be applied. For example, a series of peptides, in which an antigen has been successively truncated at an appropriate length from the C-terminus or N-terminus thereof, are produced by a genetic recombination technique well known to a person skilled in the art, and thereafter, the reactivity of an antibody to such polypeptides is studied, and recognition sites are roughly determined. Thereafter, further shorter peptides are synthesized, and the reactivity thereof to the aforementioned peptides is then studied, so as to determine an epitope. Moreover, an epitope, which is a partial three-dimensional structure of an antigen that binds to a specific antibody, can be determined by specifying the amino acid residues of an antigen adjacent to the above-described antibody by X-ray structural analysis.

In the present description, the phrase "antibodies binding to the same epitope" is used to mean different antibodies that bind to a common epitope. If a second antibody binds to a partial peptide or a partial three-dimensional structure, to which a first antibody binds, it can be determined that the first antibody and the second antibody bind to the same epitope. In addition, by confirming that a second antibody competes with a first antibody for the binding of a first antibody to an antigen (i.e., a second antibody interferes with the binding of a first antibody to an antigen), it can be determined that the first antibody and the second antibody bind to the same epitope, even if the specific sequence or structure of the epitope has not been determined. Furthermore, when a first antibody and a second antibody bind to the same epitope and further, the first antibody has special effects such as antitumor activity, the second antibody can be expected to have the same activity as that of the first antibody. Accordingly, if a second anti-GARP antibody binds to a partial peptide to which a first anti-GARP antibody binds, it can be determined that the first antibody and the second antibody bind to the same epitope of GARP. In addition, by confirming that the second anti-GARP antibody competes with the first anti-GARP antibody for the binding of the first anti-GARP antibody to GARP, it can be determined that the first antibody and the second antibody are antibodies binding to the same epitope of GARP.

In the present description, the term "CDR" is used to mean a complementarity determining region. It is known that the heavy chain and light chain of an antibody molecule each have three CDRs. Such a CDR is also referred to as a hypervariable domain, and is located in the variable region of the heavy chain and light chain of an antibody. These regions have a particularly highly variable primary structure and are separated into three sites on the primary structure of the polypeptide chain in each of the heavy chain and light chain. In the present description, with regard to the CDR of an antibody, the CDRs of a heavy chain are referred to as CDRH1, CDRH2 and CDRH3, respectively, from the amino-terminal side of the amino acid sequence of the heavy chain, whereas the CDRs of a light chain are referred to as CDRL1, CDRL2 and CDRL3, respectively, from the amino-terminal side of the amino acid sequence of the light chain. These sites are located close to one another on the three-dimensional structure, and determine the specificity of the antibody to an antigen, to which the antibody binds.

In the present invention, the phrase "to hybridize under stringent conditions" is used to mean that hybridization is carried out in the commercially available hybridization solution ExpressHyb Hybridization Solution (manufactured by Clontech) at 68° C., or that hybridization is carried out under conditions in which hybridization is carried out using a DNA-immobilized filter in the presence of 0.7-1.0 M NaCl at 68° C., and the resultant is then washed at 68° C. with a 0.1- to 2-fold concentration of SSC solution (wherein 1×SSC consists of 150 mM NaCl and 15 mM sodium citrate) for identification, or conditions equivalent thereto.

1. GARP

GARP used in the present invention can be directly purified from the GARP-expressing cells of a human or a non-human mammal (e.g., a rat, a mouse, etc.) and can then be used, or a cell membrane faction of the aforementioned cells can be prepared and can be used as the GARP. Alternatively, GARP can also be obtained by synthesizing it in vitro, or by allowing host cells to produce GARP by genetic manipulation. According to such genetic manipulation, the GARP protein can be obtained, specifically, by incorporating GARP cDNA into an expression vector capable of expressing the GARP cDNA, and then synthesizing GARP in a solution comprising enzymes, substrate and energetic materials necessary for transcription and translation, or by transforming the host cells of other prokaryotes or eukaryotes, so as to allow them to express GARP.

The amino acid sequence of human GARP is shown in SEQ ID NO: 1 in the sequence listing. In addition, the sequence of SEQ ID NO: 1 is shown in FIG. 1.

Moreover, a protein, which consists of an amino acid sequence comprising a substitution, deletion and/or addition of one or several amino acids in the above-described amino acid sequence of GARP, and has a biological activity equivalent to that of the GARP protein, is also included in GARP.

Mature human GARP, from which a signal sequence has been removed, corresponds to an amino acid sequence consisting of the amino acid residues at positions 20 to 662 in the amino acid sequence shown in SEQ ID NO: 1.

Furthermore, a protein, which consists of an amino acid sequence comprising a substitution, deletion and/or addition of one or several amino acids in the amino acid sequence shown in SEQ ID NO: 1, or in the amino acid sequence shown in SEQ ID NO: 1 from which a signal sequence has been removed, and which has a biological activity equivalent to that of GARP, is also included in GARP. Further, a protein, which consists of an amino acid sequence encoded by a splicing variant transcribed from a human GARP gene locus or an amino acid sequence comprising a substitution, deletion and/or addition of one or several amino acids in the aforementioned amino acid sequence, and which has a biological activity equivalent to that of GARP, is also included in GARP.

2. Production of Anti-GARP Antibody

An example of the antibody against GARP of the present invention can be an anti-GARP human antibody. The anti-GARP human antibody means a human antibody having only the gene sequence of an antibody derived from human chromosomes.

The anti-GARP human antibody can be obtained by a method using a human antibody-producing mouse having a human chromosomal fragment comprising the heavy chain and light chain genes of a human antibody (see Tomizuka, K. et al., Nature Genetics (1997) 16, p. 133-143,; Kuroiwa, Y. et al., Nucl. Acids Res. (1998) 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999.; Tomizuka, K. et al., Proc. Natl. Acad. Sci. USA (2000) 97, p. 722-727; etc.).

Such a human antibody-producing mouse can be specifically produced by using a genetically modified animal, the gene loci of endogenous immunoglobulin heavy chain and light chain of which have been disrupted and instead the gene loci of human immunoglobulin heavy chain and light chain have been then introduced using a yeast artificial chromosome (YAC) vector or the like, and then producing a knock-out animal and a transgenic animal from such a genetically modified animal, and then breeding such animals with one another.

Otherwise, the anti-GARP human antibody can also be obtained by transforming eukaryotic cells with cDNA encoding each of the heavy chain and light chain of such a human antibody, or preferably with a vector comprising the cDNA, according to genetic recombination techniques, and then culturing the transformed cells producing a genetically modified human monoclonal antibody, so that the antibody can be obtained from the culture supernatant. As host cells, eukaryotic cells, and preferably, mammalian cells such as CHO cells, lymphocytes or myelomas can, for example, be used.

Alternatively, the antibody can also be obtained by a method of obtaining a phage display-derived human antibody that has been selected from a human antibody library (see Wormstone, I. M. et al., Investigative Ophthalmology & Visual Science. (2002) 43 (7), p. 2301-2308; Carmen, S. et al., Briefings in Functional Genomics and Proteomics (2002), 1 (2), p. 189-203; Siriwardena, D. et al., Ophthalmology (2002) 109 (3), p. 427-431; etc.). For example, a phage display method, which comprises allowing the variable region of a human antibody to express as a single chain antibody (scFv) on the surface of a phage, and then selecting a phage binding to an antigen, can be applied (Nature Biotechnology (2005), 23, (9), p. 1105-1116).

By analyzing the phage gene that has been selected because of its binding ability to the antigen, a DNA sequence encoding the variable region of a human antibody binding to the antigen can be determined. Once the DNA sequence of scFv binding to the antigen is determined, a DNA sequence of a constant region of an antibody is allowed to bind thereto to produce an IgG expression vector having the aforementioned sequences, and the produced expression vector is then introduced into suitable host cells and is allowed to express therein, thereby obtaining a human antibody (WO92/01047, WO92/20791, WO93/06213, WO93/11236, WO93/19172, WO95/01438, WO95/15388, Annu. Rev. Immunol (1994) 12, p. 433-455, Nature Biotechnology (2005) 23 (9), p. 1105-1116).

Moreover, the antibody against GARP of the present invention can be obtained by immunizing an animal with GARP or any given polypeptide selected from the amino acid sequence of GARP, and then collecting and purifying an antibody produced in a living body thereof. The species of the organism of the GARP used as an antigen is not limited to human, and thus, an animal can also be immunized with GARP derived from an animal other than a human, such as a mouse or a rat. In this case, an antibody applicable to the disease of a human can be selected by examining the cross-reactivity of the obtained antibody binding to heterologous GARP with human GARP.

Furthermore, antibody-producing cells that produce an antibody against GARP are fused with myeloma cells according to a known method (e.g., Kohler and Milstein, Nature (1975) 256, p. 495-497, Kennet, R. ed., Monoclonal Antibodies, p. 365-367, Plenum Press, N. Y. (1980)) to establish hybridomas, so as to obtain a monoclonal antibody.

It is to be noted that GARP used as an antigen can be obtained by allowing host cells to produce GARP genes according to genetic manipulation.

Specifically, a vector capable of expressing a GARP gene is produced, and the vector is then introduced into host cells, so that the gene is expressed therein, and thereafter, the expressed GARP may be purified. Hereafter, a method of obtaining an antibody against GARP will be specifically described.

(1) Preparation of Antigen

Examples of an antigen used to produce an anti-GARP antibody can include GARP, a polypeptide consisting of at least 6 consecutive partial amino acid sequences thereof, and a derivative prepared by adding any given amino acid sequence or carrier to such GARP or a polypeptide thereof.

GARP can be directly purified from the tumor tissues or tumor cells of a human and can then be used. Alternatively, GARP can also be obtained by synthesizing it in vitro or by allowing host cells to produce it by genetic manipulation.

According to such genetic manipulation, an antigen can be obtained, specifically, by incorporating GARP cDNA into an expression vector capable of expressing the GARP cDNA, and then synthesizing GARP in a solution comprising enzymes, substrate and energetic materials necessary for transcription and translation, or by transforming the host cells of other prokaryotes or eukaryotes, so as to allow them to express GARP.

It is also possible to obtain an antigen as a secretory protein by allowing a fusion protein formed by ligating DNA encoding the extracellular region of GARP as a membrane protein to DNA encoding the constant region of an antibody, to express in a suitable host and/or vector system.

GARP cDNA can be obtained by what is called a PCR method, which comprises performing a polymerase chain reaction (hereinafter referred to as "PCR"), for example, using a cDNA library expressing the cDNA of GARP as a template, and also using primers for specifically amplifying the GARP cDNA (see Saiki, R. K., et al. Science (1988) 239, p. 487-489).

An example of the in vitro synthesis of a polypeptide can be the Rapid Translation System (RTS) manufactured by Roche Diagnostics, but it is not limited thereto.

Examples of prokaryotic cells used as host cells can include *Escherichia coli* and *Bacillus subtilis*. In order to transform the host cells with a gene of interest, the host cells are transformed with a plasmid vector comprising a replicon derived from species compatible with the host, namely, a replication origin, and a regulatory sequence. As a vector, a vector having a sequence capable of imparting the selectivity of a phenotype to the cells to be transformed is preferable.

Examples of eukaryotic cells used as host cells can include the cells of vertebrate, insects and yeasts. Examples of the vertebrate cells that can frequently be used include COS cells which are monkey cells (Gluzman, Y., Cell (1981) 23, p. 175-182, ATCC CRL-1650), mouse fibroblasts NIH3T3 (ATCC No. CRL-1658), and a dihydrofolate reductase-deficient cell line of Chinese hamster ovary cells (CHO cells, ATCC CCL-61) (Urlaub, G. and Chasin, L. A. Proc. Natl. Acad. Sci. U.S.A. (1980) 77, p. 4126-4220), but are not limited thereto.

The thus obtained transformant can be cultured according to ordinary methods, and a polypeptide of interest can be produced inside or outside of the cells of the culture.

As media used in the culture, various types of commonly used media can be selected, as appropriate, depending on the type of the adopted host cells. If the host cells are *Escherichia coli*, for example, antibiotics such as ampicillin or IPMG can be added to an LB medium, as necessary, and the resulting medium can then be used.

A recombinant protein produced inside or outside of the cells of a transformant as a result of the above described culture can be separated and/or purified by various types of known separation methods, utilizing the physical properties or chemical properties of the protein.

Specific examples of the method can include a treatment using an ordinary protein precipitant, ultrafiltration, various types of liquid chromatography such as molecular sieve chromatography (gel filtration), absorption chromatography, ion exchange chromatography or affinity chromatography, a dialysis method, and a combination thereof.

In addition, by attaching a histidine tag consisting of 6 residues to a recombinant protein to be expressed, the protein can be efficiently purified using a nickel affinity column. Otherwise, by connecting the Fc region of IgG to a recombinant protein to be expressed, the protein can be efficiently purified using a Protein A column.

By combining the above described methods with one another, a polypeptide of interest can be produced at a large scale, with a high yield and with high purity.

(2) Production of Anti-GARP Monoclonal Antibody

An example of an antibody specifically binding to GARP can be a monoclonal antibody specifically binding to GARP. A method of obtaining such a monoclonal antibody is as follows.

For the production of a monoclonal antibody, the following working steps are generally necessary.

Specifically, the necessary working steps include:
(a) purification of a biopolymer used as an antigen,
(b) a step of immunizing an animal with the antigen by injection, collecting the blood from the animal, examining the antibody titer to determine the period for excision of the spleen from the animal, and then preparing antibody-producing cells,
(c) preparation of myeloma cells (hereinafter referred to as "myelomas"),
(d) cell fusion between the antibody-producing cells and the myelomas,
(e) selection of a hybridoma group producing an antibody of interest,
(f) division into single cell clones (cloning),
(g) optionally, the culture of hybridomas for the mass production of monoclonal antibodies, or the breeding of animals into which the hybridomas are transplanted, and
(h) the analysis of the physiological activity and binding specificity of the thus produced monoclonal antibody, or examination of the properties of the antibody as a labelling reagent.

Hereafter, a method for producing a monoclonal antibody will be described in detail along with the above described steps. However, the method of producing the aforementioned antibody is not limited thereto, and, for example, antibody-producing cells other than splenic cells and myelomas can also be used.

(a) Purification of Antigen

As an antigen, GARP prepared by the above described method, or a portion thereof, can be used.

Alternatively, a membrane fraction prepared from GARP-expressing recombinant somatic cells, or such GARP-expressing recombinant somatic cells themselves, or further, a partial peptide of the protein of the present invention, which is chemically synthesized according to a method well known to a person skilled in the art, can also be used as an antigen.

(b) Preparation of Antibody-Producing Cells

The antigen obtained in step (a) is mixed with an auxiliary agent, such as a Freund complete or incomplete adjuvant, or potassium alum, to prepare an immunogen, and thereafter, an experimental animal is immunized with the immunogen. As such an experimental animal, an animal used in known methods for producing hybridomas can be used without any problems. Specific examples of such an animal that can be used herein include a mouse, a rat, a goat, sheep, a bovine, and a horse. From the viewpoint of the availability of myeloma cells to be fused with the excised antibody-producing cells, etc., a mouse or a rat is preferably used as the animal to be immunized.

The strains of actually used mice and rats are not particularly limited. In the case of mice, examples of the strain that can be used herein include A, AKR, BALB/c, BDP, BA, CE, C3H, 57BL, C57BL, C57L, DBA, FL, HTH, HT1, LP, NZB, NZW, RF, R III, SJL, SWR, WB, and 129. On the other hand, in the case of rats, examples of the strain that can be used herein include Wistar, Low, Lewis, Sprague Dawley, ACI, BN, and Fischer.

These mice and rats are available from experimental animal breeders and distributors, such as CLEA Japan, Inc. and CHARLES RIVER LABORATORIES JAPAN, INC.

Among others, taking into consideration fusion compatibility with the myeloma cells discussed below, the BALB/c strain in the case of mice, and the Wistar and Low strains in the case of rats, are particularly preferable as animals to be immunized.

Moreover, taking into consideration the homology between the antigens of humans and mice, it is also preferable to use mice whose biological mechanism for removing autoantibodies has been reduced, namely, autoimmune disease mice.

The age of these mice or rats upon immunization is preferably 5 to 12 weeks old, and more preferably 6 to 8 weeks old.

In order to immunize animals with GARP or a recombinant thereof, known methods, which are described in detail, for example, in Weir, D. M., Handbook of Experimental Immunology, Vol. I. II. III., Blackwell Scientific Publications, Oxford (1987), Kabat, E. A. and Mayer, M. M., Experimental Immunochemistry, Charles C Thomas Publisher Springfield, Illinois (1964), etc. can be applied.

Among these immunization methods, a method preferably applied in the present invention is specifically the following method, for example.

That is to say, first, cells, in which a membrane protein fraction used as an antigen, or an antigen has been expressed, are intradermally or intraperitoneally administered to an animal.

In order to enhance immunization efficiency, the combined use thereof is preferable. If intradermal administration is carried out in a first half of an administration regime, and intraperitoneal administration is carried out in a latter half thereof or only in the final instance of administration, immunization efficiency can be particularly enhanced.

The administration schedule of the antigen is different depending on the type of animal to be immunized, individual differences, etc. In general, 3 to 6 antigen doses and a dosing interval of 2 to 6 weeks are preferable, and 3 or 4 antigen doses and a dosing interval of 2 to 4 weeks are more preferable.

The applied dose of an antigen is different depending on the type of animal to be immunized, individual differences, etc. It is generally 0.05 to 5 mg, and preferably approximately 0.1 to 0.5 mg.

The booster is carried out 1 to 6 weeks, preferably 2 to 4 weeks, and more preferably 2 to 3 weeks, after the above described administration of the antigen.

The applied dose of the antigen, when the booster is carried out, is different depending on the type of animal, the size thereof, etc. In the case of a mouse for example, the applied dose of the antigen is generally 0.05 to 5 mg, preferably 0.1 to 0.5 mg, and more preferably approximately 0.1 to 0.2 mg.

1 to 10 days, preferably 2 to 5 days, and more preferably 2 or 3 days after completion of the above described booster, splenic cells or lymphocytes comprising antibody-producing cells are aseptically removed from the immunized animal. At that time, the antibody titer is measured. An animal, in which the antibody titer has been sufficiently increased, is used as a supply source of antibody-producing cells, so that the efficiency of the subsequent operations can be enhanced.

Examples of the method of measuring an antibody titer used herein can include a RIA method and an ELISA method, but are not limited thereto.

With regard to the measurement of an antibody titer in the present invention, the ELISA method can, for example, be carried out according to the following procedures.

First, a purified or a partially purified antigen is adsorbed on the surface of a solid phase, such as a 96-well plate for ELISA, and another solid surface, on which such an antigen is not adsorbed, is covered with a protein irrelevant to the antigen, such as bovine serum albumin (hereinafter referred to as "BSA"). The surfaces are washed, and are then allowed to come into contact with a serially diluted sample used as a primary antibody (e.g., mouse serum), so that an antibody in the sample is allowed to bind to the above described antigen.

Thereafter, an enzyme-labeled antibody against the mouse antibody is added as a secondary antibody, so that it is allowed to bind to the mouse antibody, followed by washing. After that, a substrate of the enzyme is added thereto, and a change in the absorbance due to color development based on the substrate decomposition, etc., is then measured, so that the antibody titer is calculated.

Antibody-producing cells can be separated from the splenic cells or lymphocytes of the immunized animal according to known methods (e.g., Kohler et al., Nature (1975) 256, p. 495,; Kohler et al., Eur. J. Immunol. (1977) 6, p. 511,; Milstein et al., Nature (1977), 266, p. 550,; Walsh, Nature, (1977) 266, p. 495). For example, in the case of splenic cells, there can be adopted a common method which comprises mincing the spleen, then filtrating the cells through a stainless steel mesh, then suspending the filtrate in Eagle's minimal essential medium (MEM) to separate antibody-producing cells.

(c) Preparation of Myeloma Cells (Hereinafter Referred to as "Myelomas")

Myeloma cells used in cell fusion are not particularly limited, and the cells can be selected from known cell lines, as appropriate, and can then be used. Taking into consideration issues of convenience in the selection of hybridomas from fused cells, HGPRT (Hypoxanthine-GUANINE phosphoribosyl transferase)-deficient cell lines, the selection procedures of which have been established, is preferably used.

That is, examples of such HGPRT-deficient cell lines include: mouse-derived X63-Ag8 (X63), NS1-ANS/1 (NS1), P3X63-Ag8. U1 (P3U1), X63-Ag8.653 (X63.653), SP2/0-Ag14 (SP2/0), MPC11-45.6TG1.7 (45.6TG), FO, S149/5XXO, and BU. 1; rat-derived 210. RSY3. Ag. 1. 2.3 (Y3); and human-derived U266AR (SKO-007), GM1500-GTG-A12 (GM1500), UC729-6, LICR-LOW-HMy2 (HMy2), and 8226AR/NIP4-1 (NP41). These HGPRT-deficient cell lines are available from, for example, American Type Culture Collection (ATCC).

These cell lines are sub-cultured in a suitable medium, such as an 8-azaguanine medium [a medium prepared by adding 8-azaguanine to an RPMI-1640 medium comprising glutamine, 2-mercaptoethanol, gentamicin, and fetal calf serum (hereinafter referred to as "FCS")], Iscove's Modified Dulbecco's Medium (hereinafter referred to as "IMDM"), or Dulbecco's Modified Eagle Medium (hereinafter referred to as "DMEM"). Three or four days before cell fusion, the cells are sub-cultured in a normal medium [e.g., ASF104 medium comprising 10% FCS (manufactured by Ajinomoto Co., Inc.)] to ensure not less than $2 \times 10^7$ cells on the day of cell fusion.

(d) Cell Fusion

Antibody-producing cells can be fused with myeloma cells, as appropriate, according to known methods (Weir, D. M., Handbook of Experimental Immunology, Vol. I. II. III., Blackwell Scientific Publications, Oxford (1987), Kabat, E. A. and Mayer, M. M., Experimental Immunochemistry, Charles C Thomas Publisher Springfield, Illinois (1964), etc.) under conditions in which the survival rate of cells is not excessively reduced.

Examples of such a method that can be used herein include a chemical method comprising mixing antibody-producing cells with myeloma cells in a high-concentration polymer solution such as polyethylene glycol, and a physical method utilizing electric stimulation. Among these methods, a specific example of the above described chemical method is as follows.

That is, when polyethylene glycol is used as a high-concentration polymer solution, antibody-producing cells are mixed with myeloma cells in a polyethylene glycol solution with a molecular weight of 1500 to 6000, preferably 2000 to 4000, at a temperature of 30° C. to 40° C., preferably 35° C. to 38° C., and for 1 to 10 minutes, preferably for 5 to 8 minutes.

(e) Selection of Hybridoma Group

The method of selecting hybridomas obtained by the above described cell fusion is not particularly limited. In general, a HAT (hypoxanthine-aminopterin-thymidine) selection method (Kohler et al., Nature (1975) 256, p. 495; Milstein et al., Nature (1977) 266, p. 550) is applied.

This method is effective, when hybridomas are obtained using myeloma cells of an HGPRT-deficient cell line that cannot survive in aminopterin.

Specifically, unfused cells and hybridomas are cultured in a HAT medium, so that only the hybridomas that are resistant to aminopterin are allowed to remain and grow selectively.

(f) Division into Single Cell Clones (Cloning)

As hybridoma cloning methods, known methods such as a methyl cellulose method, a soft agarose method, or a limiting dilution method can, for example, be applied (see, for example, Barbara, B. M. and Stanley, M. S.: Selected Methods in Cellular Immunology, W. H. Freeman and Company, San Francisco (1980)). Among these methods, three-dimensional culture methods, such as a methyl cellulose method, are particularly preferable. For example, a hybridoma group formed by cell fusion is suspended in a methyl cellulose medium such as ClonaCell-HY Selection Medium D (manufactured by StemCell Technologies, #03804), and is then cultured. Thereafter, the formed hybridoma colonies are harvested, so that monoclonal hybridomas can be obtained. The harvested hybridoma colonies are each cultured, and the obtained hybridoma culture supernatant, in which a stable antibody titer is observed, is selected as a GARP monoclonal antibody-producing hybridoma strain.

Examples of the thus established hybridoma strain can include GARP hybridomas 151D and 198D. In the present description, an antibody produced by GARP hybridomas 151D and 198D is referred to as a "151D antibody" or "198D antibody," or it is simply referred to as "151D" or "198D."

The heavy chain variable region of the 151D antibody has the amino acid sequence shown in SEQ ID NO: 15 in the sequence listing. In addition, the light chain variable region of the 151D antibody has the amino acid sequence shown in SEQ ID NO: 17 in the sequence listing. It is to be noted that the amino acid sequence of the heavy chain variable region shown in SEQ ID NO: 15 in the sequence listing is encoded by the nucleotide sequence shown in SEQ ID NO: 14 in the sequence listing. It is also to be noted that the amino acid sequence of the light chain variable region shown in SEQ ID NO: 17 in the sequence listing is encoded by the nucleotide sequence shown in SEQ ID NO: 16 in the sequence listing.

The heavy chain variable region of the 198D antibody has the amino acid sequence shown in SEQ ID NO: 19 in the sequence listing. In addition, the light chain variable region of the 198D antibody has the amino acid sequence shown in SEQ ID NO: 21 in the sequence listing. It is to be noted that the amino acid sequence of the heavy chain variable region shown in SEQ ID NO: 19 in the sequence listing is encoded by the nucleotide sequence shown in SEQ ID NO: 18 in the sequence listing. It is also to be noted that the amino acid sequence of the light chain variable region shown in SEQ ID NO: 21 in the sequence listing is encoded by the nucleotide sequence shown in SEQ ID NO: 20 in the sequence listing.

(g) Preparation of Monoclonal Antibody by Culturing Hybridomas

The thus selected hybridomas are cultured, so that monoclonal antibodies can be efficiently obtained. Before performing the culture, it is desirable to screen for hybridomas that produce a monoclonal antibody of interest.

For this screening, known methods can be adopted.

The antibody titer can be measured in the present invention by, for example, the ELISA method described in the above section (b).

The hybridomas obtained by the aforementioned methods can be preserved in liquid nitrogen or in a freezer at a temperature of −80° C. or lower in the form of a frozen state.

After completion of the cloning, the hybridomas are cultured, while replacing the HT medium with a normal medium.

Mass culture is carried out by rotary culture or spinner culture, using a large culture bottle. A supernatant obtained from this mass culture is purified according to methods well known to a person skilled in the art, such as gel filtration, so as to obtain a monoclonal antibody specifically binding to the protein of the present invention.

Moreover, hybridomas are injected into the abdominal cavity of a mouse of the same strain (e.g., the above described BALB/c), or a Nu/Nu mouse, and the hybridomas are allowed to grow therein, so as to obtain ascites comprising a large amount of the monoclonal antibody of the present invention.

When the hybridomas are administered into the abdominal cavity of such a mouse, a larger amount of ascites can be obtained if mineral oil such as 2,6,10,14-tetramethylpentadecane (pristane) has previously been administered to the mouse (3 to 7 days before administration of the hybridomas).

For instance, suppose that an immunosuppressive agent has previously been administered into the abdominal cavity of a mouse of the same strain as the hybridomas, so that T cells are deactivated. Twenty days after the injection, $10^6$ to $10^7$ hybridomas and/or clonal cells are suspended in a medium comprising no serum (0.5 ml), and the suspension is then administered into the abdominal cavity. When the normal abdomen has swollen and ascites has gathered, the ascites is collected from the mouse. According to this method, a monoclonal antibody in a concentration that is about 100 times or more than in a culture solution can be obtained.

The monoclonal antibody obtained by the above described method can be purified, for example, by the method described in Weir, D. M.: Handbook of Experimental Immunology, Vol. I, II, III, Blackwell Scientific Publications, Oxford (1978).

The thus obtained monoclonal antibody has high antigen specificity to GARP.

(h) Assay of Monoclonal Antibody

The isotype and subtype of the obtained monoclonal antibody can be determined as follows.

First, examples of the assay method can include an ouchterlony method, an ELISA method, and a RIA method.

The Ouchterlony method is simple, but when the concentration of a monoclonal antibody is low, a concentration procedure is necessary.

On the other hand, when the ELISA method or the RIA method is used, a culture supernatant is directly reacted with an antigen-adsorbed solid phase, and an antibody corresponding to various immunoglobulin isotypes or subclasses is used as a secondary antibody, so that the isotype and subtype of the monoclonal antibody can be identified.

As a simpler method, a commercially available identification kit (e.g., Mouse Typer Kit; manufactured by BioRad), etc. can also be utilized.

Moreover, quantification of a protein can be carried out by a Folin Lowry method and a method of calculating the value from the absorbance at 280 nm [1.4 (OD 280)=1 mg/ml immunoglobulin].

Furthermore, also in a case where the steps (a) to (h) in the above (2) are carried out again and a monoclonal antibody is independently obtained separately, an antibody having properties equivalent to those of an 105F antibody, an 110F antibody, a 151D-derived antibody (humanized 151D antibody) and a 198D-derived antibody (humanized 198D antibody) can be obtained. An example of such an antibody can be an antibody binding to the same epitope, to which each of the above described antibodies binds. The 105F antibody recognizes the amino acid sequence portions at amino acid positions 366 to 377, 407 to 445, and 456 to 470 in the amino acid sequence (SEQ ID NO: 1) of GARP, and binds thereto; the 110F antibody recognizes the amino acid sequence portions at amino acid positions 54 to 112 and 366 to 392 in the amino acid sequence (SEQ ID NO: 1) of GARP, and binds thereto; the 151D-derived antibody (humanized 151D antibody) recognizes the amino acid sequence at amino acid positions 352 to 392 in the amino acid sequence (SEQ ID NO: 1) of GARP, and binds thereto; and the 198D-derived antibody (humanized 198D antibody) recognizes the amino acid sequence at amino acid positions 18 to 112 in the amino acid sequence (SEQ ID NO: 1) of GARP, and binds thereto. Accordingly, particular examples of the aforementioned epitope can include the aforementioned regions in the amino acid sequence of GARP.

If a newly prepared monoclonal antibody binds to a partial peptide or a partial three-dimensional structure to which the above described 105F antibody, etc. binds, it can be determined that the monoclonal antibody binds to the same epitope, to which the above described 105F antibody, etc. binds. Moreover, by confirming that the monoclonal antibody competes with the above described antibodies such as the 105F antibody in the binding of the antibodies to GARP (i.e., the monoclonal antibody interferes with the binding of the above described antibodies such as the 105F antibody to GARP), it can be determined that the monoclonal antibody binds to the same epitope, to which the above described 105F antibody, etc. binds, even if the specific sequence or structure of the epitope has not been determined. When it is confirmed that the monoclonal antibody binds to the same epitope to which the 105F antibody, etc. binds, then it is strongly expected that the monoclonal antibody should have properties equivalent to the above described antibodies such as the 105F antibody.

(3) Other Antibodies

The antibody of the present invention also includes genetically recombinant antibodies that have been artificially modified for the purpose of reducing heterogenetic antigenicity to humans, such as a chimeric antibody, a humanized antibody and the above described human antibodies, as well as the above described monoclonal antibody against GARP. These antibodies can be produced by known methods.

The obtained antibody can be purified to a homogenous state. For separation and purification of the antibody, separation and purification methods used for ordinary proteins may be used. For example, column chromatography, filtration, ultrafiltration, salting-out, dialysis, preparative polyacrylamide gel electrophoresis, isoelectric focusing, etc. are appropriately selected and combined with one another, so that the antibody can be separated and purified (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but examples of the separation and purification methods are not limited thereto.

Examples of the chromatography can include affinity chromatography, ion exchange chromatography, hydrophobic chromatography, gel filtration chromatography, reverse phase chromatography, and absorption chromatography.

These chromatographic techniques can be carried out using liquid chromatography such as HPLC or FPLC.

Examples of the column used in the affinity chromatography can include a Protein A column and a Protein G column. Examples of the column involving the use of Protein A can include Hyper D, POROS, and Sepharose F. F. (Pharmacia).

Also, using an antigen-immobilized carrier, an antibody can be purified by utilizing the binding activity of the antibody to the antigen.

The obtained antibodies are evaluated, in terms of their binding activity to the antigen, according to the method described in the Examples discussed below, etc., so that a preferred antibody can be selected.

The stability of an antibody can be used as an indicator for comparison of the properties of antibodies. A differential scanning calorimeter (DSC) is a device capable of promptly and exactly measuring a thermal denaturation midpoint (Tm) that is a good indicator for the relative structural stability of a protein. By using DSC to measure Tm values and making a comparison regarding the obtained values, differences in the thermal stability can be compared. It is known that the preservation stability of an antibody has a certain correlation with the thermal stability of the antibody (Lori Burton, et al., Pharmaceutical Development and Technology (2007) 12, pp. 265-273), and thus, a preferred antibody can be selected using thermal stability as an indicator. Examples of other indicators for selection of an antibody can include high yield in suitable host cells and low agglutination in an aqueous solution. For example, since an antibody with the highest yield does not always exhibit the highest thermal stability, it is necessary to select an antibody most suitable for administration to a human by comprehensively determining it based on the aforementioned indicators.

An example of the anti-GARP human antibody of the present invention can be an anti-GARP human antibody obtained by the above described phage display method, and preferred examples of the present anti-GARP human antibody can include a 105F antibody and a 110F antibody, each of which has the following structure.

The heavy chain of the 105F antibody has the amino acid sequence shown in SEQ ID NO: 2 in the sequence listing. In the heavy chain amino acid sequence shown in SEQ ID NO: 2 in the sequence listing, the amino acid sequence consisting of the amino acid residues at positions 1 to 118 is a variable region, whereas the amino acid sequence consisting of the amino acid residues at positions 119 to 448 is a constant region. In SEQ ID NO: 2 in the sequence listing, this variable region has CDRH1 consisting of the amino acid sequence at amino acid positions 26 to 35, CDRH2 consisting of the amino acid sequence at amino acid positions 50 to 66, and CDRH3 consisting of the amino acid sequence at amino acid positions 99 to 107. In addition, the sequence of SEQ ID NO: 2 is shown in FIG. 2.

The light chain of the 105F antibody has the amino acid sequence shown in SEQ ID NO: 3 in the sequence listing. In the light chain amino acid sequence shown in SEQ ID NO: 3 in the sequence listing, the amino acid sequence consisting of the amino acid residues at positions 1 to 112 is a variable region, whereas the amino acid sequence consisting of the amino acid residues at positions 113 to 217 is a constant region. In SEQ ID NO: 3 in the sequence listing, this variable region has CDRL1 consisting of the amino acid sequence at amino acid positions 23 to 36, CDRL2 consisting of the amino acid sequence at amino acid positions 52 to 58, and CDRL3 consisting of the amino acid sequence at amino acid positions 91 to 101. In addition, the sequence of SEQ ID NO: 3 is shown in FIG. 3.

The heavy chain of the 110F antibody has the amino acid sequence shown in SEQ ID NO: 4 in the sequence listing. In the heavy chain amino acid sequence shown in SEQ ID NO: 4 in the sequence listing, the amino acid sequence consisting of the amino acid residues at positions 1 to 123 is a variable region, whereas the amino acid sequence consisting of the amino acid residues at positions 124 to 453 is a constant region. In SEQ ID NO: 4 in the sequence listing, this variable region has CDRH1 consisting of the amino acid sequence at amino acid positions 26 to 35, CDRH2 consisting of the amino acid sequence at amino acid positions 50 to 66, and CDRH3 consisting of the amino acid sequence at amino acid positions 99 to 112. In addition, the sequence of SEQ ID NO: 4 is shown in FIG. 4.

The light chain of the 110F antibody has the amino acid sequence shown in SEQ ID NO: 5 in the sequence listing. In the light chain amino acid sequence shown in SEQ ID NO: 5 in the sequence listing, the amino acid sequence consisting of the amino acid residues at positions 1 to 111 is a variable region, whereas the amino acid sequence consisting of the amino acid residues at positions 112 to 216 is a constant region. In SEQ ID NO: 5 in the sequence listing, this variable region has CDRL1 consisting of the amino acid sequence at amino acid positions 23 to 36, CDRL2 consisting of the amino acid sequence at amino acid positions 52 to 58, and CDRL3 consisting of the amino acid sequence at amino acid positions 91 to 100. In addition, the sequence of SEQ ID NO: 5 is shown in FIG. 5.

The amino acid sequence of the 105F antibody heavy chain shown in SEQ ID NO: 2 in the sequence listing is encoded by the nucleotide sequence shown in SEQ ID NO: 6 in the sequence listing. The nucleotide sequence consisting of the nucleotides at nucleotide positions 1 to 354 in the nucleotide sequence shown in SEQ ID NO: 6 in the sequence listing encodes the heavy chain variable region of the 105F antibody, and the nucleotide sequence consisting of the nucleotides at nucleotide positions 355 to 1344 encodes the heavy chain constant region of the 105F antibody. As shown in SEQ ID NO: 6, the nucleotide sequence encoding the variable region has a polynucleotide consisting of the nucleotide sequence at nucleotide positions 76 to 105 encoding CDRH1, a polynucleotide consisting of the nucleotide sequence at nucleotide positions 148 to 198 encoding CDRH2, and a polynucleotide consisting of the nucleotide sequence at nucleotide positions 295 to 321 encoding CDRH3. In addition, the sequence of SEQ ID NO: 6 is shown in FIG. 6.

The amino acid sequence of the 105F antibody light chain shown in SEQ ID NO: 3 in the sequence listing is encoded by the nucleotide sequence shown in SEQ ID NO: 7 in the sequence listing. The nucleotide sequence consisting of the nucleotides at nucleotide positions 1 to 336 in the nucleotide sequence shown in SEQ ID NO: 7 in the sequence listing encodes the light chain variable region of the 105F antibody, and the nucleotide sequence consisting of the nucleotides at nucleotide positions 337 to 651 encodes the light chain constant region of the 105F antibody. As shown in SEQ ID NO: 7, the nucleotide sequence encoding the variable region has a polynucleotide consisting of the nucleotide sequence at nucleotide positions 67 to 108 encoding CDRL1, a polynucleotide consisting of the nucleotide sequence at nucleotide positions 154 to 174 encoding CDRL2, and a polynucleotide consisting of the nucleotide sequence at nucleotide positions 271 to 303 encoding CDRL3. In addition, the sequence of SEQ ID NO: 7 is shown in FIG. 7.

The amino acid sequence of the 110F antibody heavy chain shown in SEQ ID NO: 4 in the sequence listing is encoded by the nucleotide sequence shown in SEQ ID NO: 8 in the sequence listing. The nucleotide sequence consisting of the nucleotides at nucleotide positions 1 to 369 in the nucleotide sequence shown in SEQ ID NO: 8 in the sequence listing encodes the heavy chain variable region of the 110F antibody, and the nucleotide sequence consisting of the nucleotides at nucleotide positions 370 to 1359 encodes the heavy chain constant region of the 110F antibody. As shown in SEQ ID NO: 8, the nucleotide sequence encoding the variable region has a polynucleotide consisting of the nucleotide sequence at nucleotide positions 76 to 105 encoding CDRH1, a polynucleotide consisting of the nucleotide sequence at nucleotide positions 148 to 198 encoding CDRH2, and a polynucleotide consisting of the nucleotide sequence at nucleotide positions 295 to 336 encoding CDRH3. In addition, the sequence of SEQ ID NO: 8 is shown in FIG. 8.

The amino acid sequence of the 110F antibody light chain shown in SEQ ID NO: 5 in the sequence listing is encoded by the nucleotide sequence shown in SEQ ID NO: 9 in the sequence listing. The nucleotide sequence consisting of the nucleotides at nucleotide positions 1 to 333 in the nucleotide sequence shown in SEQ ID NO: 9 in the sequence listing encodes the light chain variable region of the 110F antibody, and the nucleotide sequence consisting of the nucleotides at nucleotide positions 334 to 648 encodes the light chain constant region of the 110F antibody. As shown in SEQ ID NO: 9, the nucleotide sequence encoding the variable region has a polynucleotide consisting of the nucleotide sequence at nucleotide positions 67 to 108 encoding CDRL1, a polynucleotide consisting of the nucleotide sequence at nucleotide positions 154 to 174 encoding CDRL2, and a polynucleotide consisting of the nucleotide sequence at nucleotide positions 271 to 300 encoding CDRL3. In addition, the sequence of SEQ ID NO: 9 is shown in FIG. 9.

With regard to the antibody of the present invention, in addition to the above described anti-GARP human antibody, even in a case where an antibody is independently obtained, separately, according to a method other than the above described method of obtaining an antibody, antibodies having cytotoxicity equivalent to that of the 105F antibody or the 110F antibody can be obtained. An example of such an antibody can be an antibody binding to the same epitope to which the 105F antibody or the 110F antibody binds.

If a newly produced human antibody binds to a partial peptide or a partial three-dimensional structure, to which the 105F antibody or the 110F antibody binds, it can be determined that the produced antibody binds to the same epitope, to which the 105F antibody or the 110F antibody binds. In addition, by confirming that the concerned antibody competes with the 105F antibody or the 110F antibody for the binding thereof to GARP (i.e., the concerned antibody interferes with the binding of the 105F antibody or the 110F antibody to GARP), it can be determined that the concerned antibody binds to the same epitope, to which the 105F antibody or the 110F antibody binds, even if the specific sequence or structure of the epitope has not been determined. If it is confirmed that the concerned antibody binds to the same epitope to which the 105F antibody or the 110F antibody binds, then it is strongly expected that the concerned antibody should have cytotoxicity equivalent to that of the 105F antibody or the 110F antibody.

Moreover, the antibody of the present invention includes artificially modified, genetically recombinant antibodies. These antibodies can be produced using known methods. The antibody concerned is preferably an antibody having, at least, the same 6 CDRs as the heavy chain and light chain of the above described 105F antibody or 110F antibody, and also having ADCC activity and inhibitory activity on the immunosuppressive function of Treg. The concerned antibody is not limited to a specific antibody, as long as it has the aforementioned properties. The antibody is more preferably an antibody having the heavy chain variable region and light chain variable region of the above described 105F antibody or 110F antibody.

Furthermore, by combining sequences showing a high homology to the heavy chain amino acid sequence and light chain amino acid sequence of the 105F antibody or the 110F antibody with each other, it is possible to select an antibody having an activity equivalent to the above described antibody. Such a homology is a homology of generally 80% or more, preferably 90% or more, more preferably 95% or more, and most preferably 99% or more (however, each CDR is identical to that of each of the above described antibodies). Further, it is also possible to select an antibody having an activity equivalent to each of the above described antibodies by incorporating an amino acid sequence comprising a substitution, deletion or addition of one or several amino acid residues to the amino acid sequence of the above described heavy chain or light chain (excluding each CDR site).

Still further, examples of the anti-GARP antibody according to the present invention can include the following chimeric antibodies and humanized antibodies.

Example of a chimeric antibody can include antibodies in which a variable region and a constant region are heterologous to each other, such as a chimeric antibody formed by conjugating the variable region of a mouse- or rat-derived antibody to a human-derived constant region (see Proc. Natl. Acad. Sci. U. S. A., 81, 6851-6855, (1984)).

A chimeric antibody derived from rat anti-human GARP antibody 151D is an antibody consisting of a heavy chain comprising a heavy chain variable region consisting of the amino acid sequence consisting of the amino acid residues at positions 1 to 117 shown in SEQ ID NO: 15, and a light chain comprising a light chain variable region consisting of the amino acid sequence consisting of the amino acid residues at positions 1 to 109 shown in SEQ ID NO: 17, and this chimeric antibody may have a constant region derived from any given human.

Moreover, a chimeric antibody derived from a rat anti-human GARP antibody 198D is an antibody consisting of a heavy chain comprising a heavy chain variable region consisting of the amino acid sequence consisting of the amino acid residues at positions 1 to 120 shown in SEQ ID NO: 19, and a light chain comprising a light chain variable region consisting of the amino acid sequence consisting of the amino acid residues at positions 1 to 109 shown in SEQ ID NO: 21, and this chimeric antibody may have a constant region derived from any given human.

Examples of such a chimeric antibody can include: an antibody consisting of a heavy chain having the amino acid sequence consisting of the amino acid residues at positions 20 to 466 shown in SEQ ID NO: 25 in the sequence listing, and a light chain having the amino acid sequence consisting of the amino acid residues at positions 21 to 234 shown in SEQ ID NO: 27 therein; and an antibody consisting of a heavy chain having the amino acid sequence consisting of the amino acid residues at positions 20 to 469 shown in SEQ ID NO: 29 in the sequence listing, and a light chain having the amino acid sequence consisting of the amino acid residues at positions 21 to 234 shown in SEQ ID NO: 31 therein.

It is to be noted that, in the heavy chain sequence shown in SEQ ID NO: 25 in the sequence listing, the amino acid sequence consisting of the amino acid residues at positions 1 to 19 is a signal sequence, the amino acid sequence consisting of the amino acid residues at positions 20 to 136 is a variable region, and the amino acid sequence consisting of the amino acid residues at positions 137 to 466 is a constant region.

It is also to be noted that, in the light chain sequence shown in SEQ ID NO: 27 in the sequence listing, the amino acid sequence consisting of the amino acid residues at positions 1 to 20 is a signal sequence, the amino acid sequence consisting of the amino acid residues at positions 21 to 129 is a variable region, and the amino acid sequence consisting of the amino acid residues at positions 130 to 234 is a constant region.

It is further to be noted that, in the heavy chain sequence shown in SEQ ID NO: 29 in the sequence listing, the amino acid sequence consisting of the amino acid residues at positions 1 to 19 is a signal sequence, the amino acid sequence consisting of the amino acid residues at positions 20 to 139 is a variable region, and the amino acid sequence consisting of the amino acid residues at positions 140 to 469 is a constant region.

It is further to be noted that, in the light chain sequence shown in SEQ ID NO: 31 in the sequence listing, the amino acid sequence consisting of the amino acid residues at positions 1 to 20 is a signal sequence, the amino acid sequence consisting of the amino acid residues at positions 21 to 129 is a variable region, and the amino acid sequence consisting of the amino acid residues at positions 130 to 234 is a constant region.

The amino acid sequence of the heavy chain of the c151D antibody shown in SEQ ID NO: 25 in the sequence listing is encoded by the nucleotide sequence shown in SEQ ID NO: 24 in the sequence listing. The nucleotide sequence consisting of the nucleotides at nucleotide positions 1 to 57 in the nucleotide sequence shown in SEQ ID NO: 24 in the sequence listing encodes the heavy chain signal sequence of the c151D antibody, the nucleotide sequence consisting of the nucleotides at nucleotide positions 58 to 408 therein encodes the heavy chain variable region of the c151D antibody, and the nucleotide sequence consisting of the nucleotides at nucleotide positions 409 to 1398 therein encodes the heavy chain constant region of the c151D antibody.

Moreover, the amino acid sequence of the light chain of the c151D antibody shown in SEQ ID NO: 27 in the sequence listing is encoded by the nucleotide sequence shown in SEQ ID NO: 26 in the sequence listing. The nucleotide sequence consisting of the nucleotides at nucleotide positions 1 to 60 in the nucleotide sequence shown in SEQ ID NO: 26 in the sequence listing encodes the light chain signal sequence of the c151D antibody, the nucleotide sequence consisting of the nucleotides at nucleotide positions 61 to 387 therein encodes the light chain variable region of the c151D antibody, and the nucleotide sequence consisting of the nucleotides at nucleotide positions 388 to 702 therein encodes the light chain constant region of the c151D antibody.

Furthermore, the amino acid sequence of the heavy chain of the c198D antibody shown in SEQ ID NO: 29 in the sequence listing is encoded by the nucleotide sequence shown in SEQ ID NO: 28 in the sequence listing. The nucleotide sequence consisting of the nucleotides at nucleotide positions 1 to 57 in the nucleotide sequence shown in SEQ ID NO: 28 in the sequence listing encodes the heavy chain signal sequence of the c198D antibody, the nucleotide sequence consisting of the nucleotides at nucleotide positions 58 to 417 therein encodes the heavy chain variable region of the c198D antibody, and the nucleotide sequence consisting of the nucleotides at nucleotide positions 418 to 1407 therein encodes the heavy chain constant region of the c198D antibody.

Further, the amino acid sequence of the light chain of the c198D antibody shown in SEQ ID NO: 31 in the sequence listing is encoded by the nucleotide sequence shown in SEQ ID NO: 30 in the sequence listing. The nucleotide sequence consisting of the nucleotides at nucleotide positions 1 to 60 in the nucleotide sequence shown in SEQ ID NO: 30 in the sequence listing encodes the light chain signal sequence of the c198D antibody, the nucleotide sequence consisting of the nucleotides at nucleotide positions 61 to 387 therein encodes the light chain variable region of the c198D antibody, and the nucleotide sequence consisting of the nucleotides at nucleotide positions 388 to 702 therein encodes the light chain constant region of the c198D antibody.

Examples of the humanized antibody include a humanized antibody formed by incorporating only a complementarity determining region (CDR) into a human-derived antibody (see Nature (1986) 321, p. 522-525), and a humanized antibody formed by transplanting the amino acid residues in some frameworks, as well as CDR sequences, into a human antibody according to a CDR grafting method (International Publication No. WO90/07861).

However, a humanized antibody derived from the 151D antibody is not limited to a specific humanized antibody, as long as it retains all 6 CDR sequences of the 151D antibody and has an antitumor activity.

It is to be noted that the heavy chain variable region of the 151D antibody has CDRH1 (GFTFSNYYMA) consisting of the amino acid sequence consisting of the amino acid residues at positions 26 to 35 in SEQ ID NO: 15 in the sequence listing, CDRH2 (SIGTVGGNTY) consisting of the amino acid sequence consisting of the amino acid residues at positions 50 to 59 in SEQ ID NO: 15 therein, and CDRH3 (EDYGGFPH) consisting of the amino acid sequence consisting of the amino acid residues at positions 99 to 106 in SEQ ID NO: 15 therein.

In addition, the light chain variable region of the 151D antibody has CDRL1 (KASQNVGTNVD) consisting of the amino acid sequence consisting of the amino acid residues at positions 24 to 34 in SEQ ID NO: 17 in the sequence listing, CDRL2 (GASNRYT) consisting of the amino acid sequence consisting of the amino acid residues at positions 50 to 56 in SEQ ID NO: 17 therein, and CDRL3 (LQYKYN-PYT) consisting of the amino acid sequence consisting of the amino acid residues at positions 89 to 97 in SEQ ID NO: 17 therein.

Moreover, the heavy chain variable region of the 198D antibody has CDRH1 (GFSLTSFHVS) consisting of the amino acid sequence consisting of the amino acid residues at positions 26 to 35 in SEQ ID NO: 19 in the sequence listing, CDRH2 (TISSGGGTY) consisting of the amino acid sequence consisting of the amino acid residues at positions 50 to 58 in SEQ ID NO: 19 therein, and CDRH3 (IS-GWGHYYVMDV) consisting of the amino acid sequence consisting of the amino acid residues at positions 98 to 109 in SEQ ID NO: 19 therein.

Furthermore, the light chain variable region of the 198D antibody has CDRL1 (QASEDIYSGLA) consisting of the amino acid sequence consisting of the amino acid residues at positions 24 to 34 in SEQ ID NO: 21 in the sequence listing, CDRL2 (GAGSLQD) consisting of the amino acid sequence consisting of the amino acid residues at positions 50 to 56 in SEQ ID NO: 21 therein, and CDRL3 (QQGLK-FPLT) consisting of the amino acid sequence consisting of the amino acid residues at positions 89 to 97 in SEQ ID NO: 21 therein.

A concrete example of a humanized antibody of the rat antibody 151D can be any given combination of: a heavy chain comprising a heavy chain variable region consisting of any one of (1) an amino acid sequence consisting of the amino acid residues at positions 20 to 136 shown in SEQ ID NO: 33 (h151D-H1) or 35 (h151D-H4) in the sequence listing, (2) an amino acid sequence having a homology of at least 95% or more to the sequence of a framework region other than at each CDR sequence in the sequence of the above (1), and (3) an amino acid sequence comprising a deletion, substitution or addition of one or several amino acids in the sequence of a framework region other than at each CDR sequence in the sequence of the above (1); and a light chain comprising a light chain variable region consisting of any one of (4) an amino acid sequence consisting of the amino acid residues at positions 21 to 129 shown in SEQ ID NO: 37 (h151D-L1) or 39 (h151D-L4), (5) an amino acid sequence having a homology of at least 95% or more to the sequence of a framework region other than at each CDR sequence in the sequence of the above (4), and (6) an amino acid sequence comprising a deletion, substitution or addition of one or several amino acids in the sequence of a framework region other than at each CDR sequence in the sequence of the above (4).

On the other hand, a concrete example of a humanized antibody of the rat antibody 198D can be any given combination of: a heavy chain comprising a heavy chain variable region consisting of any one of (1) an amino acid sequence consisting of the amino acid residues at positions 20 to 139 shown in SEQ ID NO: 41 (h198D-H3) in the sequence listing, (2) an amino acid sequence having a homology of at least 95% or more to the sequence of a framework region other than at each CDR sequence in the sequence of the above (1), and (3) an amino acid sequence comprising a deletion, substitution or addition of one or several amino acids in the sequence of a framework region other than at each CDR sequence in the sequence of the above (1); and a light chain comprising a light chain variable region consisting of any one of (4) an amino acid sequence consisting of the amino acid residues at positions 21 to 129 shown in SEQ ID NO: 43 (h198D-L4) in the sequence listing, (5) an amino acid sequence having a homology of at least 95% or more to the sequence of a framework region other than at each CDR sequence in the sequence of the above (4), and (6) an amino acid sequence comprising a deletion, substitution or addition of one or several amino acids in the sequence of a framework region other than at each CDR sequence in the sequence of the above (4).

Examples of a preferred combination of a heavy chain and a light chain of the humanized 151D antibody can include: an antibody consisting of a heavy chain having a heavy chain variable region consisting of the amino acid sequence consisting of the amino acid residues at positions 20 to 136 shown in SEQ ID NO: 33, and a light chain having a light chain variable region consisting of the amino acid sequence consisting of the amino acid residues at positions 21 to 129 shown in SEQ ID NO: 37; and an antibody consisting of a heavy chain having a heavy chain variable region consisting of the amino acid sequence consisting of the amino acid residues at positions 20 to 136 shown in SEQ ID NO: 35, and a light chain having a light chain variable region consisting of the amino acid sequence consisting of the amino acid residues at positions 21 to 129 shown in SEQ ID NO: 39.

Examples of a more preferred combination thereof can include: an antibody (h151D-H1L1) consisting of a heavy chain having the amino acid sequence shown in SEQ ID NO: 33 and a light chain having the amino acid sequence shown in SEQ ID NO: 37; and an antibody (h151D-H4L4) consisting of a heavy chain having the amino acid sequence shown in SEQ ID NO: 35 and a light chain having the amino acid sequence shown in SEQ ID NO: 39.

An example of a preferred combination of the heavy chain and light chain of the humanized 198D antibody can be an antibody consisting of a heavy chain having a heavy chain variable region consisting of the amino acid sequence consisting of the amino acid residues at positions 20 to 139 shown in SEQ ID NO: 41, and a light chain having a light chain variable region consisting of the amino acid sequence consisting of the amino acid residues at positions 21 to 129 shown in SEQ ID NO: 43.

An example of a more preferred combination thereof can be an antibody (h198D-H3L4) consisting of a heavy chain having the amino acid sequence shown in SEQ ID NO: 41 and a light chain having the amino acid sequence shown in SEQ ID NO: 43.

By combining together sequences showing a high homology to the above described heavy chain amino acid sequences and light chain amino acid sequences, it is possible to select an antibody having cytotoxicity equivalent to each of the above described antibodies. Such a homology is a homology of generally 80% or more, preferably 90% or more, more preferably 95% or more, and most preferably 99% or more. Moreover, also by combining with one another, amino acid sequences comprising a substitution, deletion or addition of one or several amino acid residues with respect to the amino acid sequence of a heavy chain or a light chain, it is possible to select an antibody having cytotoxicity equivalent to each of the above described antibodies.

It is to be noted that the term "several" is used in the present description to mean 1 to 10, 1 to 9, 1 to 8, 1 to 7, 1 to 6, 1 to 5, 1 to 4, 1 to 3, or 1 or 2.

The amino acid substitution in the present description is preferably a conservative amino acid substitution. The conservative amino acid substitution is a substitution occurring within an amino acid group associated with certain amino acid side chains. Preferred amino acid groups are the following: acidic group=aspartic acid and glutamic acid; basic group=lysine, arginine, and histidine; non-polar group=alanine, valine, leucine, isoleucine, proline, phenylalanine, methionine, and tryptophan; and uncharged polar group=glycine, asparagine, glutamine, cysteine, serine, threonine, and tyrosine. Other preferred amino acid groups are the following: aliphatic hydroxy group=serine and threonine; amide-containing group=asparagine and glutamine; aliphatic group=alanine, valine, leucine and isoleucine; and aromatic group=phenylalanine, tryptophan and tyrosine. Such amino acid substitution is preferably carried out to the extent that the properties of a substance having the original amino acid sequence are not impaired.

Homology between two types of amino acid sequences can be determined using default parameters of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs," Nucleic Acids Res. 25: 3389-3402). The Blast algorithm can also be used by accessing www.ncbi.nlm.nih.gov/blast through the internet. It is to be noted that homology between the nucleotide sequence of the antibody of the present invention and the nucleotide sequence of another antibody can also be determined using the Blast algorithm.

In the amino acid sequence of the heavy chain of the humanized 151D antibody shown in SEQ ID NO: 33 or 35 in the sequence listing, the amino acid sequence consisting of the amino acid residues at positions 1 to 19 is a signal sequence, the amino acid sequence consisting of the amino acid residues at positions 20 to 136 is a variable region, and the amino acid sequence consisting of the amino acid residues at positions 137 to 466 is a constant region.

Moreover, in the amino acid sequence of the light chain of the humanized 151D antibody shown in SEQ ID NO: 37 or 39 in the sequence listing, the amino acid sequence consisting of the amino acid residues at positions 1 to 20 is a signal sequence, the amino acid sequence consisting of the amino acid residues at positions 21 to 129 is a variable region, and the amino acid sequence consisting of the amino acid residues at positions 130 to 234 is a constant region.

Furthermore, in the amino acid sequence of the heavy chain of the humanized 198D antibody shown in SEQ ID NO: 41 in the sequence listing, the amino acid sequence consisting of the amino acid residues at positions 1 to 19 is a signal sequence, the amino acid sequence consisting of the amino acid residues at positions 20 to 139 is a variable region, and the amino acid sequence consisting of the amino acid residues at positions 140 to 469 is a constant region.

Further, in the amino acid sequence of the light chain of the humanized 198D antibody shown in SEQ ID NO: 43 in the sequence listing, the amino acid sequence consisting of the amino acid residues at positions 1 to 20 is a signal sequence, the amino acid sequence consisting of the amino acid residues at positions 21 to 129 is a variable region, and the amino acid sequence consisting of the amino acid residues at positions 130 to 234 is a constant region.

The amino acid sequence of the heavy chain of the humanized 151D antibody shown in SEQ ID NO: 33 or 35 in the sequence listing is encoded by the nucleotide sequence shown in SEQ ID NO: 32 or 34 in the sequence listing, respectively. In addition, the sequence of SEQ ID NO: 33 is shown in FIG. 21, the sequence of SEQ ID NO: 35 is shown in FIG. 23, the sequence of SEQ ID NO: 32 is shown in FIG. 31, and the sequence of SEQ ID NO: 34 is shown in FIG. 33, respectively.

The nucleotide sequence consisting of the nucleotides at nucleotide positions 1 to 57 in each nucleotide sequence encodes the heavy chain signal sequence of the humanized 151D antibody, the nucleotide sequence consisting of the nucleotides at nucleotide positions 58 to 408 therein encodes the heavy chain variable region of the humanized 151D antibody, and the nucleotide sequence consisting of the nucleotides at nucleotide positions 409 to 1398 therein encodes the heavy chain constant region of the humanized 151D antibody The amino acid sequence of the heavy chain of the humanized 198D antibody shown in SEQ ID NO: 41 in the sequence listing is encoded by the nucleotide sequence shown in SEQ ID NO: 40 in the sequence listing. In addition, the sequence of SEQ ID NO: 41 is shown in FIG. 25, and the sequence of SEQ ID NO: 40 is shown in FIG. 35.

The nucleotide sequence consisting of the nucleotides at nucleotide positions 1 to 57 in the aforementioned nucleotide sequence encodes the heavy chain signal sequence of the humanized 198D antibody, the nucleotide sequence consisting of the nucleotides at nucleotide positions 58 to 417 therein encodes the heavy chain variable region of the humanized 198D antibody, and the nucleotide sequence consisting of the nucleotides at nucleotide positions 418 to 1407 therein encodes the heavy chain constant region of the humanized 198D antibody.

The amino acid sequence of the light chain of the humanized 151D antibody shown in SEQ ID NO: 37 or 39 in the sequence listing is encoded by the nucleotide sequence shown in SEQ ID NO: 36 or 38 in the sequence listing, respectively. In addition, the sequence of SEQ ID NO: 37 is shown in FIG. 22, the sequence of SEQ ID NO: 39 is shown in FIG. 24, the sequence of SEQ ID NO: 36 is shown in FIG. 32, and the sequence of SEQ ID NO: 38 is shown in FIG. 34, respectively.

The nucleotide sequence consisting of the nucleotides at nucleotide positions 1 to 60 in each nucleotide sequence encodes the light chain signal sequence of the humanized 151D antibody, the nucleotide sequence consisting of the nucleotides at nucleotide positions 61 to 387 therein encodes the light chain variable region of the humanized 151D antibody, and the nucleotide sequence consisting of the nucleotides at nucleotide positions 388 to 702 therein encodes the light chain constant region of the humanized 151D antibody.

The amino acid sequence of the light chain of the humanized 198D antibody shown in SEQ ID NO: 43 in the sequence listing is encoded by the nucleotide sequence shown in SEQ ID NO: 42 in the sequence listing. In addition, the sequence of SEQ ID NO: 43 is shown in FIG. 26, and the sequence of SEQ ID NO: 42 is shown in FIG. 36.

The nucleotide sequence consisting of the nucleotides at nucleotide positions 1 to 60 in the aforementioned nucleotide sequence encodes the light chain signal sequence of the humanized 198D antibody, the nucleotide sequence consisting of the nucleotides at nucleotide positions 61 to 387 therein encodes the light chain variable region of the humanized 198D antibody, and the nucleotide sequence consisting of the nucleotides at nucleotide positions 388 to 702 therein encodes the light chain constant region of the humanized 198D antibody.

Homology between these nucleotide sequences and the nucleotide sequences of other antibodies can also be determined using the Blast algorithm.

A further example of the antibody of the present invention can be a human antibody binding to the same epitope, to which the humanized 151D antibody or the humanized 198D antibody also binds. An anti-GARP human antibody means a human antibody having only the gene sequence of a human chromosome-derived antibody. The anti-GARP human antibody can be obtained by the aforementioned method.

If a newly produced human antibody binds to a partial peptide or a partial three-dimensional structure, to which the humanized 151D antibody or the humanized 198D antibody binds, it can be determined that the human antibody binds to the same epitope, to which the humanized 151D antibody or the humanized 198D antibody binds. In addition, by confirming that the human antibody competes with the humanized 151D antibody or the humanized 198D antibody for the binding thereof to GARP (i.e., the human antibody interferes with the binding of the humanized 151D antibody or the humanized 198D antibody to GARP), it can be determined that the human antibody binds to the same epitope, to which the humanized 151D antibody or humanized 198D antibody binds, even if the specific sequence or structure of the epitope has not been determined. If it is confirmed that the concerned human antibody binds to the same epitope to which the humanized 151D antibody or the humanized 198D antibody binds, then, it is strongly expected that the human antibody should have cytotoxicity equivalent to that of the humanized 151D antibody or the humanized 198D antibody.

The chimeric antibody, humanized antibody, or human antibody obtained by the aforementioned methods is evaluated by the methods described later in the Examples, etc., in terms of binding activity to an antigen, and thus, a preferred antibody can be selected.

The present invention also includes a modification of an antibody. The term "modification" is used herein to mean the antibody of the present invention, which is chemically or biologically modified. Examples of such a chemical modification include the binding of a chemical moiety to an amino acid skeleton, and the chemical modification of an N-linked or O-linked carbohydrate chain. Examples of such a biological modification include antibodies which have undergone a posttranslational modification (e.g., an N-linked or O-linked sugar chain modification, N-terminal or C-terminal processing, deamidation, isomerization of aspartic acid, and oxidation of methionine), and antibodies, to the N-terminus of which a methionine residue is added as a result of having been allowed to be expressed using prokaryote host cells. In addition, such a modification also includes labeled antibodies for enabling detection or isolation of the antibody of the present invention or an antigen, such as, for example, an enzyme labeled antibody, a fluorescent-labeled antibody, and an affinity-labeled antibody. Such a modification of the antibody of the present invention is useful for the improvement of the stability and retention in blood of the original antibody of the present invention, a reduction in antigenicity, detection or isolation of such an antibody or antigen, etc.

Moreover, by regulating a sugar chain modification (glycosylation, de-fucosylation, etc.) that binds to the antibody of the present invention, antibody-dependent cellular cytotoxicity can be enhanced. As techniques of regulating the sugar chain modification of an antibody, those described in WO99/54342, WO2000/61739, WO2002/31140, etc. are known, but the techniques are not limited thereto. The antibody of the present invention also includes antibodies in which the aforementioned sugar chain modification has been regulated.

After an antibody gene has been isolated, the gene is introduced into a suitable host to produce an antibody, using a suitable combination of a host and an expression vector. A specific example of the antibody gene can be a combination of a gene encoding the heavy chain sequence of the antibody described in the present description and a gene encoding the light chain sequence of the antibody described therein. Upon transformation of host cells, a heavy chain sequence gene and a light chain sequence gene can be inserted into a single expression vector, or these genes can instead each be inserted into different expression vectors.

When eukaryotic cells are used as hosts, animal cells, plant cells or eukaryotic microorganisms can be used. Examples of animal cells include mammalian cells such as COS cells which are monkey cells (Gluzman, Y., Cell (1981) 23, p. 175-182, ATCC CRL-1650), mouse fibroblasts NIH3T3 (ATCC No. CRL-1658), and a dihydrofolate reductase-deficient cell line of Chinese hamster ovary cells (CHO cells, ATCC CCL-61) (Urlaub, G. and Chasin, L. A. Proc. Natl. Acad. Sci. U.S.A. (1980) 77, p. 4126-4220).

When prokaryotic cells are used as hosts, *Escherichia coli* or *Bacillus subtilis* can be used, for example.

An antibody gene of interest is introduced into these cells for transformation, and the transformed cells are then cultured in vitro to obtain an antibody. In the aforementioned culture, there are cases where yield is different depending on the sequence of the antibody, and thus, it is possible to select an antibody, which is easily produced as a medicament, from antibodies having equivalent binding activity, using the yield as an indicator. Accordingly, the antibody of the present invention also includes an antibody obtained by the above described method for producing an antibody, which is characterized in that it comprises a step of culturing the transformed host cells and a step of collecting an antibody of interest from the culture obtained in the aforementioned step.

It is known that the lysine residue at the carboxyl terminus of the heavy chain of an antibody produced in cultured mammalian cells is deleted (Journal of Chromatography A, 705: 129-134 (1995)), and also, it is known that the two amino acid residues at the heavy chain carboxyl terminus, glycine and lysine, are deleted, and that the proline residue positioned at the carboxyl terminus is newly amidated (Analytical Biochemistry, 360: 75-83 (2007)). However, such deletion and modification of these heavy chain sequences do not have an influence on the antigen-binding activity and effector function (activation of complement, antibody-dependent cellular cytotoxicity, etc.) of an antibody. Accordingly, the present invention also includes an antibody that has undergone the aforementioned modification, and specific examples of such an antibody include a deletion mutant comprising a deletion of 1 or 2 amino acids at the heavy chain carboxyl terminus, and a deletion mutant formed by amidating the aforementioned deletion mutant (e.g., a heavy chain in which the proline residue at the carboxyl terminal site is amidated). However, deletion mutants involving a deletion at the carboxyl terminus of the heavy chain of the antibody according to the present invention are not limited to the above described deletion mutants, as long as they retain antigen-binding activity and effector function. Two heavy chains constituting the antibody according to the present invention may be any one type of heavy chain selected from the group consisting of a full length antibody and the above described deletion mutants, or a combination of any two types selected from the aforementioned group. The ratio of individual deletion mutants can be influenced by the types of cultured mammalian cells that produce the antibody according to the present invention, and the culture conditions. The main ingredient of the antibody according to the present invention can be antibodies where one amino acid residue is deleted at each of the carboxyl termini of the two heavy chains.

Examples of the isotype of the antibody of the present invention can include IgG (IgG1, IgG2, IgG3, and IgG4). Among others, IgG1 and IgG2 are preferable.

Examples of the general function of an antibody can include antigen-binding activity, activity of neutralizing the activity of an antigen, activity of enhancing the activity of an antigen, ADCC activity, antibody dependent cellular phagocytosis (ADCP) activity, and complement-dependent cytotoxic (CDC) activity. The function of the antibody according to the present invention is binding activity to GARP, preferably ADCC activity, and more preferably cytotoxicity (antitumor activity) caused by ADCC-mediated inhibition of Treg function. Moreover, the antibody of the present invention may have ADCP activity and/or CDC activity, as well as ADCC activity. In particular, with regard to medicaments comprising existing antitumor antibodies, it has been reported that the medicaments directly act on tumor cells to block growth signals, that they directly act on tumor cells to induce cell death signals, that they suppress angiogenesis, that they cause ADCC activity via NK cells, and that they induce CDC activity via complement to suppress the growth of tumor cells (J Clin Oncol 28: 4390-4399. (2010), Clin Cancer Res; 16 (1); 11-20. (2010)). However, with regard to the ADCP activity of the anti-GARP antibody according to the invention of the present application, at least, the present inventors have not known that the ADCP activity had been reported as an activity of a medicament comprising an existing anti-GARP antitumor antibody.

The antibody of the present invention may be an antibody that has been multimerized to enhance affinity for an antigen. The antibody to be multimerized may be either a single type of antibody, or multiple antibodies recognizing multiple epitopes of a single antigen. Examples of a method of multimerizing an antibody can include the binding of an IgG CH3 domain to two scFv (single-chain antibodies), the binding of an antibody to streptavidin, and introduction of a helix-turn-helix motif.

The antibody of the present invention may also be a polyclonal antibody that is a mixture of multiple types of anti-GARP antibodies having different amino acid sequences. An example of the polyclonal antibody can be a mixture of multiple types of antibodies having different CDRs. As such a polyclonal antibody, an antibody obtained by culturing a mixture of cells producing different antibodies and then purifying the obtained culture can be used (see WO2004/061104).

As a modification of the antibody, an antibody binding to various types of molecules such as polyethylene glycol (PEG) can be used.

The antibody of the present invention may further be a conjugate formed by such an antibody and another drug (Immunoconjugate). Such an antibody can be, for example, an antibody that binds to a radioactive substance or a compound having pharmacological action (Nature Biotechnology (2005) 23, p. 1137-1146). Examples of such an antibody can include Indium ($^{111}$In) Capromab pendetide, Technetium ($^{99m}$Tc) Nofetumomab merpentan, Indium ($^{111}$In) Ibritumomab, Yttrium ($^{90}$Y) Ibritumomab, and Iodine ($^{131}$I) Tositumomab.

3. Medicament Containing Anti-GARP Antibody

Since the antibody obtained by the method described in the above section "2. Production of anti-GARP antibody" exhibits cytotoxicity on Treg, it can be used as a medicament, and in particular, as a therapeutic agent for cancer and infectious disease (in particular, malaria and HIV infection).

Cytotoxicity caused by an antibody in vitro can be measured based on the activity of suppressing the proliferative responses of cells.

For example, a cancer cell line overexpressing GARP is cultured, and antibodies having different concentrations are added to the culture system. Thereafter, the inhibitory activity of the antibody on focus formation, colony formation and spheroid growth can be measured.

The in vivo therapeutic effects of an antibody on the cancer of an experimental animal can be measured, for example, by administering the antibody to a nude mouse into which a tumor cell line overexpressing GARP has been transplanted, and then measuring a change in the cancer cells.

Examples of the cancer type can include lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, and blood cancer. However, the cancer type is not limited to the aforementioned examples, as long as the cancer cells, as therapeutic targets, express GARP.

As a substance used in a medicament acceptable for the pharmaceutical composition of the present invention, a substance that is non-toxic to a subject, to whom the pharmaceutical composition is to be administered, is preferable, in terms of an applied dose or an applied concentration.

The pharmaceutical composition of the present invention can comprise a pharmaceutical substance for altering or retaining pH, osmotic pressure, viscosity, transparency, color, isotonicity, sterility, stability, solubility, sustained release rate, absorptivity, and permeability. Examples of the pharmaceutical substance can include the following substances, but are not limited thereto: amino acids such as glycine, alanine, glutamine, asparagine, arginine or lysine; antibacterial agents; antioxidants such as ascorbic acid, sodium sulfate or sodium hydrogen sulfite; buffers such as a phosphate, citrate or borate buffer, sodium hydrogen carbonate, or a Tris-HCl solution; fillers such as mannitol or glycine; chelating agents such as ethylenediaminetetraacetic acid (EDTA); complexing agents such as caffeine, polyvinylpyrrolidine, β-cyclodextrin or hydroxypropyl-β-cyclodextrin; bulking agents such as glucose, mannose or dextrin; other carbohydrates such as monosaccharides or disaccharides; a coloring agent; a flavor agent; a diluent; an emulsifier; hydrophilic polymers such as polyvinylpyrrolidine; a low-molecular-weight polypeptide; salt-forming counterions; antiseptics such as benzalkonium chloride, benzoic acid, salicylic acid, thimerosal, phenethyl alcohol, methylparaben, propylparaben, chlorhexidine, sorbic acid or hydrogen peroxide; solvents such as glycerin, propylene glycol or polyethylene glycol; sugar alcohols such as mannitol or sorbitol; polysorbates such as a suspending agent, sorbitan ester, polysorbate 20 or polysorbate 80; surfactants such as Triton, tromethamine, lecithin or cholesterol; stability enhancers such as sucrose or sorbitol; a suspending agent; elasticity enhancers such as sodium chloride, potassium chloride, mannitol or sorbitol; transporting agents; excipients; and/or pharmaceutical adjuvants. Such a pharmaceutical substance is preferably added to an anti-GARP antibody in an amount of 0.001 to 100 times, in particular, 0.1 to 10 times higher than the weight of the anti-GARP antibody. The preferred composition of a pharmaceutical composition in a formulation can be determined, as appropriate, by a person skilled in the art, depending on the target disease, the applied administration route, etc.

An excipient or a carrier in the pharmaceutical composition may be a liquid or a solid. A suitable excipient or carrier may be water for injection, normal saline, an artificial cerebrospinal fluid, or other substances commonly used in parenteral administration. Neutral normal saline or normal saline comprising serum albumin can also be used as a carrier. The pharmaceutical composition can comprise a Tris buffer with pH 7.0-8.5, an acetate buffer with pH 4.0-5.5, or a citrate buffer with pH 3.0-6.2. In addition, these buffers can also comprise sorbitol or other compounds.

Examples of the pharmaceutical composition of the present invention can include a pharmaceutical composition comprising an anti-GARP antibody and a pharmaceutical composition comprising an anti-GARP antibody and at least one cancer therapeutic agent. The pharmaceutical composition of the present invention is prepared as a drug having a selected composition and a necessary purity in the form of a freeze-dried product or a liquid. Such a pharmaceutical composition comprising an anti-GARP antibody and a pharmaceutical composition comprising an anti-GARP antibody and at least one cancer therapeutic agent can also be molded into a freeze-dried product comprising a suitable excipient such as sucrose.

A cancer therapeutic agent comprised, together with an anti-GARP antibody, in the above described pharmaceutical composition may be administered to an individual, simultaneously, separately, or continuously, together with the anti-GARP antibody. Otherwise, the cancer therapeutic agent and the anti-GARP antibody may each be administered to the subject at different administration intervals. Examples of such a cancer therapeutic agent can include abraxane, carboplatin, cisplatin, gemcitabine, irinotecan (CPT-11), paclitaxel, pemetrexed, sorafenib, vinblastin, the drugs described in International Publication No. WO2003/038043, LH-RH analogs (leuprorelin, goserelin, etc.), estramustine-phosphate, estrogen antagonists (tamoxifen, raloxifene, etc.), and aromatase inhibitors (anastrozole, letrozole, exemestane, etc.). However, examples of the cancer therapeutic agent are not limited to the above described drugs, as long as the agents have antitumor activity.

The subject to be the target for administration is not particularly limited. It is preferably a mammal, and more preferably a human.

The pharmaceutical composition of the present invention can be prepared for use in parenteral administration, or for use in gastrointestinal absorption involving oral administration. The composition and concentration of a formulation can be determined depending on the administration method. With regard to the affinity of an anti-GARP antibody comprised in the pharmaceutical composition of the present invention for GARP, namely, the dissociation constant (Kd value) of the anti-GARP antibody to GARP, as the affinity increases (i.e., the Kd value is low), the pharmaceutical composition can exhibit medicinal effects, even if the applied dose thereof to a human is decreased. Based on these results, the applied dose of the pharmaceutical composition of the present invention to a human can also be determined. When a human-type anti-GARP antibody is administered to a human, the antibody may be administered at a dose of from about 0.001 to 100 mg/kg once or several times at intervals of 1 to 180 days. Examples of the form of the pharmaceutical composition of the present invention can include an injection including a drip infusion, a suppository, a transnasal agent, a sublingual agent, and a transdermal absorption agent.

Hereinafter, the present invention will be specifically described in the following examples. However, these examples are not intended to limit the scope of the present invention.

EXAMPLES

In the following examples, unless otherwise specified, individual operations regarding genetic manipulation have been carried out according to the method described in "Molecular Cloning" (Sambrook, J., Fritsch, E. F. and Maniatis, T., published by Cold Spring Harbor Laboratory Press in 1989) or other methods described in experimental manuals used by persons skilled in the art, or when commercially available reagents or kits have been used, the examples have been carried out in accordance with the instructions included in the commercially available products.

Hereinafter, the present invention will be specifically described in the following examples. However, these examples are not intended to limit the scope of the present invention.

Example 1

Obtaining Antibody

1)-1 Separation of Anti-GARP Fab by Panning in Phage Display

An n-CoDeR Fab phage library (BioInvent) was used in separation of Fab binding to GARP. Using EZ-Link NHS-Chromogenic-Biotin reagent (Thermo Scientific), GARP (R&D Systems) was biotinylated. For liquid-phase panning, the biotinylated GARP was solid-phased on Dynabeads Streptavidin M-280 (Life Technologies), and phages were then added. Unbound phages were removed by a washing operation using a magnet (DynaMag-2, Life Technologies). Thereafter, GARP-bound phages were collected by treating them with trypsin (Sigma-Aldrich), and were then amplified using *Escherichia coli*. In total, panning operations were carried out three times, and, using restriction enzymes, a DNA fragment encoding Fab was cut from a polyclonal phagemid, and was then loaded on an expression vector for *Escherichia coli*. Thereafter, *Escherichia coli* TOP10F' (Life Technologies) was transformed with the expression vector, and Fab was then allowed to express in the presence of IPTG (Sigma-Aldrich). The obtained Fab was subjected to screening by ELISA.

1)-2 Screening for GARP-binding Fab by ELISA

50 µL GARP, which had been diluted to 2 µg/mL with PBS (0.01 M phosphate buffered saline (pH 7.4) containing 0.138 M sodium chloride and 0.0027 M potassium chloride; Sigma-Aldrich), was added to each well of a 384-well Maxi-sorp plate (Black, Nunc), and it was then incubated overnight at 4° C. for coating the plate. Alternatively, 50 µL of NeutrAvidin (Life Technologies) which had been diluted to 1 µg/mL with PBS was added to such a 384-well Maxi-sorp plate for coating the plate (by incubating overnight at 4° C.). Thereafter, the plate was washed with an ELISA buffer (PBS (Sigma-Aldrich) supplemented with 0.05% Tween-20 (Bio-RAD)) three times, and biotinylated GARP was then added thereto (1 pmol/50 µL PBS/well), followed by incubation at room temperature for 1 hour with mixing. The plate was washed with ELISA buffer three times, was then blocked with Blocker Casein (Thermo Scientific), and was further washed with the ELISA buffer three times. Thereafter, a culture supernatant containing Fab produced by *Escherichia coli* was added, and the plate was then incubated at room temperature for 1 hour with mixing. The plate was washed with the ELISA buffer three times, and 50 μL of 2500-fold diluted Horseradish peroxidase (HRP)-labeled anti-human F (ab')$_2$ antibody (R&D Systems) was added. The plate was further incubated at room temperature for 1 hour with mixing. The reaction mixture was washed with the ELISA buffer three times, and SuperSignal Pico ELISA Chemiluminescent substrate (Thermo Scientific) was then added to the wells. Ten minutes later, chemiluminescence was measured using a plate reader (Envision 2104 Multilabel Reader, Perkin Elmer), and GARP-bound Fab was isolated.

1)-3 Determination of Nucleotide Sequence of ELISA-positive Clone

The heavy chain and light chain variable regions of ELISA-positive clones (105F and 110F) were analyzed by a Dye Terminator method (BigDye (registered trademark) Terminator v3.1, Life Technologies). The sequences of the main primers used in sequencing are as follows.

Primer A: 5'-GAA ACA GCT ATG AAA TAC CTA TTG C-3' (SEQ ID NO: 10)
Primer B: 5'-GCC TGA GCA GTG GAA GTC C-3' (SEQ ID NO: 11)
Primer C: 5'-TAG GTA TTT CAT TAT GAC TGT CTC-3' (SEQ ID NO: 12)
Primer D: 5'-CCC AGT CAC GAC GTT GTA AAA CG-3' (SEQ ID NO: 13)

As a result of the above described analysis, the nucleotide sequences of the variable regions of the 105F antibody and 110F antibody genes were determined.

The nucleotide sequence of the heavy chain variable region of the 105F antibody was a sequence consisting of the nucleotides at nucleotide positions 1 to 354 in the nucleotide sequence shown in SEQ ID NO: 6 in the sequence listing, and the nucleotide sequence of the light chain variable region of the 105F antibody was a sequence consisting of the nucleotides at nucleotide positions 1 to 336 in the nucleotide sequence shown in SEQ ID NO: 7 in the sequence listing.

The nucleotide sequence of the heavy chain variable region of the 110F antibody was a sequence consisting of the nucleotides at nucleotide positions 1 to 369 in the nucleotide sequence shown in SEQ ID NO: 8 in the sequence listing, and the nucleotide sequence of the light chain variable region of the 110F antibody was a sequence consisting of the nucleotides at nucleotide positions 1 to 333 in the nucleotide sequence shown in SEQ ID NO: 9 in the sequence listing.

1)-4: Preparation of Full-length IgG, and Expression and Purification of IgG

Full-length IgG of ELISA-positive clones including 105F and 110F was prepared by the following method.

A nucleotide sequence encoding Fab was determined, and thereafter, nucleotide sequences corresponding to the variable regions of the heavy chain and light chain of each antibody specified in the above 1)-3 were specified.

According to a common method, the nucleotide sequence of the variable region of the above described heavy chain was ligated to a nucleotide sequence encoding the constant region of the heavy chain of human IgG$_1$ (CH1+Fc region: the amino acid sequence at amino acid positions 119 to 448 in the amino acid sequence shown in SEQ ID NO: 2 in the sequence listing), and also, the nucleotide sequence of the variable region of the above described light chain was ligated to a nucleotide sequence encoding the constant region of the light chain of human IgG$_1$ (CL: the amino acid sequence at amino acid positions 113 to 217 in the amino acid sequence shown in SEQ ID NO: 3 in the sequence listing). Thereafter, the obtained ligate was inserted into an expression vector for animal cells, such as pcDNA3.3 (Invitrogen), to construct an IgG expression vector for animal cells.

The nucleotide sequence of the constructed IgG expression vector was analyzed again, so that it was confirmed that the nucleotide sequence of the full-length heavy chain of the 105F antibody was the nucleotide sequence shown in SEQ ID NO: 6 in the sequence listing, and that the nucleotide sequence of the full-length light chain of the 105F antibody was the nucleotide sequence shown in SEQ ID NO: 7 in the sequence listing.

It was also confirmed that the nucleotide sequence of the full-length heavy chain of the 110F antibody was the nucleotide sequence shown in SEQ ID NO: 8 in the sequence listing, and that the nucleotide sequence of the full-length light chain of the 110F antibody was the nucleotide sequence shown in SEQ ID NO: 9 in the sequence listing.

Moreover, based on the above described nucleotide sequences, the amino acid sequences of the full-length heavy chain and full-length light chain of the 105F antibody encoded by the nucleotide sequences, and the amino acid sequences of the full-length heavy chain and full-length light chain of the 110F antibody encoded by the nucleotide sequences, were determined.

The amino acid sequence of the heavy chain of the 105F antibody was the amino acid sequence shown in SEQ ID NO: 2 in the sequence listing, and the amino acid sequence of the light chain thereof was the amino acid sequence shown in SEQ ID NO: 3 in the sequence listing.

The amino acid sequence of the heavy chain of the 110F antibody was the amino acid sequence shown in SEQ ID NO: 4 in the sequence listing, and the amino acid sequence of the light chain thereof was the amino acid sequence shown in SEQ ID NO: 5 in the sequence listing.

The IgG of the 105F antibody or the 110F antibody was transiently expressed by inserting the above described IgG expression vector for animal cells into FreeStyle 293F cells (Life Technologies), and then the resulting IgGs were purified using a Protein A Affinity column (HiTrap Mab Select SuRe, GE Healthcare), as necessary. Thereafter, the buffer in which IgG was dissolved was replaced with PBS using Vivaspin 20 (7k MWCO, GE Healthcare) and the resultant was then subjected to the following step "1)-5."

1)-5 Confirmation of Binding of Purified IgG to GARP According to ELISA

100 μL of human GARP (R&D Systems, catalog number: 6055-LR) diluted to 1 μg/mL with PBS was added to each well of a 96-well Maxi-sorp plate (Black, Nunc), and the plate was then incubated overnight at 4° C. for coating the plate.

The plate was washed with ELISA buffer three times, and then blocked with Blocker Casein at room temperature for 1 hour. The plate was washed with the ELISA buffer three times, and 100 μL of 50 nM 105F antibody, 50 nM 110F antibody, 50 nM human IgG (Jackson Immuno Research), 50 nM mouse anti-GARP antibody (Plato-1, ENZO Life Science) or 50 nM mouse IgG (Jackson Immuno Research) was added to the wells, and the plate was incubated at room temperature for 1 hour with mixing.

The plate was washed with the ELISA buffer three times. After that, 100 μL of HRP-labeled anti-human Fc antibody (R&D Systems), which had been 5000-fold diluted with PBS, was added to wells treated with 105F antibody, 110F antibody or human IgG. On the other hand, 100 μL of HRP-labeled anti-mouse Fc antibody (R&D Systems), which had been 5000-fold diluted with PBS, was added to the wells treated with mouse anti-GARP antibody and mouse IgG. The plate was incubated at room temperature for 1 hour with mixing.

The plate was washed with the ELISA buffer five times, and 0.1 mL of SuperSignal Pico ELISA Chemiluminescent substrate was then added to the wells. Ten minutes later, chemiluminescence was measured using a plate reader (Envision 2104 Multilabel Reader, Perkin Elmer).

As a result, it was demonstrated that the 105F antibody and the 110F antibody bound to GARP (FIG. 10) as commercially available anti-GARP antibody did.

Example 2

Binding to Antigen Gene-expressing Cells

Regarding a GARP expression vector, a cDNA clone of human GARP (Origene) was purchased, and it was then cloned into a pcDNA3.1 (+) vector (Invitrogen) according to a common method. Thereafter, the nucleotide sequence thereof was confirmed.

The GARP expression vector and a pcDNA3.1 vector used as a control were each transfected into HEK-293T cells (ATCC: CRL-11268), using Lipofectamine 2000 (Invitrogen). The resulting cells were cultured in a DMEM medium (Invitrogen) supplemented with 10% fetal bovine serum (FBS, Hyclone) overnight in 5% $CO_2$ at 37° C. Thereafter, the cells were harvested from the plate by TrypLE Express (Invitrogen) treatment, and the cells were washed with MACS buffer (PBS containing 0.5% BSA and 2 mM EDTA; Miltenyi Biotec) twice and were then suspended in the same solution as described above. The 105F antibody and control human IgG (ENZO Life Science) were each added to the cell suspension, and the cells were incubated for 15 minutes at 4° C. The cells were washed twice with MACS buffer. Fluorescein isothiocyanate (FITC)-labeled anti-IgG antibody (Jackson ImmunoResearch Laboratories) was added and suspended, and the cells were further incubated at 4° C. for 15 minutes. The cells were washed twice with MACS buffer, and the cells were then fixed with 1% PFA (prepared from Paraformaldehyde 32% solution (ELECTRON MICROSCOPY SCIENCES)), and measured by using a flow cytometer (FACS Canto II; Becton Dickinson). The data was analyzed using Flowjo (TreeStar). Dead cells were removed from the analysis by gating out cells stained with Horizon FVS450 (Becton Dickinson). Thereafter, a histogram of the FITC fluorescence intensity of live cells was generated.

In terms of HEK-293T cells transfected with the control vector alone a histogram of fluorescence intensity for the 105F antibody was similar to that for the control IgG. On the other hand, in terms of GARP-expressing HEK-293T cells, it was confirmed that the histogram for the 105F antibody shifted to a strong fluorescence intensity side, in comparison to the histogram for the control IgG (FIG. 11). From the aforementioned results, it was found that the 105F antibody specifically bound to GARP expressed by HEK-293T cells.

Example 3

Binding to Endogenous GARP-expressing Cells

3)-1 Flow Cytometric Analysis Using L428 Cells
A fluorescent-labeled form of the 105F antibody was prepared using an Alexa Fluor 647 monoclonal antibody labeling kit (Invitrogen). L428 cells (obtained from DSMZ) were washed twice with MACS buffer, and were suspended in the same solution. The labeled 105F antibody was added to the cell suspension, and the cells were incubated for 30 minutes at 4° C. The cells were washed twice with MACS buffer, and the cells were then fixed with 1% PFA, and measured by using a flow cytometer (FACS Canto II, Becton Dickinson). The data was analyzed using FlowJo (TreeStar). Dead cells were removed by gating out cells stained with Horizon FVS450. Thereafter, a histogram of the FITC fluorescence intensity of live cells was generated. In comparison to the histogram of fluorescence intensity for L428 cells alone, the histogram of L428 cells to which the 105F antibody had been added shifted to the strong fluorescence intensity side. Thus, it was confirmed that the 105F antibody bound to GARP endogenously expressed by the cells (FIG. 12).

3)-2 Flow Cytometric Analysis Using Human Treg
Peripheral blood mononuclear cells (PBMC) from a healthy subject were separated using Ficoll-Paque PLUS (GE Healthcare), and the separated cells were then seeded at $2 \times 10^6$ cells/mL in RPMI1640 medium (Invitrogen) supplemented with 10% FBS (hereinafter referred to as "RP-F10 medium") in a low-adhesion 24-well plate (Costar). An anti-CD3 antibody (BD Pharmingen) and an anti-CD28 antibody (BD Pharmingen) were added to the wells, and the cells were cultured for 20 hours. Thereafter, the cells were suspended in FACS buffer (HBSS (Invitrogen) supplemented with 10 mM HEPES (Invitrogen), 2 mM EDTA (Invitrogen), and 2% FBS), and the labeled 105F antibody prepared in the above 3)-1 and an Alexa Fluor 647-labeled anti-GARP antibody (G14D9, eBioscience) were added to the suspension. The cells were incubated on ice for 30 minutes. The cells were washed with FACS buffer, and Fixation/Permeabilization working solution (eBioscience) was added. The cells were further incubated on ice for 30 minutes, and the cells were washed with Permeabilization buffer (eBioscience). After that, 2% rat serum (eBioscience) was added to the cells. The cells were incubated at room temperature for 15 minutes, and PE-labeled anti-Foxp3 antibody (eBioscience) was added, followed by further incubation at room temperature for 30 minutes. The cells were washed and fixed with a tissue-fixing solution which was prepared by two-fold diluting 4% Paraformaldehyde phosphate buffer solution (Wako Pure Chemical Industries, Ltd.) with D-PBS (Invitrogen) at 4° C. for 15 minutes or more. After the cells were washed with the FACS buffer, the cells were measured by using a flow cytometer (FACS Canto II; Becton Dickinson) and were analyzed using FlowJo (Tree Star). As a result, the 105F antibody bound to FoxP3-positive Treg as commercially available anti-GARP antibody did (FIG. 13).

Example 4

Properties of Anti-GARP Antibody

4)-1 ADCC Activity
4)-1-1 Preparation of Effector Cells
Frozen human PBMC (Cellular Technology) was thawed in accordance with the protocols. NK cells were purified from the PBMC, using an NK cell isolation kit (Miltenyi Biotec). The obtained NK cells were incubated overnight in an RP-F10 medium supplemented with 100 IU/mL rhIL-2 (Novartis). Thereafter, the number of live cells was counted by a trypan blue-exclusion test, and the cells were then re-suspended in an RP-F10 medium at a cell density of $2 \times 10^5$ cells/mL. The obtained cells were used as effector cells.

4)-1-2 Preparation of Target Cells

30 μL (1110 kBq) of Chromium-51 ($^{51}Cr$) was mixed with 0.6×10$^6$ L428 cells described in Example 3)-1, in RPMI1640 medium (Invitrogen) supplemented with 10% FBS, and the cells were incubated for 2 hours in 5% $CO_2$ at 37° C., so that the cells were radio-labeled. The labeled cells were washed three times with RPMI1640 medium (Invitrogen) supplemented with 10% FBS, and the cells were then re-suspended in the same medium at 4×10$^4$ cells/mL. The obtained cells were used as target cells.

4)-1-3 $^{51}Cr$ Release Assay

The 105F antibody, which had been diluted with an RP-F10 medium so that final concentration would be at 1, 10, 100, or 1000 ng/mL, was dispensed in an amount of 50 μL/well into a 96-well U-bottom microplate (Costar), and the target cells were added to the wells (50 μL/well). The plate was incubated at 4° C. for 30 minutes. Subsequently, the effector cells were added to the wells (100 μL/well), and the plate was incubated in 5% $CO_2$ at 37° C. for 4 hours. Thereafter, 50 μL/well of supernatant was collected and applied to LumaPlate (PerkinElmer), and the released gamma-ray dose was measured by using a gamma counter. The cell lysis rate caused by ADCC activity was calculated according to the following formula.

Cell lysis rate (%)=(A-B)/(C-B)×100

A: Count of sample well
B: Mean value (n=3) of count of spontaneous release (well without antibody and effector cells). Upon addition of the antibody and upon addition of the effector cells, 50 μL and 100 μL of RP-F10 media were added, respectively. The same operations as those for the sample wells were carried out other than the above.
C: Mean value (n=3) of count of maximum release (well in which the target cells were dissolved with a surfactant). Upon addition of the antibody, 50 μL of RP-F10 medium was added. Upon addition of the effector cells, 100 μL of RP-F10 medium supplemented with 2% (v/v) Triton-X100 (Sigma) was added. The same operations as those for the sample wells were carried out other than the above.

The results are shown in FIG. 14. The 105F antibody exhibited cytolytic activity on L428 cells in an antibody concentration dependent manner. On the other hand, the control human IgG did not exhibit such cytolytic activity. Thus, the 105F antibody had ADCC activity on L428 cells expressing endogenous GARP. It is to be noted that the human IgG1 anti-GARP antibodies (MHG8 and LHG10) produced based on the sequence information described in Patent Literature 1 did not exhibit ADCC activity.

4)-2 Inhibitory Activity to Treg Function

4)-2-1 Preparation of Treg, Teff (Effector T Cells: CD4-positive CD25-negative Helper T cells), and Accessory Cells CD4-positive T cells were separated from PBMC that were prepared in the same manner as in the above 4)-1-1, using CD4 T cell ISOLATION Kit (Miltenyi Biotec), and an FITC-labeled anti-CD4 antibody (Miltenyi Biotec) and an APC-labeled anti-CD25 antibody (Miltenyi Biotec) were added to the CD4-positive T cells. The cells were incubated at 4° C. for 30 minutes. After the cells were washed, the cells were suspended in MACS buffer, and CD4-positive CD25-negative cells (Teff) and CD4-positive CD25-strongly-positive cells (Treg) were separated using FACS Aria IIu (Becton Dickinson).

On the other hand, CD3-positive cells were removed from PBMC using CD3 Microbeads (Miltenyi Biotec) and the cells were irradiated at a dose of 1 C/kg (absorbed dose: 38.76 Gy/kg (3876 Rad/kg)) using an X-ray irradiator (Hitachi Medical Corporation) to prepare accessory cells.

4)-2-2 Co-culture Method and Assay for Inhibitory Activity to Treg Function

As a culture medium, RPMI1640 medium (Invitrogen) supplemented with Penicillin and Streptomycin (Invitrogen), 1×MEM NEAA (Invitrogen), 1×Sodium pyruvate (Invitrogen), 5 mM Hepes and 5% Human male AB serum (Sigma) was used. Teff (2000 cells/well) and accessory cells (20000 cells/well) were mixed and added into each well of a 96-well U-bottom microplate, and Treg were further added and seeded to wells at 500 cells/well. In addition, control wells without Treg were also prepared. An anti-CD3 antibody, an anti-CD28 antibody, and a 105F antibody were added to the wells at a final concentration of 50 or 10 μg/mL, and the plate was incubated for 5 days in 5% $CO_2$ at 37° C. Thereafter, [$^3H$]-thymidine (PerkinElmer) at 18.5 kBq/mL was prepared, and added to each well at 20 μL/well. The cells were further incubated for 18 hours. The cells were harvested in Filtermat A (PerkinElmer) by using a cell harvester (Mach II, Tomtech), and the radioactivity of [$^3H$]-thymidine incorporated into the cells was measured using a scintillation counter (MicroBeta, PerkinElmer). The measured data were expressed as corrected count per minute (CCPM).

Human IgG1 anti-GARP antibodies (MHG8 and LHG10) produced based on the sequence information described in Patent Literature 1 were also subjected to the present experiment system.

4)-2-3 Calculation of Inhibitory Activity

A mean value of three wells under individual co-culture conditions was calculated. Diminished value of proliferation in co-culturing Teff with Treg when compared with that of Teff alone, was defined as a "Suppression rate of Teff proliferation caused by Treg" (=1−[CCPM of co-culture/CCPM of Teff alone]).

The inhibitory activity of each antibody to the Treg function was determined by subtracting suppression rate of Teff proliferation by Treg in the presence of antibody from that in the absence of antibody (=[suppression rate upon non-addition of the antibody]−[suppression rate upon addition of each antibody]). It is to be noted that this inhibitory activity of a sample is calculated every time in each experiment.

The results of the inhibitory activity of the 105F antibody to the Treg function at 50 μg/mL (inhibitory rate: 72.6%) are shown in FIG. 15, and the results of the 105F antibody and the MHG-8 and LHG-10 antibodies (10 μg/mL each) are shown in FIG. 16. The MHG-8 and LHG-10 antibodies did not have inhibitory activity to the Treg function (inhibitory rates: 0.8% and 0.0%, respectively), whereas the 105F antibody significantly inhibited Treg function (inhibitory rate: 65.8%). The inhibitory rate caused by transducing siRNA to GARP into Treg was about 15%, when calculated roughly by using values in FIG. 5A (CD4+CD25−(Teff): Treg=4:1) of Non Patent Literature 10.

Example 5

Production of Rat Antibody

5)-1 Preparation of GARP Expression Vector

The expression vector described in Example 2 was used as a GARP expression vector, and an EndoFree Plasmid Giga Kit (QIAGEN) was used for mass production.

5)-2 Immunization of Rats

For immunization, WKY/Izm female rats (Japan SLC, Inc.) were used. First, the lower limbs of each rat were pre-treated with Hyaluronidase (SIGMA-ALDRICH) and a GARP expression vector was intramuscularly injected into the same sites. Subsequently, employing ECM830 (BTX), in vivo electroporation was performed on the same sites using two-needle electrode. Once every two weeks, the same in vivo electroporation was repeated, and lymph nodes or spleen was collected from the rat, and was used in production of hybridomas.

5)-3 Production of Hybridomas

The lymph nodes or splenic cells were fused with mouse myeloma SP2/0-ag14 cells (ATCC, No.CRL-1581) according to electrical cell fusion, using LF301 Cell Fusion Unit (BEX), and the cells were then diluted with ClonaCell-HY Selection Medium D (StemCell Technologies) and incubated. Hybridoma colonies that appeared in culture were picked and selected as monoclonal hybridomas. Every hybridoma colony was cultured, and culture supernatant from each hybridoma was used to screen for anti-GARP antibody-producing hybridomas.

5)-4 Antibody Screening According to Cell-ELISA Method

5)-4-1 Preparation of Antigen Gene-expressing Cells for Use in Cell-ELISA

293α cells (a stable expression cell line derived from HEK-293 cells (ATCC: CRL-1573) expressing integrin αv and integrin β3) were prepared at $7.5 \times 10^5$ cells/mL in DMEM medium (Invitrogen) supplemented with 10% FBS. In accordance with transduction procedures for using Lipofectamine 2000 (Life Technologies), a GARP expression vector or a pcDNA3.1 (+) vector used as a negative control was transfected into the cells, and the cells were dispensed in an amount of 50 μl each to a 96-Half area well plate (Corning). Thereafter, the cells were cultured in DMEM medium supplemented with 10% FBS for 24 to 27 hours in 5% $CO_2$ at 37° C. The obtained transfected cells were used for Cell-ELISA in an adhesive state.

5)-4-2 Cell-ELISA

The culture supernatant of the 293α cells transfected with expression vectors prepared in Example 5)-4-1 was removed, and culture supernatant from each hybridoma was added to the 293α cells transfected either with GARP expression vector or pcDNA3.1 (+) vector. The cells were incubated at 4° C. for 1 hour. The cells in the wells were washed once with PBS (+) supplemented with 5% FBS, and thereafter, Anti-Rat IgG-Peroxidase antibody produced in rabbits (SIGMA) that had been 500-fold diluted with PBS (+) supplemented with 5% FBS was added to the wells. The cells were incubated at 4° C. for 1 hour. The cells in the wells were washed three times with PBS (+) supplemented with 5% FBS, and OPD coloring solution (which had been prepared by dissolving o-phenylenediamine dihydrochloride (Wako Pure Chemical Industries, Ltd.) and $H_2O_2$ in an OPD solution (0.05 M trisodium citrate, 0.1 M disodium hydrogen phosphate 12-water; pH 4.5), so that the substances became 0.4 mg/ml and 0.6% (v/v), respectively) was added in an amount of 50 μl/well to the wells. While the plate was incubated with mixing for a time, a coloring reaction was carried out. Thereafter, 1M HCl was added to the plate (50 μl/well) to terminate the coloring reaction, and the absorbance at 490 nm was measured using a plate reader (ENVISION: PerkinElmer). In order to select hybridomas that produce an antibody specifically binding to human GARP expressed on the surface of a cell membrane, hybridomas that produced a culture supernatant exhibiting higher absorbance in 293α cells transfected with GARP expression vector than that in cells transfected with the control pcDNA3.1 (+)vector were selected as positive cells that produce anti-human GARP antibody.

5)-5 Antibody Screening According to Flow Cytometric Method

5)-5-1 Preparation of Antigen Gene-expressing Cells for Use in Flow Cytometric Analysis HEK-293T cells (obtained from ATCC) were seeded in a 225-cm² flask (Sumitomo Bakelite Co., Ltd.) at $5 \times 10^4$ cells/cm², and the cells were then cultured in DMEM medium supplemented with 10% FBS overnight in 5% $CO_2$ at 37° C. On the following day, HEK-293T cells were transfected with a GARP expression vector or a pcDNA3.1 (+) vector used as a negative control using Lipofectamine 2000, and the cells were further incubated overnight in 5% $CO_2$ at 37° C. On the following day, the transfected HEK-293T cells were treated with TrypLE Express (Life Technologies), were washed with DMEM medium supplemented with 10% FBS, and were re-suspended in PBS supplemented with 5% FBS. The obtained cell suspension was used in a flow cytometric analysis.

5)-5-2 Flow Cytometric Analysis

The binding specificity to human GARP of an antibody produced from hybridomas that had been determined to be positive by Cell-ELISA in Example 5)-4-2 was further confirmed by a flow cytometric analysis.

A suspension of the transiently expressing HEK-293T cells prepared in Example 5)-5-1 was centrifuged, and a supernatant was then removed. Thereafter, culture supernatant from each hybridoma was added to cells and suspended. The cells were incubated at 4° C. for 1 hour. The cells were washed twice with PBS supplemented with 5% FBS, and FITC-conjugated anti-Rat IgG (SIGMA) that had been 500-fold diluted with PBS supplemented with 5% FBS was added to the cells and suspended. The cells were incubated at 4° C. for 1 hour. The cells were washed twice with PBS supplemented with 5% FBS, and were then re-suspended in PBS supplemented with 5% FBS and 2 μg/ml 7-aminoactinomycin D (Molecular Probes). The cells were measured using a flow cytometer (FC500: manufactured by Beckman Coulter). The data was analyzed using Flowjo (TreeStar). After dead cells were removed from analysis by gating out 7-Aminoactinomycin D-positive cells, a histogram of the FITC fluorescence intensity of live cells was generated. Hybridomas producing human GARP-binding antibodies (113 clones) were selected based on results where the histogram for the antibody shifted to the strong fluorescence intensity side in HEK-293T cells transfected with GARP-expressing vector compared with cells transfected with control pcDNA3.1 vector.

5)-6 Preparation of Monoclonal Antibody

5)-6-1 Culture of Hybridomas 151D and 198D

From the rat anti-human GARP antibody-producing hybridomas obtained in the above 5)-5-2, hybridomas 151D and 198D, which had been suggested to bind strongly to human GARP, were selected.

A rat anti-GARP monoclonal antibody was purified from a hybridoma culture supernatant.

First, the volume of rat anti-GARP monoclonal antibody-producing hybridomas was sufficiently increased with ClonaCell-HY Selection Medium E, and thereafter, the medium was exchanged with Hybridoma SFM (Life Technologies) to which 20% of Ultra Low IgG FBS (Life Technologies) had been added. Thereafter, the hybridomas (8 to $9 \times 10^7$ cells) were seeded in a 1272-cm² flask (Corning), and were then cultured for 7 days. The present culture supernatant was harvested by centrifugation, and it was sterilized by passing through a 0.8-μm filter, and through a 0.45-μm filter (Corning).

5)-6-2 Purification of Monoclonal Antibody

An antibody was purified from the culture supernatant of hybridomas prepared in Example 5)-6-1 according to Protein G affinity chromatography. The antibody was adsorbed on a Protein G column (GE Healthcare Bioscience), the column was then washed with PBS, and the antibody was then eluted with a 0.1 M glycine/HCl aqueous solution (pH 2.7). 1 M Tris-HCl (pH 9.0) was added to the eluant, so that the pH was adjusted to pH 7.0 to 7.5. Thereafter, the solution was dialyzed (Thermo Scientific, Slide-A-Lyzer Dialysis Cassette), so that the buffer was replaced with PBS. Using Centrifugal UF Filter Device VIVASPIN20 (molecular weight cutoff: UF30K, Sartorius), the antibody was concentrated, so that the concentration of the antibody was adjusted to 0.7 mg/mL or more. Finally, the antibody was filtrated through a Minisart-Plus filter (Sartorius) to obtain a purified sample.

Example 6

Cloning of Rat Antibody and Production of Human Chimeric Antibody

6)-1 Cloning and Sequencing of cDNA of Rat Antibody 151D
6)-1-1 Preparation of Total RNA from 151D-producing Hybridomas In order to amplify cDNA comprising the variable region of 151D, total RNA was prepared from 151D-producing hybridomas using TRIzol Reagent (Ambion).

6)-1-2 Amplification of cDNA Comprising 151D Heavy Chain Variable Region According to 5'-RACE PCR, and Sequencing Thereof cDNA comprising a heavy chain variable region was amplified using approximately 1 μg of the total RNA prepared in Example 6)-1-1 and a SMARTer RACE cDNA Amplification Kit (Clontech).

As primers used to amplify the cDNA of the variable region of a 151D heavy chain gene according to PCR, UPM (Universal Primer A Mix: included with SMARTer RACE cDNA Amplification Kit) and primers designed from the sequences of the constant regions of known rat heavy chains were used.

cDNA comprising the variable region of the heavy chain amplified by 5'-RACE PCR was cloned into a plasmid, and thereafter, the nucleotide sequence of the cDNA of the heavy chain variable region was subjected to sequence analysis.

The determined nucleotide sequence of the cDNA encoding the variable region of the 151D heavy chain is shown in SEQ ID NO: 14, and the amino acid sequence thereof is shown in SEQ ID NO: 15.

6)-1-3 Amplification of cDNA Comprising 151D Light Chain Variable Region According to 5'-RACE PCR, and Sequencing Thereof Amplification and sequencing were carried out by the same method as that applied in Example 6)-1-2. However, as primers used to amplify the cDNA of the variable region of a 151D light chain gene according to PCR, UPM (Universal Primer A Mix: included with SMARTer RACE cDNA Amplification Kit) and primers designed from the sequences of the constant regions of known rat light chains were used.

The determined nucleotide sequence of the cDNA encoding the variable region of the 151D light chain is shown in SEQ ID NO: 16, and the amino acid sequence thereof is shown in SEQ ID NO: 17.

6)-2 Cloning and Sequencing of cDNA of Rat Antibody 198D

The sequences were determined by the same method as that applied in Example 6)-1.

The determined nucleotide sequence of the cDNA encoding the variable region of the 198D heavy chain is shown in SEQ ID NO: 18, and the amino acid sequence thereof is shown in SEQ ID NO: 19. The determined nucleotide sequence of the cDNA encoding the variable region of the 198D light chain is shown in SEQ ID NO: 20, and the amino acid sequence thereof is shown in SEQ ID NO: 21.

6)-3 Production of Human Chimeric Antibody Expression Vector

6)-3-1 Construction of human Chimeric Light Chain Expression Vector pCMA-LK

An approx. 5.4-kb fragment, which had been obtained by digesting a plasmid pcDNA3.3-TOPO/LacZ (Invitrogen) with the restriction enzymes XbaI and PmeI, was bound to a DNA fragment comprising the human light chain signal sequence shown in SEQ ID NO: 22 and a DNA sequence encoding a human κ chain constant region, using an In-Fusion Advantage PCR cloning kit (CLONTECH), to produce pcDNA3.3/LK.

A neomycin expression unit was removed from the pcDNA3.3/LK to construct pCMA-LK.

6)-3-2 Construction of Human Chimeric IgG1 Type Heavy Chain Expression Vector pCMA-G1

A DNA fragment, which had been obtained by digesting pCMA-LK with XbaI and PmeI to remove the light chain signal sequence and the human κ chain constant region therefrom, was bound to a DNA fragment comprising the human heavy chain signal sequence shown in SEQ ID NO: 23 and a DNA sequence encoding the amino acids in a human IgG1 constant region, using an In-Fusion Advantage PCR cloning kit (CLONTECH), to construct pCMA-G1.

6)-3-3 Construction of Human Chimeric 151D Heavy Chain Expression Vector

Using, as a template, the cDNA encoding the variable region of a rat antibody 151D heavy chain obtained in Example 6)-1, PCR was carried out with primers designed for In-fusion cloning, so as to amplify a DNA fragment comprising cDNA encoding the heavy chain variable region. Using an In-Fusion HD PCR cloning kit (Clontech), the amplified DNA fragment was inserted into a site of pCMA-G1 that had been cleaved with the restriction enzyme BlpI, so as to construct a human chimeric 151D heavy chain expression vector.

The nucleotide sequence of the human chimeric 151D heavy chain and the amino acid sequence of this heavy chain are shown in SEQ ID NO: 24 and SEQ ID NO: 25, respectively.

6)-3-4 Construction of Human Chimeric 151D Light Chain Expression Vector

Using, as a template, the cDNA encoding the variable region of a 151D light chain variable region obtained in Example 6)-1, PCR was carried out with primers designed for In-fusion cloning, so as to amplify a DNA fragment comprising cDNA encoding the light chain variable region. Using an In-Fusion HD PCR cloning kit (Clontech), the amplified DNA fragment was inserted into a site of pCMA-LK that had been cleaved with the restriction enzyme BsiWI, so as to construct a human chimeric 151D light chain expression vector.

The nucleotide sequence of the human chimeric 151D light chain and the amino acid sequence of this light chain are shown in SEQ ID NO: 26 and SEQ ID NO: 27, respectively.

6)-3-5 Construction of Human Chimeric 198D Heavy Chain Expression Vector

Using, as a template, the cDNA encoding the variable region of a rat antibody 198D heavy chain obtained in Example 6)-2, a human chimeric 198D heavy chain expression vector was constructed by the same method as that applied in Example 6)-3-3.

The nucleotide sequence of the human chimeric 198D heavy chain and the amino acid sequence of this heavy chain are shown in SEQ ID NO: 28 and SEQ ID NO: 29, respectively.

6)-3-6 Construction of Human Chimeric 198D Light Chain Expression Vector

Using, as a template, the cDNA encoding the variable region of a 198D light chain obtained in Example 6)-2, a human chimeric 198D light chain expression vector was constructed by the same method as that applied in Example 6)-3-4.

The nucleotide sequence of the human chimeric 198D light chain and the amino acid sequence of this light chain are shown in SEQ ID NO: 30 and SEQ ID NO: 31, respectively.

6)-4 Preparation of Human Chimeric Antibody

6)-4-1 Production of Human Chimeric Antibody

In accordance with the manual, FreeStyle 293F cells (Invitrogen) were cultured and passaged. $1 \times 10^8$ FreeStyle 293F cells (Invitrogen) in the logarithmic growth phase were seeded on a 250-mL Fernbach Erlenmeyer Flask (CORNING), and were then diluted with FreeStyle293 expression medium (Invitrogen) at $2.0 \times 10^6$ cells/mL.

Meanwhile, 20 µg of the heavy chain expression vector, 30 µg of the light chain expression vector and 150 µg of Polyethyleneimine (Polyscience #24765) were added to 5 mL of Opti-Pro SFM medium (Invitrogen), and the obtained mixture was gently stirred. After incubation for 5 minutes, the mixture was added to the FreeStyle 293F cells.

The cells were incubated in an incubator (37° C., 8% $CO_2$) with shaking at 125 rpm for 4 hours, and thereafter, 50 mL of EX-CELL VPRO medium (SAFC Biosciences), 0.36 mL of GlutaMAX I (GIBCO), and 2.5 mL of Yeastolate Ultrafiltrate (GIBCO) were added to the culture. The cells were further incubated in an incubator (37° C., 8% $CO_2$) with shaking at 125 rpm for 7 days. The culture supernatant was harvested and filtrated with a 250-mL Filter System (CORNING, #431096).

A human chimeric 151D antibody obtained by the combination of the human chimeric 151D heavy chain expression vector with the human chimeric 151D light chain expression vector was named "c151D," whereas a human chimeric 198D antibody obtained by the combination of the human chimeric 198D heavy chain expression vector with the human chimeric 198D light chain expression vector was named "c198D."

6)-4-2 Purification of Chimeric Antibody

The culture supernatant obtained in Example 6)-4-1 was purified by a one-stage process of rProtein A affinity chromatography. The culture supernatant was applied to a column (manufactured by GE Healthcare Bioscience) that had been filled with MabSelectSuRe equilibrated with PBS, and the column was then washed with PBS in an amount of two or more times the volume of the column. Subsequently, elution was carried out using a 2 M arginine hydrochloride solution (pH 4.0), so that a fraction containing an antibody was collected. This fraction was subjected to Centrifugal UF Filter Device VIVASPIN20 (molecular weight cutoff: UF30K, Sartorius), so that the buffer was replaced with PBS and the antibody was concentrated, thereby adjusting the antibody concentration to 1 mg/mL or more. Finally, the antibody was filtrated through Minisart-Plus filter (Sartorius) to obtain a purified sample.

6)-5 Evaluation of Binding Activity of Human Chimeric Antibody to Human GARP

The dissociation constant between the c151D or c198D produced in Example 6)-4 and human GARP was evaluated by using Biacore T200 (GE Healthcare Bioscience), according to a capture method, which comprises capturing the antibody as a ligand with the immobilized Protein A and then analyzing the dissociation constant using an antigen (recombinant human GARP: R&D Systems) as an analyte. HBS-EP+ (manufactured by GE Healthcare Bioscience) was used as a running buffer, and a Protein A Sensor Chip (manufactured by GE Healthcare Bioscience) was used as a sensor chip.

The human chimeric antibody (1 µg/mL) was added onto the chip at a rate of 10 µL/min for 20 seconds, and a dilution series solution (8 to 128 nM) of the antigen was then added at a flow rate of 30 µl/min for 120 seconds. Subsequently, the dissociation was monitored for 480 seconds. As a regeneration solution, Glycine 1.5 (manufactured by GE Healthcare Bioscience) was added at a flow rate of 20 µl/min for 30 seconds.

1:1 Fitting models were used in data analysis, and the association rate constant ka, the dissociation rate constant kd, and the dissociation constant (KD; KD=kd/ka) were calculated.

The results are shown in Table 1.

Table 1 Dissociation constant between c151D or c198D and human GARP

TABLE 1

|   | Name  | KD (nM) |
|---|-------|---------|
| 1 | c151D | 0.47    |
| 2 | c198D | 0.17    |

Example 7

Production of Humanized Antibody

7)-1 Molecular Modeling of c151D Antibody Variable Region

The molecular modeling of the variable region of the c151D antibody was carried out according to a method that had been generally known as homologous modeling (Methods in Enzymology, 203, 121-153, (1991)).

The primary sequence of the variable region of a human immunoglobulin registered in Protein Data Bank (Nuc. Acid Res.28, 235-242 (2000)) (a three-dimensional structure inferred from an X-ray crystal structure is available) was compared with the variable region of the c151D antibody.

The three-dimensional structure of the variable region was produced by combining, with one another, the coordinates of the heavy chain and light chain of the c151D antibody and a model having high sequence homology to the interfaces, so as to obtain a "framework model."

After that, the representative conformation of each CDR was incorporated into the framework model.

Finally, in order to eliminate atomic contact that was disadvantageous in terms of energy, an energy minimization calculation was carried out. The above described procedures were carried out using Discovery Studio (Dassault Systemes).

7)-2 Design of Amino Acid Sequence of Humanized 151D Antibody

A humanized 151D antibody was constructed according to a method generally known as CDR grafting (Proc. Natl. Acad. Sci. USA 86, 10029-10033 (1989)). An acceptor antibody was selected based on amino acid homology in the framework region.

The sequence of the framework region of the c151D antibody was compared with the framework region of a human subgroup consensus sequence determined by KABAT et al. (Sequences of Proteins of Immunological Interest, 5th Ed. Public Health Service National Institutes of Health, Bethesda, Md. (1991)). As a result, the consensus sequence of human γ chain subgroup 3 and human κ chain subgroup 1 and 4 had high sequence homology, and based on this, they were selected as acceptors.

With regard to the consensus sequence of human γ chain subgroup 3 and the consensus sequences of human κ chain subgroup 1 and human κ chain subgroup 4, the amino acid residues in the framework regions were aligned with the amino acid residues of the c151D antibody, so that the positions, in which different amino acids were used, were identified. The positions of these residues were analyzed using the three-dimensional model of the c151D antibody constructed in the above 7)-1, and donor residues to be grafted onto the acceptor were selected based on the criteria given by Queen et al. (Proc. Natl. Acad. Sci. USA 86, 10029-10033 (1989)).

The thus selected several donor residues were introduced into an acceptor antibody, so as to construct the sequence of humanized h151D as in the manner described in the following examples.

7)-3 Design of Humanized 151D Heavy Chain h151D-H

7)-3-1 h151D-H1 Type Heavy Chain

A humanized 151D heavy chain designed by substituting the arginine residue at amino acid position 35 with a glycine residue, the lysine residue at amino acid position 37 with a leucine residue, the lysine residue at amino acid position 38 with an arginine residue, the serine residue at amino acid position 42 with an alanine residue, the threonine residue at amino acid position 61 with a glycine residue, the glutamine residue at amino acid position 62 with a lysine residue, the alanine residue at amino acid position 68 with a serine residue, the arginine residue at amino acid position 80 with an alanine residue, the alanine residue at amino acid position 94 with a serine residue, the serine residue at amino acid position 96 with an asparagine residue, the aspartic acid residue at amino acid position 103 with an asparagine residue, the serine residue at amino acid position 107 with an alanine residue, the threonine residue at amino acid position 112 with a valine residue, the valine residue at amino acid position 130 with a threonine residue, and the methionine residue at amino acid position 131 with a leucine residue in the c151D heavy chain shown in SEQ ID NO: 25 in the sequence listing, was named "h151D-H1 type heavy chain."

In the nucleotide sequence (SEQ ID NO: 32) encoding the h151D-H1 type heavy chain, the mature heavy chain, from which a signal sequence has been removed, is encoded by the nucleotide sequence consisting of the nucleotides at nucleotide positions 58 to 1398, the variable region is encoded by the nucleotide sequence consisting of the nucleotides at nucleotide positions 58 to 408, and the constant region is encoded by the nucleotide sequence consisting of the nucleotides at nucleotide positions 409 to 1398. The aforementioned variable region has the nucleotide sequence consisting of the nucleotides at nucleotide positions 133 to 162 encoding CDRH1, the nucleotide sequence consisting of the nucleotides at nucleotide positions 205 to 234 encoding CDRH2, and the nucleotide sequence consisting of the nucleotides at nucleotide positions 352 to 375 encoding CDRH3, in SEQ ID NO: 32 in the sequence listing.

In addition, in the amino acid sequence (SEQ ID NO: 33) of the h151D-H1 type heavy chain, the mature heavy chain, from which a signal sequence has been removed, is the amino acid sequence consisting of the amino acids at amino acid positions 20 to 466, the variable region is the amino acid sequence consisting of the amino acids at amino acid positions 20 to 136, and the constant region is the amino acid sequence consisting of the amino acids at amino acid positions 137 to 466. The aforementioned variable region has CDRH1 consisting of the amino acid sequence at amino acid positions 45 to 54 in SEQ ID NO: 33 in the sequence listing, CDRH2 consisting of the amino acid sequence at amino acid positions 69 to 78 therein, and CDRH3 consisting of the amino acid sequence at amino acid positions 118 to 125 therein.

Moreover, the sequences shown in SEQ ID NOS: 32 and 33 are also shown in FIGS. 31 and 21, respectively.

7)-3-2 h151D_H4 Type Heavy Chain

A humanized 151D heavy chain designed by substituting the arginine residue at amino acid position 35 with a glycine residue, the lysine residue at amino acid position 37 with a leucine residue, the lysine residue at amino acid position 38 with an arginine residue, the serine residue at amino acid position 42 with an alanine residue, the threonine residue at amino acid position 61 with a glycine residue, the glutamine residue at amino acid position 62 with a lysine residue, the alanine residue at amino acid position 94 with a serine residue, the aspartic acid residue at amino acid position 103 with an asparagine residue, the serine residue at amino acid position 107 with an alanine residue, the threonine residue at amino acid position 112 with a valine residue, the valine residue at amino acid position 130 with a threonine residue, and the methionine residue at amino acid position 131 with a leucine residue in the c151D heavy chain shown in SEQ ID NO: 25 in the sequence listing, was named "h151D$_{13}$ H4 type heavy chain."

In the nucleotide sequence (SEQ ID NO: 34) encoding the h151D-H4 type heavy chain, the mature heavy chain, from which a signal sequence has been removed, is encoded by the nucleotide sequence consisting of the nucleotides at nucleotide positions 58 to 1398, the variable region is encoded by the nucleotide sequence consisting of the nucleotides at nucleotide positions 58 to 408, and the constant region is encoded by the nucleotide sequence consisting of the nucleotides at nucleotide positions 409 to 1398. The aforementioned variable region has the nucleotide sequence consisting of the nucleotides at nucleotide positions 133 to 162 encoding CDRH1, the nucleotide sequence consisting of the nucleotides at nucleotide positions 205 to 234 encoding CDRH2, and the nucleotide sequence consisting of the nucleotides at nucleotide positions 352 to 375 encoding CDRH3, in SEQ ID NO: 34 in the sequence listing.

In addition, in the amino acid sequence (SEQ ID NO: 35) of the h151D-H4 type heavy chain, the mature heavy chain, from which a signal sequence has been removed, is the amino acid sequence consisting of the amino acids at amino acid positions 20 to 466, the variable region is the amino acid sequence consisting of the amino acids at amino acid positions 20 to 136, and the constant region is the amino acid sequence consisting of the amino acids at amino acid positions 137 to 466. The aforementioned variable region has CDRH1 consisting of the amino acid sequence at amino acid positions 45 to 54 in SEQ ID NO: 35 in the sequence listing, CDRH2 consisting of the amino acid sequence at amino acid positions 69 to 78 therein, and CDRH3 consisting of the amino acid sequence at amino acid positions 118 to 125 therein.

Moreover, the sequences shown in SEQ ID NOS: 34 and 35 are also shown in FIGS. 33 and 23, respectively.

7)-4 Design of Humanized 151D Light Chain h151D_L

7)-4-1 h151D-L1 Type Light Chain

A humanized 151D light chain designed by substituting the threonine residue at amino acid position 29 with an aspartic acid residue, the methionine residue at amino acid position 31 with a leucine residue, the phenylalanine residue at amino acid position 32 with an alanine residue, the isoleucine residue at amino acid position 33 with a valine residue, the valine residue at amino acid position 35 with a leucine residue, the aspartic acid residue at amino acid position 37 with a glutamic acid residue, the valine residue at amino acid position 39 with an alanine residue, the methionine residue at amino acid position 41 with an isoleucine residue, the threonine residue at amino acid position 60 with a proline residue, the threonine residue at amino acid position 83 with a serine residue, the asparagine residue at amino acid position 97 with a serine residue, the methionine residue at amino acid position 98 with a leucine residue, the leucine residue at amino acid position 103 with a valine residue, the threonine residue at amino acid position 120 with a glutamine residue, the leucine residue at amino acid position 124 with a valine residue, the leucine residue at amino acid position 126 with an isoleucine residue, the asparagine residue at amino acid position 127 with a lysine residue, and the alanine residue at amino acid position 129 with a threonine residue in the c151D light chain shown in SEQ ID NO: 27 in the sequence listing, was named "h151D_L1 type light chain."

In the nucleotide sequence (SEQ ID NO: 36) encoding the h151D-L1 type light chain, the mature light chain, from which a signal sequence has been removed, is encoded by the nucleotide sequence consisting of the nucleotides at nucleotide positions 61 to 702, the variable region is encoded by the nucleotide sequence consisting of the nucleotides at nucleotide positions 61 to 387, and the constant region is encoded by the nucleotide sequence consisting of the nucleotides at nucleotide positions 388 to 702. The aforementioned variable region has the nucleotide sequence consisting of the nucleotides at nucleotide positions 130 to 162 encoding CDRH1, the nucleotide sequence consisting of the nucleotides at nucleotide positions 208 to 228 encoding CDRH2, and the nucleotide sequence consisting of the nucleotides at nucleotide positions 325 to 351 encoding CDRH3, in SEQ ID NO: 36 in the sequence listing.

In addition, in the amino acid sequence (SEQ ID NO: 37) of the h151D_L1 type light chain, the mature light chain, from which a signal sequence has been removed, is the amino acid sequence consisting of the amino acids at amino acid positions 21 to 234, the variable region is the amino acid sequence consisting of the amino acids at amino acid positions 21 to 129, and the constant region is the amino acid sequence consisting of the amino acids at amino acid positions 130 to 234. The aforementioned variable region has CDRL1 consisting of the amino acid sequence at amino acid positions 44 to 54 in SEQ ID NO: 37 in the sequence listing, CDRL2 consisting of the amino acid sequence at amino acid positions 70 to 76 therein, and CDRL3 consisting of the amino acid sequence at amino acid positions 109 to 117 therein.

Moreover, the sequences shown in SEQ ID NOS: 36 and 37 are also shown in FIGS. 32 and 22, respectively.

7)-4-2 h151D-L4 Type Light Chain:

A humanized 151D light chain designed by substituting the threonine residue at amino acid position 29 with a serine residue, the methionine residue at amino acid position 31 with a leucine residue, the phenylalanine residue at amino acid position 32 with a serine residue, the isoleucine residue at amino acid position 33 with an alanine residue, the methionine residue at amino acid position 41 with an isoleucine residue, the threonine residue at amino acid position 60 with a proline residue, the glutamine residue at amino acid position 62 with a lysine residue, the threonine residue at amino acid position 83 with a serine residue, the asparagine residue at amino acid position 97 with a serine residue, the methionine residue at amino acid position 98 with a leucine residue, the alanine residue at amino acid position 100 with a proline residue, the leucine residue at amino acid position 103 with a phenylalanine residue, the valine residue at amino acid position 105 with a threonine residue, the threonine residue at amino acid position 120 with a glutamine residue, the leucine residue at amino acid position 124 with a valine residue, the leucine residue at amino acid position 126 with an isoleucine residue, the asparagine residue at amino acid position 127 with a lysine residue, and the alanine residue at amino acid position 129 with a threonine residue in the c151D light chain shown in SEQ ID NO: 27 in the sequence listing, was named "h151D-L4 type light chain."

In the nucleotide sequence (SEQ ID NO: 38) encoding the h151D-L4 type light chain, the mature light chain, from which a signal sequence has been removed, is encoded by the nucleotide sequence consisting of the nucleotides at nucleotide positions 61 to 702, the variable region is encoded by the nucleotide sequence consisting of the nucleotides at nucleotide positions 61 to 387, and the constant region is encoded by the nucleotide sequence consisting of the nucleotides at nucleotide positions 388 to 702. The aforementioned variable region has the nucleotide sequence consisting of the nucleotides at nucleotide positions 130 to 162 encoding CDRL1, the nucleotide sequence consisting of the nucleotides at nucleotide positions 208 to 228 encoding CDRL2, and the nucleotide sequence consisting of the nucleotides at nucleotide positions 325 to 351 encoding CDRL3, in SEQ ID NO: 38 in the sequence listing.

In addition, in the amino acid sequence (SEQ ID NO: 39) of the h151D_L4 type light chain, the mature light chain, from which a signal sequence has been removed, is the amino acid sequence consisting of the amino acids at amino acid positions 21 to 234, the variable region is the amino acid sequence consisting of the amino acids at amino acid positions 21 to 129, and the constant region is the amino acid sequence consisting of the amino acids at amino acid positions 130 to 234. The aforementioned variable region has CDRL1 consisting of the amino acid sequence at amino acid positions 44 to 54 in SEQ ID NO: 39 in the sequence listing, CDRL2 consisting of the amino acid sequence at amino acid positions 70 to 76 therein, and CDRL3 consisting of the amino acid sequence at amino acid positions 109 to 117 therein.

Moreover, the sequences shown in SEQ ID NOS: 38 and 39 are also shown in FIGS. 34 and 24, respectively.

7)-5 Molecular Modeling of Variation Region of c198D

Molecular modeling of the variable region of the c198D antibody was carried out according to a method generally known as homologous modeling (Methods in Enzymology, 203, 121-153, (1991)). The primary sequence of the variable region of a human immunoglobulin registered in Protein Data Bank (Nuc. Acid Res.28, 235-242 (2000)) (a three-dimensional structure inferred from an X-ray crystal structure is available) was compared with the variable region of the c198D antibody.

The three-dimensional structure of the variable region was produced by combining, with one another, the coordinates of the heavy chain and light chain of the c198D antibody and a model having high sequence homology to their interfaces, so as to obtain a "framework model."

After that, the representative conformation of each CDR was incorporated into the framework model.

Finally, in order to eliminate atomic contact that was disadvantageous in terms of energy, an energy minimization calculation was carried out. The above described procedures were carried out using Discovery Studio (Dassault Systemes).

7)-6 Design of Amino Acid Sequence of Humanized 198D

A humanized 198D antibody was constructed according to a method generally known as CDR grafting (Proc. Natl. Acad. Sci. USA 86, 10029-10033 (1989)). An acceptor antibody was selected based on amino acid homology in the framework region.

The sequence of the framework region of the c198D antibody was compared with the framework region of a human subgroup consensus sequence determined by KABAT et al. (Sequences of Proteins of Immunological Interest, 5th Ed. Public Health Service National Institutes of Health, Bethesda, Md. (1991)). As a result, the consensus sequence of human γ chain subgroup 2 and human κ chain subgroup 1 had high sequence homology, and based on this, they ware selected as an acceptor. In addition, several residues in the consensus sequence of human γ chain subgroup 3 were introduced into the acceptor of the heavy chain.

With regard to the consensus sequence of human γ chain subgroup 2 comprising a portion of the consensus sequence of human γ chain subgroup 3 and the consensus sequence of human κ chain subgroup 1, the amino acid residues in the framework regions were aligned with the amino acid residues of the c198D antibody, so that the positions, in which different amino acids were used, were identified. The positions of these residues were analyzed using a three-dimensional model of the c198D antibody constructed in the above 7)-5, and donor residues to be grafted onto the acceptor were selected based on the criteria given by Queen et al. (Proc. Natl. Acad. Sci. USA 86, 10029-10033 (1989)).

The thus selected several donor residues were introduced into the acceptor antibody, so as to construct the sequence of humanized h198D as in the manner described in the following examples.

7)-7 Design of Humanized 198D Heavy Chain h198D-H

7)-7-1 h198D-H3 Type Heavy Chain

A humanized 198D heavy chain designed by substituting the glutamine residue at amino acid position 20 with a glutamic acid residue, the arginine residue at amino acid position 24 with a valine residue, the proline residue at amino acid position 28 with a glycine residue, the glutamine residue at amino acid position 32 with a lysine residue, the glutamic acid residue at amino acid position 61 with a glycine residue, the serine residue at amino acid position 80 with a proline residue, the alanine residue at amino acid position 81 with a serine residue, the leucine residue at amino acid position 86 with a valine residue, the serine residue at amino acid position 87 with a threonine residue, the serine residue at amino acid position 95 with an asparagine residue, the phenylalanine residue at amino acid position 98 with a serine residue, the methionine residue at amino acid position 101 with a leucine residue, the threonine residue at amino acid position 103 with a serine residue, the leucine residue at amino acid position 104 with a valine residue, the glutamine residue at amino acid position 105 with a threonine residue, the threonine residue at amino acid position 106 with an alanine residue, the glutamic acid residue at amino acid position 107 with an alanine residue, the methionine residue at amino acid position 111 with a valine residue, the phenylalanine residue at amino acid position 113 with a tyrosine residue, the alanine residue at amino acid position 133 with a threonine residue, and the serine residue at amino acid position 134 with a leucine residue in the c198D heavy chain shown in SEQ ID NO: 29 in the sequence listing, was named "h198D_H3 type heavy chain."

In the nucleotide sequence (SEQ ID NO: 40) encoding the h198D-H3 type heavy chain, the mature heavy chain, from which a signal sequence has been removed, is encoded by the nucleotide sequence consisting of the nucleotides at nucleotide positions 58 to 1407, the variable region is encoded by the nucleotide sequence consisting of the nucleotides at nucleotide positions 58 to 417, and the constant region is encoded by the nucleotide sequence consisting of the nucleotides at nucleotide positions 418 to 1407. The aforementioned variable region has the nucleotide sequence consisting of the nucleotides at nucleotide positions 130 to 162 encoding CDRH1, the nucleotide sequence consisting of the nucleotides at nucleotide positions 205 to 231 encoding CDRH2, and the nucleotide sequence consisting of the nucleotides at nucleotide positions 349 to 384 encoding CDRH3, in SEQ ID NO: 40 in the sequence listing.

In addition, in the amino acid sequence (SEQ ID NO: 41) of the h198D-H3 type heavy chain, the mature heavy chain, from which a signal sequence has been removed, is the amino acid sequence consisting of the amino acids at amino acid positions 20 to 469, the variable region is the amino acid sequence consisting of the amino acids at amino acid positions 20 to 139, and the constant region is the amino acid sequence consisting of the amino acids at amino acid positions 140 to 469.

Moreover, the sequences shown in SEQ ID NOS: 40 and 41 are also shown in FIGS. 35 and 25, respectively.

7)-8 Design of Humanized 198D Light Chain h198D-L

7)-8-1 h198D-L4 Type Light Chain

A humanized 198D light chain designed by substituting the alanine residue at amino acid position 29 with a serine residue, the glycine residue at amino acid position 33 with an alanine residue, the leucine residue at amino acid position 35 with a valine residue, the glutamic acid residue at amino acid position 37 with an aspartic acid residue, the threonine residue at amino acid position 38 with an arginine residue, the glutamine residue at amino acid position 42 with a threonine residue, the glutamine residue at amino acid position 65 with a lysine residue, the glycine residue at amino acid position 85 with a serine residue, the serine residue at amino acid position 92 with a threonine residue, the lysine residue at amino acid position 94 with a threonine residue, the methionine residue at amino acid position 98 with a leucine residue, the threonine residue at amino acid position 100 with a proline residue, the glutamic acid residue at amino acid position 103 with a phenylalanine residue, the glycine residue at amino acid position 104 with an alanine residue, the valine residue at amino acid position 105 with a threonine residue, the serine residue at amino acid position 120 with a glutamine residue, the leucine residue at amino acid position 124 with a valine residue, and the alanine residue at amino acid position 129 with a threonine residue in the c198D light chain shown in SEQ ID NO: 31 in the sequence listing, was named "h198D-L4 type light chain."

In the nucleotide sequence (SEQ ID NO: 42) encoding the h198D-L4 type light chain, the mature light chain, from which a signal sequence has been removed, is encoded by the nucleotide sequence consisting of the nucleotides at nucleotide positions 61 to 702, the variable region is encoded by the nucleotide sequence consisting of the nucleotides at nucleotide positions 61 to 387, and the constant region is encoded by the nucleotide sequence consisting of the nucleotides at nucleotide positions 388 to 702. The aforementioned variable region has the nucleotide sequence consisting of the nucleotides at nucleotide positions 130 to 162 encoding CDRL1, the nucleotide sequence consisting of the nucleotides at nucleotide positions 208 to 228 encoding CDRL2, and the nucleotide sequence consisting of the nucleotides at nucleotide positions 325 to 351 encoding CDRL3, in SEQ ID NO: 42 in the sequence listing.

In addition, in the amino acid sequence (SEQ ID NO: 43) of the h198D_L4 type light chain, the mature light chain, from which a signal sequence has been removed, is the amino acid sequence consisting of the amino acids at amino acid positions 21 to 234, the variable region is the amino acid sequence consisting of the amino acids at amino acid positions 21 to 129, and the constant region is the amino acid sequence consisting of the amino acids at amino acid positions 130 to 234.

Moreover, the sequences shown in SEQ ID NOS: 42 and 43 are also shown in FIGS. 36 and 26, respectively.

7)-9 Construction of Expression Vector for Humanized Antibody

7)-9-1 Construction of Expression Vector for Humanized Anti-human GARP Antibody h151D-H1L1

A DNA fragment comprising a sequence encoding the h151D-H1 type heavy chain consisting of the nucleotides at nucleotide positions 58 to 1398 of the nucleotide sequence of the h151D-H1 type heavy chain shown in SEQ ID NO: 32 in the sequence listing was synthesized (GENEART, artificial gene synthesis service). Using the synthesized DNA fragment, in accordance with the protocols of Potelligent(R) CHOK1SV Technology by BioWa and Lonza, an expression vector for the h151D-H1 type heavy chain was constructed. The constructed expression vector was named "GSV-h151D-H1."

Subsequently, a DNA fragment comprising a sequence encoding the h151D-L1 type light chain consisting of the nucleotides at nucleotide positions 61 to 702 of the nucleotide sequence of the h151D-L1 type light chain shown in SEQ ID NO: 36 in the sequence listing was synthesized (GENEART, artificial gene synthesis service).

Using the synthesized DNA fragment, in accordance with the protocols of Potelligent(R) CHOK1SV Technology by BioWa and Lonza, an expression vector for the h151D-L1 type light chain was constructed. The constructed expression vector was named "GSV-h151D-L1."

Subsequently, an MACA-1511a expression vector was constructed from the thus constructed expression vectors "GSV-h151D-H1" and "GSV-h151D-L1" in accordance with the protocols of Potelligent(R) CHOK1SV Technology by BioWa and Lonza. The obtained expression vector was named "DGV-h151D-H1L1-GS."

7)-9-2 Construction of Expression Vector for Humanized Anti-human GARP Antibody h151D-H4L4

As in the case of Example 7)-9-1, a DNA fragment comprising a sequence encoding the h151D-H4 type heavy chain consisting of the nucleotides at nucleotide positions 58 to 1398 of the nucleotide sequence of an h151D-H4 type heavy chain shown in SEQ ID NO: 34 in the sequence listing, and a DNA fragment comprising a sequence encoding an h151D-L4 type light chain consisting of the nucleotides at nucleotide positions 61 to 702 of the nucleotide sequence of the h151D-L4 type light chain shown in SEQ ID NO: 38 in the sequence listing, were synthesized (GENEART, artificial gene synthesis service).

Using the synthesized DNA fragments, in accordance with the protocols of Potelligent(R) CHOK1SV Technology by BioWa and Lonza, an MACA-1514a expression vector was constructed. The obtained expression vector was named "DGV-h151D-H4L4-GS."

7)-9-3 Construction of Expression Vector for Humanized Anti-human GARP Antibody h198D-H3L4

As in the case of Example 7)-9-1, a DNA fragment comprising a sequence encoding the h198D-H3 type heavy chain consisting of the nucleotides at nucleotide positions 58 to 1407 of the nucleotide sequence of the h198D-H3 type heavy chain shown in SEQ ID NO: 40 in the sequence listing, and a DNA fragment comprising a sequence encoding the h198D-L4 type light chain consisting of the nucleotides at nucleotide positions 61 to 702 of the nucleotide sequence of the h198D-L4 type light chain shown in SEQ ID NO: 42 in the sequence listing, were synthesized (GENEART, artificial gene synthesis service).

Using the synthesized DNA fragments, in accordance with the protocols of Potelligent(R) CHOK1SV Technology by BioWa and Lonza, an MACA-1983a expression vector was constructed. The obtained expression vector was named "DGV-h198D-H3L4-GS."

7)-10 Preparation of Humanized Anti-human GARP Antibody

7)-10-1 Production of Cells that Produce Humanized Anti-human GARP Antibody

7)-10-1-1 Production of Cells that Produce Humanized Anti-human GARP Antibody h151D-H1L1

Potelligent CHOK1SV cells (BioWa and Lonza) were transfected with the humanized anti-human GARP antibody h151D-H1L1 expression vector, DGV-h151D-H1L1-GS, which had been constructed in Example 7)-9-1 in accordance with the protocols of Potelligent(R) CHOK1SV Technology by BioWa and Lonza, so as to construct a cell line producing the humanized anti-human GARP antibody h151D-H1L1. The obtained producing cell line was named "MAC1-1."

7)-10-1-2 Production of Cells that Produce Humanized Anti-human GARP Antibody h151D-H4L4

As in the case of Example 7)-10-1-1, Potelligent CHOK1SV cells (BioWa and Lonza) were transfected with the humanized anti-human GARP antibody h151D-H4L4 expression vector, DGV-h151D-H4L4-GS, which had been constructed in Example 7)-9-2, so as to construct a cell line producing the humanized anti-human GARP antibody h151D-H4L4. The obtained producing cell line was named "MAC2-1."

7)-10-1-3 Production of Cells that Produce Humanized Anti-human GARP Antibody h198D-H3L4

As in the case of Example 7)-10-1-1, Potelligent CHOK1SV cells (BioWa and Lonza) were transfected with the humanized anti-human GARP antibody h198D-H3L4 expression vector, DGV-h198D-H3L4-GS, which had been constructed in Example 7)-9-3, so as to construct a cell line producing the humanized anti-human GARP antibody h198D-H3L4. The obtained cell line was named "MAC3-1."

7)-10-2 Culture of Cells that Produce Humanized Anti-human GARP Antibody

7)-10-2-1 Culture of Cells that Produce Humanized Anti-human GARP Antibody h151D-H1L1

The humanized anti-human GARP antibody h151D-H1L1-producing cell line "MAC1-1" produced in Example 7)-10-1-1 was cultured using a culture apparatus Wave reactor (GE Healthcare Japan). The producing cell line "MAC1-1" was thawed in Dsp04B (JX Energy) medium, and was then cultured in Dsp04B (JX Energy) medium at 120 rpm in an incubator (37° C., 5% $CO_2$). The obtained culture solution was diluted with C36 (JX Energy) medium, and was then expansively cultured at 120 rpm in an incubator (37° C., 5% $CO_2$).

The obtained culture solution was diluted with the C36 medium at $30 \times 10^4$ cells/mL, and was then transferred into a WAVE CELLBAG (GE Healthcare Bioscience), followed by performing a culture at 37° C. in 5% $CO_2$, at an air-supplying rate of 0.3 L/min, at a rotation rate of 18-24 rpm, at an angle of 6-8°, for 13 days.

From the 3rd day after initiation of the culture, FM4Ae2 medium (self-prepared) was added to the culture in an amount of 6% of the initial culture volume per day. The obtained culture solution was roughly filtrated through a depth filter Millistak MC0HC054H1 (Merck Millipore), and was then filtrated through a 0.22-μm filter (Sartorius) attached to Flexboy Bags. This filtrate was named "MACA-1511a culture supernatant".

7)-10-2-2 Culture of Cells that Produce Humanized Anti-human GARP Antibody h151D-H4L4

In the same manner as that applied in Example 7)-10-2-1, the humanized anti-human GARP antibody h151D-H4L4-producing cell line "MAC2-1" produced in Example 7)-10-1-2 was cultured and expanded, and thereafter, the cells were subjected to fed-batch culture using a culture apparatus Wave reactor (GE Healthcare Japan). The obtained culture was diluted with C36 medium at $30 \times 10^4$ cells/mL, and was then transferred into a WAVE CELLBAG (GE Healthcare Bioscience), followed by performing a culture for 13 days. The obtained culture solution was filtrated, and the obtained filtrate was named "MACA-1514a culture supernatant."

7)-10-2-3 Culture of Cells that Produce Humanized Anti-human GARP Antibody h198D-H3L4

In the same manner as that applied in Example 7)-10-2-1, the humanized anti-human GARP antibody h198D-H3L4-producing cell line "MAC3-1" produced in Example 7)-10-1-3 was cultured and expanded, and thereafter, the cells were subjected to fed-batch culture using a culture apparatus Wave reactor (GE Healthcare Japan). The obtained culture was diluted with C36 medium at $30 \times 10^4$ cells/mL, and was then transferred into a WAVE CELLBAG (GE Healthcare Bioscience), followed by performing a culture for 13 days. The obtained culture solution was filtrated, and the obtained filtrate was named "MACA-1983a culture supernatant."

7)-10-3 Purification of Humanized Anti-human GARP Antibody

7)-10-3-1 Purification of Humanized Anti-human GARP Antibody h151D-H1L1

The "MACA-1511a culture supernatant" obtained in Example 7)-10-2-1 was purified by a three-step process, namely, by rProtein A affinity chromatography, anion exchange chromatography, and cation exchange chromatography.

First, the culture supernatant was applied to rProtein A affinity chromatographic resin that had been equilibrated with PBS. After the entire culture solution had entered the column, the column was washed with PBS, a buffer containing arginine, and PBS. Subsequently, the remaining substance in the column was eluted with an acetate buffer, and an absorption peak at 280 nm was then collected. The collected solution was neutralized with a Tris buffer, and was then roughly filtrated through a glass fiber filter AP20 (Merck Millipore). The solution was filtrated through Stericup-GV (Merck Millipore) that was a 0.22-μm filter, and the resultant filtrate was defined as an rProtein A purified pool.

Subsequently, the rProtein A purified pool was applied to an anion exchange chromatographic resin that had been equilibrated with PBS. After the applied solution as a whole had entered the column, PBS was supplied. A flow-through fraction and the absorption peak at 280 nm at the time of the supply of PBS were collected. The pH of the collected solution was adjusted with acetic acid, and the solution was then roughly filtrated through a glass fiber filter AP20 (Merck Millipore). The solution was filtrated through Stericup-GV (Merck Millipore) that was a 0.22-μm filter, and the resultant filtrate was defined as an AEX purified pool.

Subsequently, the AEX purified pool was applied to a cation exchange chromatographic resin that had been equilibrated with an acetate buffer. After the applied solution as a whole had entered the column, the column was washed with an acetate buffer. Thereafter, elution was carried out using an acetate buffer containing a high concentration of NaCl, and the absorption peak at 280 nm was collected. The collected solution was roughly filtrated through a glass fiber filter AP20 (Merck Millipore), and was then filtrated through Stericup-GV (Merck Millipore) that was a 0.22-μm filter. The resultant filtrate was defined as a CEX purified pool.

The CEX purified pool was concentrated to an antibody concentration of 25 mg/mL with Pellicon 3 Cassette 30 kDa (Merck Millipore), and the buffer was then replaced with a histidine buffer (25 mM Histidine, 5% Sorbitol, pH 6.0). Finally, the solution was roughly filtrated through a glass fiber filter AP20 (Merck Millipore), and was then filtrated through Stericup-GV (Merck Millipore) that was a 0.22-μm filter, so as to obtain a purified sample. This purified sample was named "h151D-H1L1."

7)-10-3-2 Purification of Humanized Anti-human GARP Antibody h151D-H4L4

In the same manner as that applied in Example 7)-10-3-1, the "MACA-1514a culture supernatant" obtained in Example 7)-10-2-2 was purified by a three-stage process, namely, by rProtein A affinity chromatography, anion exchange chromatography, and cation exchange chromatography. The purified sample was named "h151D-H4L4."

7)-10-3-3 Purification of Humanized Anti-human GARP Antibody h198D-H3L4

In the same manner as that applied in Example 7)-10-3-1, the "MACA-1983a culture supernatant" obtained in Example 7)-10-2-3 was purified by a three-stage process, namely, by rProtein A affinity chromatography, anion exchange chromatography, and cation exchange chromatography. The purified sample was named "h198D-H3L4."

7)-11 Evaluation of Binding Activity of Humanized Anti-human GARP Antibodies to Human GARP The dissociation constant between each of the humanized anti-human GARP antibodies h151D-H1L1, h151D-H4L4 and h198D-H3L4 produced in Example 7)-10 and GARP was evaluated by using Biacore T200 (GE Healthcare Bioscience), according to a capture method, which comprises capturing the antibody as a ligand by the immobilized Protein A and then analyzing the dissociation constant using an antigen as an analyte. HBS-EP+(manufactured by GE Healthcare Bioscience) was used as a running buffer, and a Protein A Sensor Chip (manufactured by GE Healthcare Bioscience) was used as a sensor chip.

The human chimeric antibody (1 µg/mL) was added onto the chip at a rate of 10 µL/min for 20 seconds, and a dilution series solution (8 to 128 nM) of the antigen was added at a flow rate of 30 µl/min for 120 seconds. Subsequently, the dissociation was monitored for 480 seconds. As a regeneration solution, Glycine 1.5 (manufactured by GE Healthcare Bioscience) was added at a flow rate of 20 µl/min for 30 seconds.

1:1 Fitting model was used in data analysis, and the association rate constant ka, the dissociation rate constant kd, and the dissociation constant (KD; KD=kd/ka) were calculated.

The results are shown in Table 2.

Table 2 Dissociation Constant of Humanized Anti-human GARP Antibodies

TABLE 2

|   | Name | KD (nM) |
|---|---|---|
| 1 | h151D-H1L1 | 1.8 |
| 2 | h151D-H4L4 | 1.2 |
| 3 | h198D-H3L4 | 0.088 |

Example 8

Binding to Antigen Gene-expressing Cells 8)-1 Binding to GARP

According to the method described in Example 2, an HEK-293T cell suspension, into which a human GARP expression vector or a control vector had been transfected, was prepared. h151D-H1L1, h151D-H4L4, h198D-H3L4, and control human IgG (human IgG: Eureka Therapeutics) were added to the cell suspension, and the cells were incubated at 4° C. for 15 minutes.

The cells were washed twice with FACS buffer (PBS (Invitrogen) supplemented with 3% FBS), and thereafter, R-Phycoerythrin (PE)-labeled anti-IgG antibody (Jackson ImmunoResearch Laboratories) and Horizon FVS450 (Becton Dickinson) were added and suspended. The cells were further incubated at 4° C. for 15 minutes. The flow cytometric analysis was carried out as described in Example 2, and a histogram of PE fluorescence intensity was generated (FIG. 37).

The histograms of fluorescence intensity for h151D-H1L1, h151D-H4L4, and h198D-H3L4 in HEK-293T cells transfected with control vector were similar to the histogram for control IgG (in the figure, the cells are referred to as "Mock vector-transfected HEK-293T").

On the other hand, it was confirmed that the histograms of fluorescence intensity for h151D-H1L1, h151D-H4L4 and h198D_H3L4 shifted to the strong fluorescence intensity side in HEK-293T cells expressing GARP (which are referred to as "hGARP-transfected HEK-293T" in the figure) in comparison to the histogram for control human IgG.

From the aforementioned results, it was found that h151D-H1L1, h151D-H4L4 and h198D-H3L4 specifically bound to GARP.

8)-2 Binding to GARP-TGF β1

8)-2-1 Construction of Human GARP Mutant Expression Vector

Using a human GARP expression vector (Origene) as a template, and also using primer F (cacggcaacctgctggagcggctgctgggggagg) (SEQ ID NO: 44), primer R (caggctgttcccagacaggtccag) (SEQ ID NO: 45), and KOD-Plus-Mutagenesis Kit (Toyobo), YSG at amino acid positions 137-139 in the human GARP amino acid sequence (SEQ ID NO: 1) was converted to HGN, so as to construct a human GARP mutant expression vector. Then, the nucleotide sequence of this vector was confirmed.

8)-2-2 Co-expression of GARP-TGF β1

Using Lipofectamine 2000 (Invitrogen), HEK-293T cells were transfected with a human TGF β1 expression vector (Sino Biological), as well as a human GARP expression vector or a human GARP mutant expression vector.

The cells were cultured in DMEM medium (Invitrogen) supplemented with 10% FBS overnight in 5% $CO_2$ at 37° C., and the cells were then harvested from the plate by treating them with TrypLE Express (Invitrogen). The harvested cells were washed twice with FACS buffer and were re-suspended in the same solution.

The antibodies 105F, h151D-H1L1, h151D-H4L4 and h198D-H3L4 in the present invention, known antibodies (human IgG1 anti-GARP antibodies MHG8 and LHG10 which were produced based on the sequence information described in Patent Literature 1), and control human IgG (Eureka Therapeutics) were added to the cell suspension, and the cells were incubated at 4° C. for 15 minutes.

The cells were washed twice with FACS buffer, and PE-labeled anti-IgG antibody (Jackson ImmunoResearch Laboratories) and Horizon FVS450 (Becton Dickinson) were added and suspended. The cells were further incubated at 4° C. for 15 minutes. The flow cytometric analysis was carried out as described in Example 2, and histograms of PE fluorescence intensity were generated (FIG. 38).

It was confirmed that the histograms for all of the antibodies shifted to the strong fluorescence intensity side in HEK-293T cells co-transfected with TGF β1 and GARP in comparison to the histograms for the control IgG (FIG. 38).

On the other hand, the histograms for MHG8 and LHG10 did not shift and were similar to the histograms for the control IgG in HEK-293T cells co-transfected with TGF β1 and a GARP mutant, whereas the histograms for the antibodies 105F, h151D-H1L1, h151D-H4L4 and h198D-H3L4 shifted to the strong fluorescence intensity side in the cells. Thus, it was demonstrated that the antibodies MHG8 and LHG10 did not bind to the GARP mutant, as described in [Non Patent Literature 12].

From the aforementioned results, it was demonstrated that the antibodies 105F, h151D-H1L1, h151D-H4L4 and h198D-H3L4 bound to both GARP and the GARP mutant on cells co-expressing TGF β1, and it was found that these antibodies bound to regions different from those to which the MHG8 and LHG10 antibodies bound.

Example 9

Binding to Endogenous GARP-expressing Cells

9)-1 Flow Cytometric Analysis Using L428 Cells

L428 cells were washed twice with FACS buffer and suspended in the same solution. Thereafter, h151D-H1L1, h151D-H4L4, h198D_H3L4, and control human IgG (human IgG: Eureka Therapeutics) were added to the suspension, and the cells were incubated at 4° C. for 15 minutes. The cells were washed twice with FACS buffer, and PE-labeled anti-IgG antibody (Jackson ImmunoResearch Laboratories) was added and suspended. The cells were incubated at 4° C. for 15 minutes. Flow cytometric analysis was carried out as described in Example 3, and histograms of PE fluorescence intensity were generated.

As a result, the histograms for the antibodies h151D-H1L1, h151D-H4L4 and h198D_H3L4 shifted to the strong fluorescence intensity side in L428 cells in comparison to the histograms for the control IgG. Thus, it was confirmed that h151D-H1L1, h151D-H4L4 and h198D-H3L4 bound to endogenously expressed GARP (FIG. 39).

9)-2 Flow Cytometric Analysis Using Human Treg

Frozen human PBMC (Cellular Technology) was thawed in accordance with the protocols, and the PBMC was seeded at $2 \times 10^6$ cells/mL in a 24-well plate (Sumitomo Bakelite Co., Ltd.) using RPMI1640 medium (Invitrogen) supplemented with 10% FBS.

Dynabeads Human T-Activator CD3/CD28 (Life technologies) was added to the plate, and the cells were cultured for 48 hours. Thereafter, the cells were suspended in FACS buffer, and the antibodies h151D-H1L1, h151D-H4L4 and h198D-H3L4, and control human IgG (human IgG: Eureka Therapeutics) were added. APC-labeled anti-CD4 antibody (Becton Dickinson) was also added to the suspension. The cells were incubated at 4° C. for 10 minutes.

The cells were washed with FACS buffer, and thereafter, FITC-labeled anti-IgG antibody (Jackson ImmunoResearch Laboratories) and Horizon FVS450 (Becton Dickinson) were added and suspended. The cells were further incubated at 4° C. for 15 minutes.

The cells were washed with FACS buffer again and re-suspended in solution using FoxP3 Staining Buffer Set (Miltenyi Biotec). After that, PE-labeled anti-Foxp3 antibody (Miltenyi Biotec) was added to the cells, and the cells were incubated at 4° C. for 30 minutes.

After the cells were washed, the cells were measured using a flow cytometer (FACS Canto II; Becton Dickinson). CD4-positive cells were analyzed using FlowJo (Tree Star) after dead cells were removed from the analysis by gating out cells stained with Horizon FVS450.

The results demonstrated that the antibodies h151D-H1L1, h151D-H4L4 and h198D-H3L4 bound to FoxP3-positive Treg (FIG. 40).

Example 10

Properties of Anti-GARP Antibody 10)-1 ADCC activity

The antibodies h151D-H1L1, h151D-H4L4 and h198D-H3L4, known antibodies (human IgG1 anti-GARP antibodies MHG8 and LHG10 produced based on the sequence information described in Patent Literature 1), and control human IgG (Sigma) were analyzed for their ADCC activity according to the method described in Example 4.

The antibodies h151D-H1L1, h151D-H4L4 and h198D-H3L4 exhibited cytolytic activity on L428 cells in an antibody concentration-dependent manner (FIG. 41A).

In contrast, as described in Example 4, MHG8 and LHG10 did not exhibit such cytolytic activity in the same way that the control human IgG did not (FIG. 41B).

From the aforementioned results, it was demonstrated that the antibodies h151D-H1L1, h151D-H4L4 and h198D-H3L4 had ADCC activity.

10)-2 Inhibitory Activity to Treg Function

The antibodies h151D-H1L1, h151D-H4L4, and h198D-H3L4 were analyzed for their inhibitory activity to Treg function according to the method described in Example 4. The inhibitory activity of h151D-H1L1, h151D-H4L4, and h198D-H3L4 to Treg function at a final concentration of 1 μg/mL is shown in FIG. 42 (inhibitory rate of h151D-H1L1: 81.5%; inhibitory rate of h151D-H4L4: 80.4%; and inhibitory rate of h198D-H3L4: 70.8%).

It was demonstrated that the antibodies h151D-H1L1, h151D-H4L4, and h198D-H3L4 had inhibitory activity to Treg function.

10)-3 Antitumor Activity (in Vitro)

10)-3-1 Preparation of Cytotoxic T Lymphocytes (CTL)

According to the protocol from Mie University, CTL cells having an NY-ESO-1-specific T cell receptor (MU28 CD8B35 Clone #7: obtained from Mie University) were incubated at $3 \times 10^5$ cells in a 25 cm² flask (Sumitomo Bakelite Co., Ltd.) in the presence of an anti-CD3 antibody (OKT3: Imgenex), IL-2 (Novartis), and feeder cells in RPMI1640 medium (Invitrogen) supplemented with 10% Human male AB serum (Sigma) for 7 days.

With regard to the feeder cells, frozen human PBMC (Cellular Technology) was thawed and CD8-positive cells were removed from the PBMC using CD8 MicroBeads (Miltenyi Biotech) to obtain CD8-depleted PBMC ($7.5 \times 10^6$ cells/25 cm² flask) and the cells were X-ray irradiated. In addition, 103-LCL cells (obtained from Riken BioResource Center) ($1.5 \times 10^6$ cells/25 cm² flask) were also X-ray irradiated by using an X-ray irradiator (Hitachi Medical Corporation). These cells were used as feeder cells.

Treg obtained by the method described in Example 4)-2-1 were added upon initiation of culture ($1.5 \times 10^5$ cells/25 cm² flask) in order to evaluate the suppressive effect of Treg on CTL cell activity. In addition, Treg ($7.5 \times 10^4$ cells/25 cm² flask) obtained by the aforementioned method and the antibodies 105F, h151D-H1L1, h151D-H4L4, h198D-H3L4 and human IgG1 (Enzo) were added upon initiation of culture (10 μg/ml) in order to evaluate the antitumor activity of each antibody.

After completion of the culture, CD8-positive cells were purified and separated to prepare CTL cells using a CD8⁺ T Cell Isolation Kit (Miltenyi Biotech). Thereafter, the prepared CTL cells were used in the evaluation of activity.

10)-3-2 Preparation of Target Cells

A human melanoma cell line, namely, NY-ESO-1-expressing SK-MEL-52 cells (obtained from Mie University: Proc Natl Acad Sci U S A. 1980 July; 77(7): 4260-4) were cultured using RPMI1640 medium (Invitrogen) supplemented with 10% FBS. The labeling of the cells with $^{51}$Cr was carried out as described in Example 4)-1-2, and the cells were adjusted to $2 \times 10^4$ cells/mL. The obtained cells were defined as target cells.

10)-3-3 $^{51}$Cr Release Assay

The target cells were dispensed in a 96-well U-bottom microplate (Costar) (50 μL/well).

Subsequently, CTL cells were added to the plate (100 μL/well), so that the number of CTL cells would be 16, 8, 4, or 2 times more than the number of target cells (CTL cells: target cells=16:1, 8:1, 4:1, or 2:1), and the cells were incubated in 5% $CO_2$ at 37° C. for 4 hours. After that, the cells were processed according to the method as described in Example 4)-1-3. It is to be noted that the inhibitory activity of a sample is calculated every time in each experiment. In addition, it was confirmed that the CTL cells do not exhibit cytolytic activity to cells that do not express NY-ESO-1.

The measurement results are shown in FIGS. 43 and 44.

The cytolytic activity of the CTL cells to SK-MEL-52 was suppressed by Treg (FIG. 43).

On the other hand, the cell lysis rates of CTL cells against SK-MEL-52 cells elevated as the number of the CTL cells increased in the CTL cells to which the antibodies 105F, h151D-H1L1, h151D-H4L4, or h198D-H3L4 had been added, and also, the cell lysis rates were clearly higher than that of the control CTL cells to which the control IgG had been added (FIG. 44) at any target-effector ratio.

Therefore, it was demonstrated that the antibodies 105F, h151D-H1L1, h151D-H4L4 and h198D-H3L4 inhibited the suppressive activity of Treg to CTL cells, and enhanced antitumor activity.

10)-4 Antitumor Activity (in Vivo)

It is known that the antitumor effects of a chimeric antibody having ADCC activity can be evaluated in NOD/Shi-scid, IL-2R $^{null}$ (NOG) mice into which L428 cells had been transplanted and human PBMC are administered (J Immunol. 2009 Oct. 1; 183(7): 4782-91).

L428 cells (DSMZ), which had been suspended in a mixed solution of RPMI1640 medium (Invitrogen) and Matrigel (Becton Dickinson) (1:1) at $1\times10^7$ cells/mL, were transplanted in an volume of 0.1 mL into the subcutis of the axillary region of NOG mice (female, In vivo science). The day at which the L428 cells were transplanted was defined as Day 0. On Day 6, the mice were divided into groups based on the tumor volume value (n=6 in each group), and the groups of administration were set as follows.

PBS control 1: administered on Days 6, 10, 14, 18, 22 and 26, and also, human PBMC (Lot: 20140707) was administered on Days 6, 14 and 22

105F antibody: administered at a dose of 5 mg/kg on Days 6, 10, 14, 18, 22 and 26, and also, human PBMC (Lot: 20140707) was administered on Days 6, 14 and 22

PBS control 2: administered on Days 6, 10, 14, 18, 22, and also, human PBMC (Lot: 20150924) was administered on Days 6, 14 and 22 h151D-H1L1 antibody: administered at a dose of 1 mg/kg on Days 6, 10, 14, 18 and 22, and also, human PBMC (Lot: 20150924) was administered on Days 6, 14 and 22 h151D-H4L4 antibody: administered at a dose of 1 mg/kg on Days 0, 6, 10, 14, 18 and 22, and also, human PBMC (Lot: 20150924) was administered on Days 6, 14 and 22 h198D-H3L4 antibody: administered at a dose of 1 mg/kg on Days 0, 6, 10, 14, 18 and 22, and also, human PBMC (Lot: 20150924) was administered on Days 6, 14 and 22

Each antibody was diluted with PBS (Invitrogen) and administered to the mice through the tail vein (10 mL/kg).

Regarding human PBMC, frozen human PBMC (Cellular Technology) was thawed in accordance with the protocols and prepared at $1\times10^7$ cells/mL. The prepared cells (0.2 mL) were administered to the mice through the tail vein.

The long diameter (mm) and short diameter (mm) of tumor were measured over time, using electronic digital calipers (Mitutoyo), and the volume of the tumor was then calculated according to the following expression.

Tumor volume (mm3)=½×[long diameter of tumor]× [short diameter of tumor]×[short diameter of tumor]

A change in the mean value±standard error (SE) of the tumor volume in each group is shown in FIG. 45.

The antibodies 105F, h151D-H1L1, h151D-H4L4 and h198D-H3L4 exhibited antitumor activity to the L428 cells, in comparison to the control group to which only PBMC was administered. Thus, a significant difference was observed with respect to the control group (105F: t-test; and h151D-H1L1, h151D-H4L4 and h198D-H3L4: Dunnett's multiple comparison test). The results of the significant difference test (P values) on the final measurement day of individual groups (105F: Day 31; and h151D-H1L1, h151D-H4L4 and h198D-H3L4: Day 25) are also shown in the figure.

Therefore, the antibodies 105F, h151D-H1L1, h151D-H4L4 and h198D-H3L4 exhibited antitumor activity in in vivo models.

Example 11

Epitope Analysis of Anti-GARP Antibody

The epitopes of anti-human GARP antibodies (105F, 110F, h151D-H1L1, and h198D-H3L4) were analyzed by hydrogen-deuterium exchange mass spectrometry.

A 7 mg/mL anti-human GARP antibody was mixed with 3 mg/mL human GARP (R&D Systems) or a blank buffer in equal amounts. To the obtained solution, 9 equivalents of light water or heavy water was added. After 30 seconds, 480 seconds, or 6000 seconds of the addition of the water, or after one night had passed, 100 mM phosphoric acid, 4 M Gdn-HCl and 150 mM TCEP (pH 2.5) were added in equal amounts to the sample, so that the obtained mixture was then subjected to deuterium substitution. The thus deuterium—substituted sample was injected into HPLC under cooling, and it was then supplied to an immobilized pepsin column with a 0.1% TFA solution.

A peptide fragment obtained by digestion of human GARP in the pepsin column was retained in a C18 trap column, was then eluted by linear gradient of water and acetonitrile to which 0.1% formic acid and 0.025% TFA had been added, and was then separated in a C18 analysis column. The separated peptide fragment was subjected to mass spectrometry using a time-of-flight mass spectrometer.

The deuterium substitution rate was calculated from the mass of each peptide. A peptide fragment, in which a significant reduction in the deuterium substitution rate was observed as a result of addition of the anti-human GARP antibody, was identified to be an epitope fragment.

In the case of 105F, suppression of the deuterium substitution rate was found in the amino acid residues at positions 366-377, 407-445, and 456-470 of the human GARP shown in SEQ ID NO: 1, and thus, they were identified to be an epitope.

In the case of 110F, suppression of the deuterium substitution rate was found in the amino acid residues at positions 54-112 and 366-392 of the human GARP shown in SEQ ID NO: 1, and thus, they were identified to be an epitope.

In the case of h151D-H1L1, suppression of the deuterium substitution rate was found in the amino acid residues at positions 352-392 of the human GARP shown in SEQ ID NO: 1, and thus, they were identified to be an epitope.

In the case of h198D-H3L4, suppression of the deuterium substitution rate was found in the amino acid residues at positions 18-112 of the human GARP shown in SEQ ID NO: 1, and thus, they were identified to be an epitope.

INDUSTRIAL APPLICABILITY

The anti-GARP antibody of the present invention has an antitumor activity caused by inhibitory activity to Treg function, which is mediated by an ADCC activity, and thus, a pharmaceutical composition comprising the anti-GARP antibody can be used as an anticancer agent.

Moreover, the excessive presence of Treg and the activation thereof in patients having malaria and HIV infection exhibit a correlation with the disease state, and the removal of Treg induces remission of each disease in murine models for the diseases. Accordingly, it can be expected that effective inhibition of Treg function will also have therapeutic effects on refractory infections such as malaria and HIV.

SEQUENCE LISTING FREE TEXT

SEQ ID NO: 1—Amino acid sequence of GARP
SEQ ID NO: 2—Amino acid sequence of 105F antibody heavy chain
SEQ ID NO: 3—Amino acid sequence of 105F antibody light chain
SEQ ID NO: 4—Amino acid sequence of 110F antibody heavy chain
SEQ ID NO: 5—Amino acid sequence of 110F antibody light chain
SEQ ID NO: 6—Nucleotide sequence of 105F antibody heavy chain
SEQ ID NO: 7—Nucleotide sequence of 105F antibody light chain
SEQ ID NO: 8—Nucleotide sequence of 110F antibody heavy chain
SEQ ID NO: 9—Nucleotide sequence of 110F antibody light chain
SEQ ID NO: 10—Primer A
SEQ ID NO: 11—Primer B
SEQ ID NO: 12—Primer C
SEQ ID NO: 13—Primer D
SEQ ID NO: 149—Nucleotide sequence of cDNA encoding variable region of 151D heavy chain
SEQ ID NO: 15—Amino acid sequence of variable region of 151D heavy chain
SEQ ID NO: 16—Nucleotide sequence of cDNA encoding variable region of 151D light chain
SEQ ID NO: 17—Amino acid sequence of variable region of 151D light chain
SEQ ID NO: 18—Nucleotide sequence of cDNA encoding variable region of 198D heavy chain
SEQ ID NO: 19—Amino acid sequence of variable region of 198D heavy chain
SEQ ID NO: 20—Nucleotide sequence of cDNA encoding variable region of 198D light chain
SEQ ID NO: 21—Amino acid sequence of variable region of 198D light chain
SEQ ID NO: 22—Nucleotide sequence of DNA fragment comprising human light chain signal sequence and sequence encoding amino acids in human κ chain constant region
SEQ ID NO: 23—Nucleotide sequence of DNA fragment comprising human heavy chain signal sequence and sequence encoding amino acids in human IgG1 constant region
SEQ ID NO: 24—Nucleotide sequence of human chimeric antibody c151D heavy chain
SEQ ID NO: 25—Amino acid sequence of human chimeric antibody c151D heavy chain
SEQ ID NO: 26—Nucleotide sequence of human chimeric antibody c151D light chain
SEQ ID NO: 27—Amino acid sequence of human chimeric antibody c151D light chain
SEQ ID NO: 28—Nucleotide sequence of human chimeric antibody c198D heavy chain
SEQ ID NO: 29—Amino acid sequence of human chimeric antibody c198D heavy chain
SEQ ID NO: 30—Nucleotide sequence of human chimeric antibody c198D light chain
SEQ ID NO: 31—Amino acid sequence of human chimeric antibody c198D light chain
SEQ ID NO: 32—Nucleotide sequence of humanized antibody h151D-H1
SEQ ID NO: 33—Amino acid sequence of humanized antibody h151D-H1
SEQ ID NO: 34—Nucleotide sequence of humanized antibody h151D-H4
SEQ ID NO: 35—Amino acid sequence of humanized antibody h151D-H4
SEQ ID NO: 36—Nucleotide sequence of humanized antibody h151D-L1
SEQ ID NO: 37—Amino acid sequence of humanized antibody h151D-L1
SEQ ID NO: 38—Nucleotide sequence of humanized antibody h151D-L4
SEQ ID NO: 39—Amino acid sequence of humanized antibody h151D-L4
SEQ ID NO: 40—Nucleotide sequence of humanized antibody h198D-H3
SEQ ID NO: 41—Amino acid sequence of humanized antibody h198D-H3
SEQ ID NO: 42—Nucleotide sequence of humanized antibody h198D-L4
SEQ ID NO: 43—Amino acid sequence of humanized antibody h198D-L4
SEQ ID NO: 44—Primer F
SEQ ID NO: 45—Primer R

The invention claimed is:

1. An antibody that specifically binds Glycoprotein-A Repetitions Predominant (GARP) comprising,
   a) CDRH1 consisting of the amino acid sequence at amino acid positions 45 to 54 of SEQ ID NO: 25,
   b) CDRH2 consisting of the amino acid sequence at amino acid positions 69 to 78 of SEQ ID NO: 25,
   c) CDRH3 consisting of the amino acid sequence at amino acid positions 118 to 125 of SEQ ID NO: 25,
   d) CDRL1 consisting of the amino acid sequence at amino acid positions 44 to 54 of SEQ ID NO: 27,
   e) CDRL2 consisting of the amino acid sequence at amino acid positions 70 to 76 of SEQ ID NO: 27 and
   f) CDRL3 consisting of the amino acid sequence at amino acid positions 109 to 117 of SEQ ID NO: 27.

2. The antibody of claim 1, wherein the GARP is a molecule consisting of the amino acid sequence of SEQ ID NO: 1.

3. The antibody of claim 1, comprising:
   a heavy chain variable region consisting of the amino acid sequence at amino acid positions 20 to 136 of SEQ ID NO: 25, and a light chain variable region consisting of the amino acid sequence at amino acid positions 21 to 129 of SEQ ID NO: 27.

4. The antibody of claim 1, comprising a human constant region.

5. The antibody of claim 1, comprising a heavy chain consisting of the amino acid sequence at amino acid positions 20 to 466 of SEQ ID NO: 25, and a light chain consisting of the amino acid sequence at amino acid positions 21 to 234 of SEQ ID NO: 27.

6. The antibody of claim 1 which is humanized.

7. The antibody of claim 6, comprising:
   a heavy chain variable region consisting of an amino acid sequence selected from the group consisting of:
   (a) the amino acid sequence at amino acid positions 20 to 136 of SEQ ID NO: 33,
   (b) the amino acid sequence at amino acid positions 20 to 136 of SEQ ID NO: 35,
   (c) an amino acid sequence having homology of at least 95% or more to the sequence of (a) or (b), and
   (d) an amino acid sequence comprising a substitution of one or more amino acids in the sequence of a framework region other than at each CDR sequence in the sequence of (a) or (b), and
   a light chain variable region consisting of an amino acid sequence selected from the group consisting of:
   (e) the amino acid sequence at amino acid positions 21 to 129 of SEQ ID NO: 37,
   (f) the amino acid sequence at amino acid positions 21 to 129 of SEQ ID NO: 39,
   (g) an amino acid sequence having homology of at least 95% or more to the sequence of (e) or (f), and
   (h) an amino acid sequence comprising a substitution of one or more amino acids in the sequence of a framework region other than at each CDR sequence in the sequence of (e) or (f).

8. The antibody of claim 6, comprising:
   (1) a heavy chain variable region consisting of the amino acid sequence at amino acid positions 20 to 136 of SEQ ID NO: 33, and a light chain variable region consisting of the amino acid sequence at amino acid positions 21 to 129 of SEQ ID NO: 37, or
   (2) a heavy chain variable region consisting of the amino acid sequence at amino acid positions 20 to 136 of SEQ ID NO: 35, and a light chain variable region consisting of the amino acid sequence at amino acid positions 21 to 129 of SEQ ID NO: 39.

9. The antibody of claim 6, comprising:
   (1) a heavy chain selected from the group consisting of a heavy chain having the amino acid sequence at amino acid positions 20 to 466 of SEQ ID NO: 33, and a heavy chain having the amino acid sequence at amino acid positions 20 to 466 of SEQ ID NO: 35, and
   (2) a light chain selected from the group consisting of a light chain having the amino acid sequence at amino acid positions 21 to 234 of SEQ ID NO: 37, and a light chain having the amino acid sequence at amino acid positions 21 to 234 of SEQ ID NO: 39.

10. The antibody of claim 6, comprising:
   (1) a heavy chain having the amino acid sequence at amino acid positions 20 to 466 of SEQ ID NO: 33, and a light chain having the amino acid sequence at amino acid positions 21 to 234 of SEQ ID NO: 37, or (2) a heavy chain having the amino acid sequence at amino acid positions 20 to 466 of SEQ ID NO: 35, and a light chain having the amino acid sequence at amino acid positions 21 to 234 of SEQ ID NO: 39.

11. The antibody of claim 10, comprising one or two or more modifications selected from the group consisting of N-linked glycosylation, O-linked glycosylation, N-terminal processing, C-terminal processing, deamidation, isomerization of aspartic acid, oxidation of methionine, addition of a methionine residue to the N-terminus, amidation of a proline residue, and a deletion of one or two amino acids at the carboxyl terminus of the heavy chain.

12. The antibody of claim 11, wherein one or two amino acids are deleted at the carboxyl terminus of the heavy chain.

13. The antibody of claim 11, wherein a proline residue at the carboxyl terminus of the heavy chain is further amidated.

14. The antibody of claim 10, wherein sugar chain modification is regulated in order to enhance antibody-dependent cellular cytotoxicity.

15. A pharmaceutical composition comprising an antibody of claim 1.

16. A method for treating a tumor overexpressing GARP in an individual, which comprises administering an antibody of claim 1 to the individual.

17. The method of claim 16, wherein the tumor is a cancer.

18. The method of claim 17, wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

19. An antibody that specifically binds Glycoprotein-A Repetitions Predominant (GARP) comprising, a heavy chain having the amino acid sequence at amino acid positions 20 to 466 of SEQ ID NO: 33, and a light chain having the amino acid sequence at amino acid positions 21 to 234 of SEQ ID NO: 37.

20. The antibody of claim 19, wherein sugar chain modification is regulated in order to enhance antibody-dependent cellular cytotoxicity.

21. The antibody of claim 20, wherein one or two amino acids are deleted at the carboxyl terminus of the heavy chain.

22. An antibody that specifically binds Glycoprotein-A Repetitions Predominant (GARP) comprising, a heavy chain having the amino acid sequence at amino acid positions 20 to 466 of SEQ ID NO: 35, and a light chain having the amino acid sequence at amino acid positions 21 to 234 of SEQ ID NO: 39.

23. The antibody of claim 22, wherein sugar chain modification is regulated in order to enhance antibody-dependent cellular cytotoxicity.

24. The antibody of claim 23, wherein one or two amino acids are deleted at the carboxyl terminus of the heavy chain.

25. A method for treating a tumor overexpressing GARP in an individual, which comprises administering an antibody of claim 19 to the individual.

26. The method of claim 25, wherein the tumor is a cancer.

27. The method of claim 26, wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

28. A method for treating a tumor overexpressing GARP in an individual, which comprises administering an antibody of claim 20 to the individual.

29. The method of claim 28, wherein the tumor is a cancer.

30. The method of claim 29, wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

31. A method for treating a tumor overexpressing GARP in an individual, which comprises administering an antibody of claim 21 to the individual.

32. The method of claim 31, wherein the tumor is a cancer.

33. The method of claim 32, wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

34. A method for treating a tumor overexpressing GARP in an individual, which comprises administering an antibody of claim 22 to the individual.

35. The method of claim 34, wherein the tumor is a cancer.

36. The method of claim 35, wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

37. A method for treating a tumor overexpressing GARP in an individual, which comprises administering an antibody of claim 23 to the individual.

38. The method of claim 37, wherein the tumor is a cancer.

39. The method of claim 38, wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

40. A method for treating a tumor overexpressing GARP in an individual, which comprises administering an antibody of claim 24 to the individual.

41. The method of claim 40, wherein the tumor is a cancer.

42. The method of claim 41, wherein the cancer is lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, esophageal cancer, or blood cancer.

43. A pharmaceutical composition comprising an antibody of claim 19.

44. A pharmaceutical composition comprising an antibody of claim 20.

45. A pharmaceutical composition comprising an antibody of claim 21.

46. A pharmaceutical composition comprising an antibody of claim 22.

47. A pharmaceutical composition comprising an antibody of claim 23.

48. A pharmaceutical composition comprising an antibody of claim 24.

\* \* \* \* \*

SEQUENCE LISTING

```
<160> NUMBER OF SEQ ID NOS: 45

<210> SEQ ID NO 1
<211> LENGTH: 662
<212> TYPE: PRT
<213> ORGANISM: Human

<400> SEQUENCE: 1

Met Arg Pro Gln Ile Leu Leu Leu Ala Leu Leu Thr Leu Gly Leu
```

```
1               5                   10                  15
Ala Ala Gln His Gln Asp Lys Val Pro Cys Lys Met Val Asp Lys Lys
                20                  25                  30

Val Ser Cys Gln Val Leu Gly Leu Leu Gln Val Pro Ser Val Leu Pro
                35                  40                  45

Pro Asp Thr Glu Thr Leu Asp Leu Ser Gly Asn Gln Leu Arg Ser Ile
50                              55                  60

Leu Ala Ser Pro Leu Gly Phe Tyr Thr Ala Leu Arg His Leu Asp Leu
65                  70                  75                  80

Ser Thr Asn Glu Ile Ser Phe Leu Gln Pro Gly Ala Phe Gln Ala Leu
                85                  90                  95

Thr His Leu Glu His Leu Ser Leu Ala His Asn Arg Leu Ala Met Ala
                100                 105                 110

Thr Ala Leu Ser Ala Gly Gly Leu Gly Pro Leu Pro Arg Val Thr Ser
                115                 120                 125

Leu Asp Leu Ser Gly Asn Ser Leu Tyr Ser Gly Leu Leu Glu Arg Leu
                130                 135                 140

Leu Gly Glu Ala Pro Ser Leu His Thr Leu Ser Leu Ala Glu Asn Ser
145                 150                 155                 160

Leu Thr Arg Leu Thr Arg His Thr Phe Arg Asp Met Pro Ala Leu Glu
                165                 170                 175

Gln Leu Asp Leu His Ser Asn Val Leu Met Asp Ile Glu Asp Gly Ala
                180                 185                 190

Phe Glu Gly Leu Pro Arg Leu Thr His Leu Asn Leu Ser Arg Asn Ser
                195                 200                 205

Leu Thr Cys Ile Ser Asp Phe Ser Leu Gln Gln Leu Arg Val Leu Asp
                210                 215                 220

Leu Ser Cys Asn Ser Ile Glu Ala Phe Gln Thr Ala Ser Gln Pro Gln
225                 230                 235                 240

Ala Glu Phe Gln Leu Thr Trp Leu Asp Leu Arg Glu Asn Lys Leu Leu
                245                 250                 255

His Phe Pro Asp Leu Ala Ala Leu Pro Arg Leu Ile Tyr Leu Asn Leu
                260                 265                 270

Ser Asn Asn Leu Ile Arg Leu Pro Thr Gly Pro Pro Gln Asp Ser Lys
                275                 280                 285

Gly Ile His Ala Pro Ser Glu Gly Trp Ser Ala Leu Pro Leu Ser Ala
                290                 295                 300

Pro Ser Gly Asn Ala Ser Gly Arg Pro Leu Ser Gln Leu Leu Asn Leu
305                 310                 315                 320

Asp Leu Ser Tyr Asn Glu Ile Glu Leu Ile Pro Asp Ser Phe Leu Glu
                325                 330                 335

His Leu Thr Ser Leu Cys Phe Leu Asn Leu Ser Arg Asn Cys Leu Arg
                340                 345                 350

Thr Phe Glu Ala Arg Arg Leu Gly Ser Leu Pro Cys Leu Met Leu Leu
                355                 360                 365

Asp Leu Ser His Asn Ala Leu Glu Thr Leu Glu Leu Gly Ala Arg Ala
                370                 375                 380

Leu Gly Ser Leu Arg Thr Leu Leu Leu Gln Gly Asn Ala Leu Arg Asp
385                 390                 395                 400

Leu Pro Pro Tyr Thr Phe Ala Asn Leu Ala Ser Leu Gln Arg Leu Asn
                405                 410                 415

Leu Gln Gly Asn Arg Val Ser Pro Cys Gly Gly Pro Asp Glu Pro Gly
                420                 425                 430
```

Pro Ser Gly Cys Val Ala Phe Ser Gly Ile Thr Ser Leu Arg Ser Leu
        435                 440                 445

Ser Leu Val Asp Asn Glu Ile Glu Leu Leu Arg Ala Gly Ala Phe Leu
450                 455                 460

His Thr Pro Leu Thr Glu Leu Asp Leu Ser Ser Asn Pro Gly Leu Glu
465                 470                 475                 480

Val Ala Thr Gly Ala Leu Gly Gly Leu Glu Ala Ser Leu Glu Val Leu
                485                 490                 495

Ala Leu Gln Gly Asn Gly Leu Met Val Leu Gln Val Asp Leu Pro Cys
            500                 505                 510

Phe Ile Cys Leu Lys Arg Leu Asn Leu Ala Glu Asn Arg Leu Ser His
        515                 520                 525

Leu Pro Ala Trp Thr Gln Ala Val Ser Leu Glu Val Leu Asp Leu Arg
530                 535                 540

Asn Asn Ser Phe Ser Leu Leu Pro Gly Ser Ala Met Gly Gly Leu Glu
545                 550                 555                 560

Thr Ser Leu Arg Arg Leu Tyr Leu Gln Gly Asn Pro Leu Ser Cys Cys
                565                 570                 575

Gly Asn Gly Trp Leu Ala Ala Gln Leu His Gln Gly Arg Val Asp Val
            580                 585                 590

Asp Ala Thr Gln Asp Leu Ile Cys Arg Phe Ser Ser Gln Glu Glu Val
        595                 600                 605

Ser Leu Ser His Val Arg Pro Glu Asp Cys Glu Lys Gly Gly Leu Lys
610                 615                 620

Asn Ile Asn Leu Ile Ile Leu Thr Phe Ile Leu Val Ser Ala Ile
625                 630                 635                 640

Leu Leu Thr Thr Leu Ala Ala Cys Cys Cys Val Arg Arg Gln Lys Phe
                645                 650                 655

Asn Gln Gln Tyr Lys Ala
            660

<210> SEQ ID NO 2
<211> LENGTH: 448
<212> TYPE: PRT
<213> ORGANISM: Human

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Gln Leu Ala Glu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly

-continued

```
                130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 3
<211> LENGTH: 217
<212> TYPE: PRT
<213> ORGANISM: Human

<400> SEQUENCE: 3

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
                35                  40                  45

Leu Ile Tyr Ala Asp Thr Asn Arg Pro Ser Gly Val Pro Asp Arg Phe
                50                  55                  60
```

-continued

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Gln Ser Tyr Asp Ser Ser
                 85                  90                  95

Leu Arg Gly Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 4
<211> LENGTH: 453
<212> TYPE: PRT
<213> ORGANISM: Human

<400> SEQUENCE: 4

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
         35                 40                  45

Ala Gly Ile Ser Trp Asn Ser Ala Ile Thr Val Tyr Ala Asp Ser Val
 50                 55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
             85                 90                  95

Ala Lys Asp Ala Gly Gly Arg Tyr Ser Gly Ser Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

```
Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 5
<211> LENGTH: 216
<212> TYPE: PRT
<213> ORGANISM: Human

<400> SEQUENCE: 5

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Arg Ser
                85                  90                  95

Leu Asn Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
```

```
                    130                 135                 140
Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 6
<211> LENGTH: 1344
<212> TYPE: DNA
<213> ORGANISM: Human

<400> SEQUENCE: 6

```
gaggtgcagc tgttggagtc tgggggaggc ttggtacagc ctggggggtc cctgagactc      60
tcctgtgcag cctctggatt caccttcagt gactactaca tgagctggat ccgccaggct     120
ccaggcaagg ggctggagtg ggtatcgggt gttagttgga atggcagtag gacgcactat     180
gcagactctg tgaagggccg attcaccatc tccagagaca attccaagaa cacgctgtat     240
ctgcaaatga acagcctgag agccgaggac actgccgtgt attactgtgc cagacagagg     300
cagctggctg aatttgacta ctggggccaa ggtaccctgg tcaccgtgag ctcagcctcc     360
accaagggcc caagcgtctt ccccctggca ccctcctcca gagcacctc tggcggcaca      420
gccgccctgg gctgcctggt caaggactac ttccccgaac cgtgaccgt gagctggaac      480
tcaggcgccc tgaccagcgg cgtgcacacc ttccccgctg tcctgcagtc ctcaggactc     540
tactccctca gcagcgtggt gaccgtgccc tccagcagct gggcaccca gacctacatc      600
tgcaacgtga atcacaagcc cagcaacacc aaggtggaca gagagttga gcccaaatct      660
tgtgacaaaa ctcacacatg cccaccctgc ccagcacctg aactcctggg gggaccctca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagcccgg aggagcagta caacagcacg       900
taccgggtgg tcagcgtcct caccgtcctg caccaggact ggctgaatgg caaggagtac     960
aagtgcaagg tctccaacaa agccctccca gcccccatcg agaaaaccat ctccaaagcc    1020
aaaggccagc cccgggaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gcccgagaac aactacaaga ccacccctcc cgtgctggac    1200
tccgacggct ccttcttcct ctacagcaag ctcaccgtgg acaagagcag gtggcagcag    1260
ggcaacgtct tctcatgctc cgtgatgcat gaggctctgc acaaccacta cacccagaag    1320
agcctctccc tgtctcccgg caaa                                           1344
```

<210> SEQ ID NO 7
<211> LENGTH: 651
<212> TYPE: DNA
<213> ORGANISM: Human

<400> SEQUENCE: 7

| | |
|---|---|
| cagtctgtgc tgactcagcc accctcagcg tctgggaccc ccgggcagag ggtcaccatc | 60 |
| tcctgcactg ggagcagctc caacattggg gcgggttatg ttgtacattg gtatcagcag | 120 |
| ctcccaggaa cggcccccaa actcctcatc tatgctgaca ccaatcggcc ctcaggggtc | 180 |
| cctgaccgat tctctggctc caagtctggc acctcagcct ccctggccat cagtgggctc | 240 |
| cggtccgagg atgaggctga ttattactgc cagtcctatg acagcagcct gagaggttgg | 300 |
| gtgttcggcg gaggaaccaa gctgacggtc ctaggtcagc ctaaggctgc cctagcgtg | 360 |
| accctgttcc ctccttccag cgaggagctt caagctaaca aggccaccct ggtgtgtctt | 420 |
| atctctgact ctaccctgg cgctgtgacc gtggcctgga aggctgacag ctcccctgtg | 480 |
| aaggccggag tggagaccac cacacctagc aagcagtcta caacaagta cgctgccagc | 540 |
| tcctacctga gccttacccc tgagcagtgg aagtctcaca gaagctactc ctgtcaagtg | 600 |
| acccacgagg gcagcaccgt ggagaagacc gtggctccta ccgagtgttc c | 651 |

<210> SEQ ID NO 8
<211> LENGTH: 1359
<212> TYPE: DNA
<213> ORGANISM: Human

<400> SEQUENCE: 8

| | |
|---|---|
| gaggtgcagc tgttggagtc tggggggaggc ttggtacagc ctgggggggtc cctgagactc | 60 |
| tcctgtgcag cctctggatt caccttcagt agctatggca tgcactgggt ccgccaggct | 120 |
| ccaggcaagg ggctggagtg ggtcgccgga attagttgga acagtgccat cacagtctat | 180 |
| gcggactctg tgaagggccg gttcaccatc tccagagaca attccaagaa cacgctgtat | 240 |
| ctgcaaatga acagcctgag agccgaggac actgccgtgt attactgtgc aaaagatgcc | 300 |
| gggggccggt atagtgggag ctactacttt gactactggg gccaaggtac cctggtcacc | 360 |
| gtgagctcag cctccaccaa gggcccaagc gtcttccccc tggcaccctc ctccaagagc | 420 |
| acctctggcg gcacagccgc cctgggctgc ctggtcaagg actacttccc cgaacccgtg | 480 |
| accgtgagct ggaactcagg cgccctgacc agcggcgtgc acaccttccc cgctgtcctg | 540 |
| cagtcctcag gactctactc cctcagcagc gtggtgaccg tgcccctccag cagcttgggc | 600 |
| acccagacct acatctgcaa cgtgaatcac aagcccagca caccaaggt ggacaagaga | 660 |
| gttgagccca atcttgtga caaaactcac acatgcccac cctgcccagc acctgaactc | 720 |
| ctggggggac cctcagtctt cctcttcccc ccaaaaccca aggacaccct catgatctcc | 780 |
| cggacccctg aggtcacatg cgtggtggtg gacgtgagcc acgaagaccc tgaggtcaag | 840 |
| ttcaactggt acgtggacgg cgtggaggtg cataatgcca agacaaagcc ccgggaggag | 900 |
| cagtacaaca gcacgtaccg ggtggtcagc gtcctcaccg tcctgcacca ggactggctg | 960 |
| aatggcaagg agtacaagtg caaggtctcc aacaaagccc tcccagcccc catcgagaaa | 1020 |
| accatctcca aagccaaagg ccagcccggg gaaccacagg tgtacaccct gcccccatcc | 1080 |
| cgggaggaga tgaccaagaa ccaggtcagc ctgacctgcc tggtcaaagg cttctatccc | 1140 |
| agcgacatcg ccgtggagtg ggagagcaat ggccagcccg agaacaacta caagaccacc | 1200 |
| cctcccgtgc tggactccga cggctccttc ttcctctaca gcaagctcac cgtggacaag | 1260 |
| agcaggtggc agcagggcaa cgtcttctca tgctccgtga tgcatgaggc tctgcacaac | 1320 |
| cactacaccc agaagagcct ctccctgtct ccgggcaaa | 1359 |

<210> SEQ ID NO 9
<211> LENGTH: 648

```
<212> TYPE: DNA
<213> ORGANISM: Human

<400> SEQUENCE: 9
cagtctgtgc tgactcagcc accctcagcg tctgggaccc ccgggcagag ggtcaccatc    60
tcctgcactg ggagcagctc caacatcggg gcaggttatg atgtacactg gtatcagcag   120
ctcccaggaa cggcccccaa actcctcatc tatggtaaca gcaatcggcc ctcaggggtc   180
cctgaccgat tctctggctc caagtctggc acctcagcct ccctggccat cagtgggctc   240
cggtccgagg atgaggctga ttattactgc cagtcctatg acagaagcct gaattgggtg   300
ttcggcggag gaaccaagct gacggtccta ggtcagccta aggctgcccc tagcgtgacc   360
ctgttccctc cttccagcga ggagcttcaa gctaacaagg ccaccctggt gtgtcttatc   420
tctgacttct accctggcgc tgtgaccgtg gcctggaagg ctgacagctc ccctgtgaag   480
gccggagtgg agaccaccac acctagcaag cagtctaaca caagtacgc tgccagctcc    540
tacctgagcc ttaccctga gcagtggaag tctcacagaa gctactcctg tcaagtgacc   600
cacgagggca gcaccgtgga aagaccgtg gctcctaccg agtgttcc                648

<210> SEQ ID NO 10
<211> LENGTH: 24
<212> TYPE: DNA
<213> ORGANISM: Artificial Sequence
<220> FEATURE:
<223> OTHER INFORMATION: Primer A

<400> SEQUENCE: 10
gaaacagcta tgaaatacct attg                                           24

<210> SEQ ID NO 11
<211> LENGTH: 19
<212> TYPE: DNA
<213> ORGANISM: Artificial Sequence
<220> FEATURE:
<223> OTHER INFORMATION: Primer B

<400> SEQUENCE: 11
gcctgagcag tggaagtcc                                                 19

<210> SEQ ID NO 12
<211> LENGTH: 24
<212> TYPE: DNA
<213> ORGANISM: Artificial Sequence
<220> FEATURE:
<223> OTHER INFORMATION: Primer C

<400> SEQUENCE: 12
taggtatttc attatgactg tctc                                           24

<210> SEQ ID NO 13
<211> LENGTH: 23
<212> TYPE: DNA
<213> ORGANISM: Artificial Sequence
<220> FEATURE:
<223> OTHER INFORMATION: Primer D

<400> SEQUENCE: 13
cccagtcacg acgttgtaaa acg                                            23

<210> SEQ ID NO 14
<211> LENGTH: 351
<212> TYPE: DNA
```

<213> ORGANISM: Rat

<400> SEQUENCE: 14

```
gaggtgcagc tggtggagtc tgggggaggc ttagtgcagc tggaaggtc caagaaactc      60
tcctgttcag cctcaggatt cacttcagt aactattaca tggcctgggt ccgccaggct     120
ccaacgcagg gtctggagtg ggtcgcatcc attggtactg ttggtggtaa cacttactat    180
cgagactccg tgaagggccg attcactatc tccagagatg atgcaaaaag caccctatac    240
ctgcaaatgg acagtctgag gtctgaggac acggccactt attactgtgc aagagaggat    300
tacggagggt ttccccactg gggccaagga gtcatggtca cagtctcctc a             351
```

<210> SEQ ID NO 15
<211> LENGTH: 117
<212> TYPE: PRT
<213> ORGANISM: Rat

<400> SEQUENCE: 15

Glu Val Gln Leu Val Glu Ser Gly Gly Gly Leu Val Gln Pro Gly Arg
1               5                   10                  15

Ser Lys Lys Leu Ser Cys Ser Ala Ser Gly Phe Thr Phe Ser Asn Tyr
            20                  25                  30

Tyr Met Ala Trp Val Arg Gln Ala Pro Thr Gln Gly Leu Glu Trp Val
        35                  40                  45

Ala Ser Ile Gly Thr Val Gly Gly Asn Thr Tyr Tyr Arg Asp Ser Val
    50                  55                  60

Lys Gly Arg Phe Thr Ile Ser Arg Asp Asp Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Glu Asp Tyr Gly Gly Phe Pro His Trp Gly Gln Gly Val Met
            100                 105                 110

Val Thr Val Ser Ser
        115

<210> SEQ ID NO 16
<211> LENGTH: 327
<212> TYPE: DNA
<213> ORGANISM: Rat

<400> SEQUENCE: 16

```
aatattgtga tgactcagtc tcccacatcc atgttcatat cagtcggaga cagggtcacc      60
atgaactgta aggccagtca gaatgtggga actaatgtag actggtacca gcagaaaaca    120
gggcagtctc ctaaactgct tatctatggg gcgtccaacc gctacactgg agtccctgat    180
cgcttcacag gcagtggatc tggaacagat ttcactctca ccatcagcaa catgcaggct    240
gaagacctgg ctgtttatga ctgtctacag tataagtaca tccatacac gtttggaact    300
gggaccaagc tggaactgaa ccgggct                                        327
```

<210> SEQ ID NO 17
<211> LENGTH: 109
<212> TYPE: PRT
<213> ORGANISM: Rat

<400> SEQUENCE: 17

Asn Ile Val Met Thr Gln Ser Pro Thr Ser Met Phe Ile Ser Val Gly
1               5                   10                  15

Asp Arg Val Thr Met Asn Cys Lys Ala Ser Gln Asn Val Gly Thr Asn
                20                  25                  30

Val Asp Trp Tyr Gln Gln Lys Thr Gly Gln Ser Pro Lys Leu Leu Ile
            35                  40                  45

Tyr Gly Ala Ser Asn Arg Tyr Thr Gly Val Pro Asp Arg Phe Thr Gly
 50                  55                  60

Ser Gly Ser Gly Thr Asp Phe Thr Leu Thr Ile Ser Asn Met Gln Ala
65                  70                  75                  80

Glu Asp Leu Ala Val Tyr Asp Cys Leu Gln Tyr Lys Tyr Asn Pro Tyr
                85                  90                  95

Thr Phe Gly Thr Gly Thr Lys Leu Glu Leu Asn Arg Ala
                100                 105

<210> SEQ ID NO 18
<211> LENGTH: 360
<212> TYPE: DNA
<213> ORGANISM: Rat

<400> SEQUENCE: 18
caggtgcagc tgagggagtc aggacctggt ctggtgcagc cctcacagac cctgtccctc        60
acctgcactg tctctgggtt ctcactaacc agctttcatg taagctgggt tcgccagcct       120
ccagagaagg gtctggagtg gattgcaaca atttcaagtg gtggaggtac atattataat       180
tcagctctca atcccgact gagcatcagc agggacacct ccaagagcca gttttctta        240 aagatgagca ctctgcaaac tgaagacaca gccatgtact tctgtgcccg gatttcgggc       300
tggggccatt actatgttat ggatgtctgg ggtcaaggag cttcagtcac tgtctcctca       360

<210> SEQ ID NO 19
<211> LENGTH: 120
<212> TYPE: PRT
<213> ORGANISM: Rat

<400> SEQUENCE: 19

Gln Val Gln Leu Arg Glu Ser Gly Pro Gly Leu Val Gln Pro Ser Gln
1               5                   10                  15

Thr Leu Ser Leu Thr Cys Thr Val Ser Gly Phe Ser Leu Thr Ser Phe
                20                  25                  30

His Val Ser Trp Val Arg Gln Pro Pro Glu Lys Gly Leu Glu Trp Ile
            35                  40                  45

Ala Thr Ile Ser Ser Gly Gly Gly Thr Tyr Tyr Asn Ser Ala Leu Lys
 50                  55                  60

Ser Arg Leu Ser Ile Ser Arg Asp Thr Ser Lys Ser Gln Val Phe Leu
65                  70                  75                  80

Lys Met Ser Thr Leu Gln Thr Glu Asp Thr Ala Met Tyr Phe Cys Ala
                85                  90                  95

Arg Ile Ser Gly Trp Gly His Tyr Tyr Val Met Asp Val Trp Gly Gln
                100                 105                 110

Gly Ala Ser Val Thr Val Ser Ser
            115                 120

<210> SEQ ID NO 20
<211> LENGTH: 327
<212> TYPE: DNA
<213> ORGANISM: Rat

<400> SEQUENCE: 20
gacatccaga tgacacagtc tccagcttcc ctgtctggat ctctgggaga aactgtcacc        60

```
atccaatgtc aagcaagtga ggacatttac agtggtttag cgtggtatca gcagaagcca    120
gggaaatctc ctcagctcct gatctatggt gcaggtagct acaagacgg cgtcccatca     180 cgattcagtg cggtggatc tggcacacat tattctctca agatcagcag catgcaaact     240
gaagatgaag gggtttattt ctgtcaacag ggtttaaagt ttccgctcac gttcggttct    300
gggaccaagc tggagatcaa acgggct                                        327
```

<210> SEQ ID NO 21
<211> LENGTH: 109
<212> TYPE: PRT
<213> ORGANISM: Rat

<400> SEQUENCE: 21

```
Asp Ile Gln Met Thr Gln Ser Pro Ala Ser Leu Ser Gly Ser Leu Gly
1               5                   10                  15

Glu Thr Val Thr Ile Gln Cys Gln Ala Ser Glu Asp Ile Tyr Ser Gly
            20                  25                  30

Leu Ala Trp Tyr Gln Gln Lys Pro Gly Lys Ser Pro Gln Leu Leu Ile
        35                  40                  45

Tyr Gly Ala Gly Ser Leu Gln Asp Gly Val Pro Ser Arg Phe Ser Gly
    50                  55                  60

Gly Ser Gly Thr His Tyr Ser Leu Lys Ile Ser Ser Met Gln Thr
65                  70                  75                  80

Glu Asp Glu Gly Val Tyr Phe Cys Gln Gln Gly Leu Lys Phe Pro Leu
                85                  90                  95

Thr Phe Gly Ser Gly Thr Lys Leu Glu Ile Lys Arg Ala
            100                 105
```

<210> SEQ ID NO 22
<211> LENGTH: 449
<212> TYPE: DNA
<213> ORGANISM: Human

<400> SEQUENCE: 22

```
gcctccggac tctagagcca ccatggtgct gcagacccag gtgttcatct ccctgctgct    60
gtggatctcc ggcgcgtacg gcgatatcgt gatgattaaa cgtacggtgg ccgcccctc    120 cgtgttcatc ttcccccct ccgacgagca gctgaagtcc ggcaccgcct ccgtggtgtg     180
cctgctgaat aacttctacc cagagaggc caaggtgcag tggaaggtgg acaacgccct    240
gcagtccggg aactcccagg agagcgtgac cgagcaggac agcaaggaca gcacctacag    300
cctgagcagc accctgaccc tgagcaaagc cgactacgag aagcacaagg tgtacgcctg    360
cgaggtgacc caccagggcc tgagctcccc cgtcaccaag agcttcaaca gggggagtg    420 ttaggggccc gtttaaacgg gggaggcta                                      449
```

<210> SEQ ID NO 23
<211> LENGTH: 1132
<212> TYPE: DNA
<213> ORGANISM: Human

<400> SEQUENCE: 23

```
gcctccggac tctagagcca ccatgaaaca cctgtggttc ttcctcctgc tggtggcagc    60
tcccagatgg gtgctgagcc aggtgcaatt gtgcaggcgg ttagctcagc ctccaccaag    120
ggcccaagcg tcttccccct ggcaccctcc tccaagagca cctctggcgg cacagccgcc    180
ctgggctgcc tggtcaagga ctacttcccc gaacccgtga ccgtgagctg gaactcaggc    240
```

```
gccctgacca gcggcgtgca caccttcccc gctgtcctgc agtcctcagg actctactcc    300
ctcagcagcg tggtgaccgt gccctccagc agcttgggca cccagaccta catctgcaac    360
gtgaatcaca agcccagcaa caccaaggtg gacaagagag ttgagcccaa atcttgtgac    420
aaaactcaca catgcccacc ctgcccagca cctgaactcc tggggggacc ctcagtcttc    480
ctcttccccc caaaacccaa ggacaccctc atgatctccc ggacccctga ggtcacatgc    540
gtggtggtgg acgtgagcca cgaagaccct gaggtcaagt tcaactggta cgtggacggc    600
gtggaggtgc ataatgccaa gacaaagccc cgggaggagc agtacaacag cacgtaccgg    660
gtggtcagcg tcctcaccgt cctgcaccag gactggctga atggcaagga gtacaagtgc    720
aaggtctcca acaaagccct cccagccccc atcgagaaaa ccatctccaa agccaaaggc    780
cagccccggg aaccacaggt gtacaccctg cccccatccc gggaggagat gaccaagaac    840
caggtcagcc tgacctgcct ggtcaaaggc ttctatccca gcgacatcgc cgtggagtgg    900
gagagcaatg gccagcccga gaacaactac aagaccaccc ctcccgtgct ggactccgac    960
ggctccttct tcctctacag caagctcacc gtggacaaga gcaggtggca gcagggcaac   1020
gtcttctcat gctccgtgat gcatgaggct ctgcacaacc actacaccca gaagagcctc   1080
tccctgtctc ccggcaaatg agatatcggg cccgtttaaa cggggggaggc ta          1132
```

<210> SEQ ID NO 24
<211> LENGTH: 1398
<212> TYPE: DNA
<213> ORGANISM: Artificial Sequence
<220> FEATURE:
<223> OTHER INFORMATION: Chimeric Antibody

<400> SEQUENCE: 24

```
atgaaacacc tgtggttctt cctcctgctg gtggcagctc ccagatgggt gctgagcgag     60
gtgcagctgg tggagtctgg gggaggctta gtgcagcctg aaggtccaa gaaactctcc    120 tgttcagcct caggattcac tttcagtaac tattacatgg cctgggtccg ccaggctcca    180
acgcagggtc tggagtgggt cgcatccatt ggtactgttg gtggtaacac ttactatcga    240
gactccgtga agggccgatt cactatctcc agagatgatg caaaaagcac cctatacctg    300
caaatggaca gtctgaggtc tgaggacacg gccacttatt actgtgcaag agaggattac    360
ggagggtttc cccactgggg ccaaggagtc atggtcacag tcagctcagc ctccaccaag    420
ggcccaagcg tcttcccccct ggcaccctcc tccaagagca cctctggcgg cacagccgcc    480
ctgggctgcc tggtcaagga ctacttcccc gaacccgtga ccgtgagctg gaactcaggc    540
gccctgacca gcggcgtgca caccttcccc gctgtcctgc agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc ctgcccagca cctgaactcc tggggggacc ctcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccc cgggaggagc agtacaacag cacgtaccgg    960
gtggtcagcg tcctcaccgt cctgcaccag gactggctga atggcaagga gtacaagtgc   1020
aaggtctcca acaaagccct cccagccccc atcgagaaaa ccatctccaa agccaaaggc   1080
cagccccggg aaccacaggt gtacaccctg cccccatccc gggaggagat gaccaagaac   1140
```

-continued

```
caggtcagcc tgacctgcct ggtcaaaggc ttctatccca gcgacatcgc cgtggagtgg      1200
gagagcaatg ccagcccga gaacaactac aagaccaccc ctcccgtgct ggactccgac      1260
ggctccttct tcctctacag caagctcacc gtggacaaga gcaggtggca gcagggcaac      1320
gtcttctcat gctccgtgat gcatgaggct ctgcacaacc actacaccca gaagagcctc      1380
tccctgtctc ccggcaaa                                                   1398

<210> SEQ ID NO 25
<211> LENGTH: 466
<212> TYPE: PRT
<213> ORGANISM: Artificial Sequence
<220> FEATURE:
<223> OTHER INFORMATION: Chimeric Antibody

<400> SEQUENCE: 25
```

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Lys Lys Leu Ser Cys Ser Ala Ser Gly Phe Thr Phe
        35                  40                  45

Ser Asn Tyr Tyr Met Ala Trp Val Arg Gln Ala Pro Thr Gln Gly Leu
    50                  55                  60

Glu Trp Val Ala Ser Ile Gly Thr Val Gly Gly Asn Thr Tyr Tyr Arg
65                  70                  75                  80

Asp Ser Val Lys Gly Arg Phe Thr Ile Ser Arg Asp Asp Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Arg Glu Asp Tyr Gly Gly Phe Pro His Trp Gly Gln
        115                 120                 125

Gly Val Met Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
        340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 26
<211> LENGTH: 702
<212> TYPE: DNA
<213> ORGANISM: Artificial Sequence
<220> FEATURE:
<223> OTHER INFORMATION: Chimeric Antibody

<400> SEQUENCE: 26

```
atggtgctgc agacccaggt gttcatctcc ctgctgctgt ggatctccgg cgcgtacggc      60
aatattgtga tgactcagtc tcccacatcc atgttcatat cagtcggaga cagggtcacc     120
atgaactgta aggccagtca gaatgtggga actaatgtag actggtacca gcagaaaaca     180
gggcagtctc ctaaactgct tatctatggg gcgtccaacc gctacactgg agtccctgat     240
cgcttcacag gcagtggatc tggaacagat ttcactctca ccatcagcaa catgcaggct     300
gaagacctgg ctgtttatga ctgtctacag tataagtaca atccatacac gtttggaact     360
gggaccaagc tggaactgaa ccgggctgtg gccgccccct ccgtgttcat cttccccccc     420
tccgacgagc agctgaagtc cggcaccgcc tccgtggtgt gcctgctgaa taacttctac     480
cccagagagg ccaaggtgca gtggaaggtg acaacgccc tgcagtccgg aactcccag      540 gagagcgtga ccgagcagga cagcaaggac agcacctaca gcctgagcag caccctgacc     600
ctgagcaaag ccgactacga aagcacaag gtgtacgcct gcgaggtgac ccaccagggc     660
ctgagctccc ccgtcaccaa gagcttcaac agggggagt gt                        702
```

<210> SEQ ID NO 27
<211> LENGTH: 234
<212> TYPE: PRT
<213> ORGANISM: Artificial Sequence
<220> FEATURE:
<223> OTHER INFORMATION: Chimeric Antibody

<400> SEQUENCE: 27

Met Val Leu Gln Thr Gln Val Phe Ile Ser Leu Leu Leu Trp Ile Ser
1               5                   10                  15

Gly Ala Tyr Gly Asn Ile Val Met Thr Gln Ser Pro Thr Ser Met Phe

```
                20                  25                  30
Ile Ser Val Gly Asp Arg Val Thr Met Asn Cys Lys Ala Ser Gln Asn
             35                  40                  45
Val Gly Thr Asn Val Asp Trp Tyr Gln Gln Lys Thr Gly Gln Ser Pro
 50                  55                  60
Lys Leu Leu Ile Tyr Gly Ala Ser Asn Arg Tyr Thr Gly Val Pro Asp
 65                  70                  75                  80
Arg Phe Thr Gly Ser Gly Ser Gly Thr Asp Phe Thr Leu Thr Ile Ser
                 85                  90                  95
Asn Met Gln Ala Glu Asp Leu Ala Val Tyr Asp Cys Leu Gln Tyr Lys
             100                 105                 110
Tyr Asn Pro Tyr Thr Phe Gly Thr Gly Thr Lys Leu Glu Leu Asn Arg
         115                 120                 125
Ala Val Ala Ala Pro Ser Val Phe Ile Phe Pro Pro Ser Asp Glu Gln
     130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                 165                 170                 175
Gly Asn Ser Gln Glu Ser Val Thr Glu Gln Asp Ser Lys Asp Ser Thr
             180                 185                 190
Tyr Ser Leu Ser Ser Thr Leu Thr Leu Ser Lys Ala Asp Tyr Glu Lys
         195                 200                 205
His Lys Val Tyr Ala Cys Glu Val Thr His Gln Gly Leu Ser Ser Pro
     210                 215                 220
Val Thr Lys Ser Phe Asn Arg Gly Glu Cys
225                 230

<210> SEQ ID NO 28
<211> LENGTH: 1407
<212> TYPE: DNA
<213> ORGANISM: Artificial Sequence
<220> FEATURE:
<223> OTHER INFORMATION: Chimeric Antibody

<400> SEQUENCE: 28
atgaaacacc tgtggttctt cctcctgctg gtggcagctc ccagatgggt gctgagccag      60
gtgcagctga gggagtcagg acctggtctg gtgcagccct cacagaccct gtccctcacc     120
tgcactgtct ctgggttctc actaaccagc tttcatgtaa gctgggttcg ccagcctcca     180
gagaagggtc tggagtggat tgcaacaatt tcaagtggtg aggtacata ttataattca      240
gctctcaaat cccgactgag catcagcagg gacacctcca agagccaagt tttcttaaag     300
atgagcactc tgcaaactga agacacagcc atgtacttct gtgcccggat tcgggctgg      360
ggccattact atgttatgga tgtctggggt caaggagctt cagtcactgt cagctcagcc     420
tccaccaagg gcccaagcgt cttccccctg gcacctcct ccaagagcac ctctggcggc     480
acagccgccc tgggctgcct ggtcaaggac tacttccccg aacccgtgac cgtgagctgg     540
aactcaggcg ccctgaccag cggcgtgcac accttcccg ctgtcctgca gtcctcagga     600
ctctactccc tcagcagcgt ggtgaccgtg ccctccagca gcttgggcac ccagacctac     660
atctgcaacg tgaatcacaa gcccagcaac accaaggtgg acaagagagt tgagcccaaa     720
tcttgtgaca aaactcacac atgcccaccg tgcccagcac ctgaactcct ggggggaccc     780
tcagtcttcc tcttcccccc aaaacccaag gacaccctca tgatctcccg gacccctgag     840
```

```
gtcacatgcg tggtggtgga cgtgagccac gaagaccctg aggtcaagtt caactggtac    900
gtggacggcg tggaggtgca taatgccaag acaaagcccc gggaggagca gtacaacagc    960
acgtaccggg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaaggcc agccccggga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg ccagcccgag aacaactaca agaccacccc tcccgtgctg   1260
gactccgacg gctccttctt cctctacagc aagctcaccg tggacaagag caggtggcag   1320
cagggcaacg tcttctcatg ctccgtgatg catgaggctc tgcacaacca ctacacccag   1380
aagagcctct ccctgtctcc cggcaaa                                        1407
```

<210> SEQ ID NO 29
<211> LENGTH: 469
<212> TYPE: PRT
<213> ORGANISM: Artificial Sequence
<220> FEATURE:
<223> OTHER INFORMATION: Chimeric Antibody

<400> SEQUENCE: 29

```
Met Lys His Leu Trp Phe Phe Leu Leu Leu Val Ala Ala Pro Arg Trp
1               5                   10                  15

Val Leu Ser Gln Val Gln Leu Arg Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Ser Phe His Val Ser Trp Val Arg Gln Pro Pro Glu Lys Gly Leu
    50                  55                  60

Glu Trp Ile Ala Thr Ile Ser Ser Gly Gly Gly Thr Tyr Tyr Asn Ser
65                  70                  75                  80

Ala Leu Lys Ser Arg Leu Ser Ile Ser Arg Asp Thr Ser Lys Ser Gln
                85                  90                  95

Val Phe Leu Lys Met Ser Thr Leu Gln Thr Glu Asp Thr Ala Met Tyr
            100                 105                 110

Phe Cys Ala Arg Ile Ser Gly Trp Gly His Tyr Tyr Val Met Asp Val
        115                 120                 125

Trp Gly Gln Gly Ala Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
```

```
                260                 265                 270
Leu Met Ile Ser Arg Thr Pro Glu Val Thr Cys Val Val Asp Val
            275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 30
<211> LENGTH: 702
<212> TYPE: DNA
<213> ORGANISM: Artificial Sequence
<220> FEATURE:
<223> OTHER INFORMATION: Chimeric Antibody

<400> SEQUENCE: 30
atggtgctgc agacccaggt gttcatctcc ctgctgctgt ggatctccgg cgcgtacggc      60
gacatccaga tgacacagtc tccagcttcc ctgtctggat ctctgggaga aactgtcacc     120
atccaatgtc aagcaagtga ggacatttac agtggtttag cgtggtatca gcagaagcca     180
gggaaatctc ctcagctcct gatctatggt gcaggtagct acaagacggg cgtcccatca     240
cgattcagtg gcggtggatc tggcacacat tattctctca agatcagcag catgcaaact     300
gaagatgaag ggttttattt ctgtcaacag ggtttaaagt ttccgctcac gttcggttct     360
gggaccaagc tggagatcaa acgggctgtg gccgccccct ccgtgttcat cttcccccca     420
tccgacgagc agctgaagtc cggcaccgcc tccgtggtgt gcctgctgaa taacttctac     480
cccagagagg ccaaggtgca gtggaaggtg gacaacgccc tgcagtccgg aaactcccag     540
gagagcgtga ccgagcagga cagcaaggac agcacctaca gcctgagcag caccctgacc     600
ctgagcaaag ccgactacga aagcacaag gtgtacgcct gcgaggtgac ccaccagggc     660
ctgagctccc ccgtcaccaa gagcttcaac agggggagt gt                         702

<210> SEQ ID NO 31
<211> LENGTH: 234
<212> TYPE: PRT
```

<213> ORGANISM: Artificial Sequence
<220> FEATURE:
<223> OTHER INFORMATION: Chimeric Antibody

<400> SEQUENCE: 31

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ala Ser Leu Ser
                20                  25                  30

Gly Ser Leu Gly Glu Thr Val Thr Ile Gln Cys Gln Ala Ser Glu Asp
            35                  40                  45

Ile Tyr Ser Gly Leu Ala Trp Tyr Gln Gln Lys Pro Gly Lys Ser Pro
        50                  55                  60

Gln Leu Leu Ile Tyr Gly Ala Gly Ser Leu Gln Asp Gly Val Pro Ser
65                  70                  75                  80

Arg Phe Ser Gly Gly Ser Gly Thr His Tyr Ser Leu Lys Ile Ser
                85                  90                  95

Ser Met Gln Thr Glu Asp Glu Gly Val Tyr Phe Cys Gln Gln Gly Leu
                100                 105                 110

Lys Phe Pro Leu Thr Phe Gly Ser Gly Thr Lys Leu Glu Ile Lys Arg
            115                 120                 125

Ala Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 32
<211> LENGTH: 1398
<212> TYPE: DNA
<213> ORGANISM: Artificial Sequence
<220> FEATURE:
<223> OTHER INFORMATION: Humanized Antibody

<400> SEQUENCE: 32

```
atgaagcacc tgtggttctt tctgctgctg gtggccgctc ccagatgggt gctgtctgaa      60
gtgcagctgg tggaatccgg cggaggcctg gtgcagcctg gcggatctct gagactgtct     120
tgtgccgcct ccggcttcac cttctccaac tactacatgg cctgggtgcg acaggccccg     180
ggcaagggac tggaatgggt gtcctctatc ggcaccgtgg gcggcaacac ctactacgcc     240
gattctgtga agggccggtt caccatctcc cgggacgact ccaagaacac cctgtacctg     300
cagatgaact ccctgcgggc cgaggacacc gccgtgtact actgtgccag agaggactac     360
ggcggcttcc ctcattgggg ccagggcaca ctcgtgaccg tgtcctctgc ttccaccaag     420
ggcccctccg tgtttcctct ggccccttcc agcaagtcca cctctggcgg aacagccgct     480
ctgggctgcc tcgtgaagga ctacttcccc gagcccgtga cagtgtcttg gaactctggc     540
```

```
gccctgacct ccggcgtgca caccttttcca gctgtgctgc agtcctccgg cctgtactcc      600
ctgtcctccg tcgtgactgt gccctccagc tctctgggca cccagaccta catctgcaac      660
gtgaaccaca agccctccaa caccaaggtg acaagcggg tggaacccaa gtcctgcgac      720
aagacccaca cctgtccccc ttgtcctgcc cctgaactgc tgggcggacc ttccgtgttc      780
ctgttccccc caaagcctaa ggacaccctg atgatctccc ggaccccccga agtgacctgc      840
gtggtggtgg atgtgtccca cgaggaccct gaagtgaagt tcaattggta cgtggacggc      900
gtggaagtgc acaacgccaa gaccaagcct agagaggaac agtacaactc cacctaccgg      960
gtggtgtccg tgctgaccgt gctgcatcag gactggctga acggcaaaga gtacaagtgc     1020
aaggtgtcca acaaggccct gcctgccccc atcgaaaaga ccatctccaa ggccaagggc     1080
cagccccggg aacccaggt gtacacactg ccccctagcc gggaagagat gaccaagaac     1140
caggtgtccc tgacctgtct cgtgaaaggc ttctacccct ccgatatcgc cgtggaatgg     1200
gagagcaacg gccagcccga gaacaactac aagaccaccc cccctgtgct ggactccgac     1260
ggctcattct tcctgtacag caagctgaca gtggacaagt cccggtggca gcagggcaac     1320
gtgttctcct gctccgtgat gcacgaggcc ctgcacaacc actacaccca gaagtccctg     1380
tccctgagcc ccggcaaa                                                   1398
```

<210> SEQ ID NO 33
<211> LENGTH: 466
<212> TYPE: PRT
<213> ORGANISM: Artificial Sequence
<220> FEATURE:
<223> OTHER INFORMATION: Humanized Antibody

<400> SEQUENCE: 33

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Tyr Met Ala Trp Val Arg Gln Ala Pro Gly Lys Gly Leu
    50                  55                  60

Glu Trp Val Ser Ser Ile Gly Thr Val Gly Gly Asn Thr Tyr Tyr Ala
65                  70                  75                  80

Asp Ser Val Lys Gly Arg Phe Thr Ile Ser Arg Asp Asp Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Asp Tyr Gly Gly Phe Pro His Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205
```

```
Ser Ser Ser Leu Gly Thr Gln Thr Tyr Ile Cys Asn Val Asn His Lys
    210                 215                 220
Pro Ser Asn Thr Lys Val Asp Lys Arg Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465
```

<210> SEQ ID NO 34
<211> LENGTH: 1398
<212> TYPE: DNA
<213> ORGANISM: Artificial Sequence
<220> FEATURE:
<223> OTHER INFORMATION: Humanized Antibody

<400> SEQUENCE: 34

```
atgaagcacc tgtggttctt tctgctgctg gtggccgctc ccagatgggt gctgtctgaa    60
gtgcagctgg tggaatccgg cggaggcctg gtgcagcctg gcggatctct gagactgtct   120
tgtgccgcct ccggcttcac cttctccaac tactacatgg cctgggtgcg acaggccct   180
ggcaagggac tggaatgggt ggcctctatc ggcaccgtgg gcggcaacac ctactaccgg   240
gattctgtga aggccggtt caccatctcc cgggacgact ccaagtccac cctgtacctg   300
cagatgaact ccctgcgggc cgaggacacc gccgtgtact actgtgccag agaggactac   360
ggcggcttcc tcattgggg ccagggcaca ctcgtgaccg tgtcctctgc ttccaccaag   420
ggcccctccg tgtttcctct ggccccttcc agcaagtcta cctccggcgg aacagccgct   480
ctgggctgcc tcgtgaagga ctacttcccc gagcccgtga cagtgtcttg gaactctggc   540
```

```
gccctgacca gcggcgtgca cacctttcca gctgtgctgc agtcctccgg cctgtactcc    600
ctgtcctccg tcgtgactgt gccctccagc tctctgggca cccagaccta catctgcaac    660
gtgaaccaca agccctccaa caccaaggtg gacaagcggg tggaacccaa gtcctgcgac    720
aagacccaca cctgtccccc ttgtcctgcc cctgaactgc tgggcggacc ttccgtgttc    780
ctgttccccc caaagcccaa ggacaccctg atgatctccc ggacccccga agtgacctgc    840
gtggtggtgg atgtgtccca cgaggaccct gaagtgaagt tcaattggta cgtggacggc    900
gtggaagtgc acaacgccaa gaccaagcct agagaggaac agtacaactc cacctaccgg    960
gtggtgtccg tgctgaccgt gctgcatcag gactggctga acggcaaaga gtacaagtgc   1020
aaggtgtcca acaaggccct gcctgccccc atcgaaaaga ccatctccaa ggccaagggc   1080
cagccccggg aacccaggt gtacacactg cccctagcc gggaagagat gaccaagaac    1140
caggtgtccc tgacctgtct cgtgaaaggc ttctacccct ccgatatcgc cgtggaatgg   1200
gagtccaacg gccagcctga gaacaactac aagaccaccc ccctgtgct ggactccgac   1260
ggctcattct tcctgtacag caagctgaca gtggacaagt cccggtggca gcagggcaac   1320
gtgttctcct gctccgtgat gcacgaggcc ctgcacaacc actacaccca gaagtccctg   1380
tccctgagcc ccggcaaa                                                 1398
```

<210> SEQ ID NO 35
<211> LENGTH: 466
<212> TYPE: PRT
<213> ORGANISM: Artificial Sequence
<220> FEATURE:
<223> OTHER INFORMATION: Humanized Antibody

<400> SEQUENCE: 35

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Tyr Met Ala Trp Val Arg Gln Ala Pro Gly Lys Gly Leu
    50                  55                  60

Glu Trp Val Ala Ser Ile Gly Thr Val Gly Gly Asn Thr Tyr Tyr Arg
65                  70                  75                  80

Asp Ser Val Lys Gly Arg Phe Thr Ile Ser Arg Asp Asp Ser Lys Ser
                85                  90                  95

Thr Leu Tyr Leu Gln Met Asn Ser Leu Arg Ala Glu Asp Thr Ala Val
            100                 105                 110

Tyr Tyr Cys Ala Arg Glu Asp Tyr Gly Gly Phe Pro His Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205
```

```
Ser Ser Ser Leu Gly Thr Gln Thr Tyr Ile Cys Asn Val Asn His Lys
    210                 215                 220
Pro Ser Asn Thr Lys Val Asp Lys Arg Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
450                 455                 460
Gly Lys
465
```

<210> SEQ ID NO 36
<211> LENGTH: 702
<212> TYPE: DNA
<213> ORGANISM: Artificial Sequence
<220> FEATURE:
<223> OTHER INFORMATION: Humanized Antibody

<400> SEQUENCE: 36

```
atggtgctgc agacccaggt gttcatctcc ctgctgctgt ggatctccgg cgcctacggc      60
aacatcgtga tgacccagtc ccccgactcc ctggctgtgt ctctgggcga gagagccacc     120
atcaactgca aggcctccca gaacgtgggc accaacgtgg actggtatca gcagaagccc     180
ggccagtccc ctaagctgct gatctacggc gccagcaacc ggtacaccgg cgtgcccgat     240
agattctccg gctctggctc tggcaccgac tttaccctga caatcagctc tctgcaggcc     300
gaggacgtgg ccgtgtacga ctgcctgcag tacaagtaca cccctacac cttcggccag     360
ggcacaaagg tggaaatcaa gcggaccgtg gccgctccct ccgtgtttat cttcccaccc     420
tccgacgagc agctgaagtc cggcacagct tccgtcgtgt gcctgctgaa caacttctac     480
ccccgcgagg ccaaggtgca gtggaaggtg gacaacgccc tgcagtccgg caactcccag     540
```

```
gaatccgtga ccgagcagga ctccaaggac agcacctact ccctgtcctc cacccctgacc    600 ctgtccaagg ccgactacga gaagcacaag gtgtacgcct gcgaagtgac ccaccagggc    660
ctgtctagcc ccgtgaccaa gtctttcaac cggggcgagt gc                       702
```

<210> SEQ ID NO 37
<211> LENGTH: 234
<212> TYPE: PRT
<213> ORGANISM: Artificial Sequence
<220> FEATURE:
<223> OTHER INFORMATION: Humanized Antibody

<400> SEQUENCE: 37

```
Met Val Leu Gln Thr Gln Val Phe Ile Ser Leu Leu Trp Ile Ser
1               5                   10                  15

Gly Ala Tyr Gly Asn Ile Val Met Thr Gln Ser Pro Asp Ser Leu Ala
            20                  25                  30

Val Ser Leu Gly Glu Arg Ala Thr Ile Asn Cys Lys Ala Ser Gln Asn
        35                  40                  45

Val Gly Thr Asn Val Asp Trp Tyr Gln Gln Lys Pro Gly Gln Ser Pro
    50                  55                  60

Lys Leu Leu Ile Tyr Gly Ala Ser Asn Arg Tyr Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Asp Cys Leu Gln Tyr Lys
            100                 105                 110

Tyr Asn Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 38
<211> LENGTH: 702
<212> TYPE: DNA
<213> ORGANISM: Artificial Sequence
<220> FEATURE:
<223> OTHER INFORMATION: Humanized Antibody

<400> SEQUENCE: 38

```
atggtgctgc agacccaggt gttcatctcc ctgctgctgt ggatctccgg cgcctacggc    60
aacatcgtga tgacccagtc cccctccagc ctgtctgctt ccgtgggcga cagagtgacc    120
atcaactgca aggcctccca gaacgtgggc accaacgtgg actggtatca gcagaagccc    180
ggcaagtccc ccaagctgct gatctacggc gccagcaaca gatacaccgg cgtgcccgac    240
```

-continued

```
agattctccg gctctggctc tggcaccgac tttaccctga ccatcagctc cctgcagccc    300
gaggacttcg ccacctacga ctgcctgcag tacaagtaca accccctcacac cttcggccag    360 ggcacaaagg tggaaatcaa gcggaccgtg gccgctccct ccgtgtttat cttcccaccc    420
tccgacgagc agctgaagtc cggcacagct tctgtcgtgt gcctgctgaa caacttctac    480
ccccgcgagg ccaaggtgca gtggaaggtg gacaacgccc tgcagtccgg caactcccag    540
gaatccgtga ccgagcagga ctccaaggac agcacctact ccctgtcctc cacccctgacc    600 ctgtccaagg ccgactacga aagcacaag gtgtacgcct gcgaagtgac ccaccagggc    660
ctgtctagcc ccgtgaccaa gtctttcaac cggggcgagt gc                        702
```

<210> SEQ ID NO 39
<211> LENGTH: 234
<212> TYPE: PRT
<213> ORGANISM: Artificial Sequence
<220> FEATURE:
<223> OTHER INFORMATION: Humanized Antibody

<400> SEQUENCE: 39

```
Met Val Leu Gln Thr Gln Val Phe Ile Ser Leu Leu Trp Ile Ser
1               5                   10                  15

Gly Ala Tyr Gly Asn Ile Val Met Thr Gln Ser Pro Ser Ser Leu Ser
            20                  25                  30

Ala Ser Val Gly Asp Arg Val Thr Ile Asn Cys Lys Ala Ser Gln Asn
        35                  40                  45

Val Gly Thr Asn Val Asp Trp Tyr Gln Gln Lys Pro Gly Lys Ser Pro
    50                  55                  60

Lys Leu Leu Ile Tyr Gly Ala Ser Asn Arg Tyr Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Asp Cys Leu Gln Tyr Lys
            100                 105                 110

Tyr Asn Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 40
<211> LENGTH: 1407
<212> TYPE: DNA
<213> ORGANISM: Artificial Sequence
<220> FEATURE:
<223> OTHER INFORMATION: Humanized Antibody

<400> SEQUENCE: 40

```
atgaagcacc tgtggttctt tctgctgctg gtggccgctc ccagatgggt gctgtctgaa      60
gtgcagctgg tggaatccgg cggaggcctc gtgaagcctt cccagaccct gtctctgacc     120
tgcaccgtgt ccggcttctc cctgacctcc ttccacgtgt catgggtgcg acagcctcca     180
ggcaagggcc tggaatggat cgccaccatc tcctctggcg gcggaaccta ctacaacccc     240
agcctgaagt ccagagtgac catctcccgg gacacctcca gaaccaggt gtccctgaag      300
ctgtcctccg tgaccgccgc tgataccgcc gtgtactact gcgccagaat ctccggctgg     360
ggccactact acgtgatgga cgtgtgggc agggcaccc tcgtgacagt gtcctctgct       420
tccaccaagg gcccctccgt gtttcctctg gccccttcca gcaagtctac ctccggcgga    480
acagccgctc tgggctgcct cgtgaaagac tacttcccg agcccgtgac cgtgtcttgg     540
aactctggcg ctctgaccag cggcgtgcac acctttccag ctgtgctgca gtcctccggc    600
ctgtactccc tgtccagcgt cgtgactgtg ccctccagct ctctgggcac ccagacctac    660
atctgcaacg tgaaccacaa gccctccaac accaaggtgg acaagcgggt ggaacccaag    720
tcctgcgaca gacccacac ctgtcccct tgtcctgccc ctgaactgct gggcggacct       780
tccgtgttcc tgttccccc aaagcccaag gacaccctga tgatctcccg gaccccgaa      840
gtgacctgcg tggtggtgga tgtgtcccac gaggaccctg aagtgaagtt caattggtac    900
gtggacggcg tggaagtgca caacgccaag accaagccta gaggaaca gtacaactcc      960
acctaccggg tggtgtccgt gctgaccgtg ctgcaccagg attggctgaa cggcaaagag   1020
tacaagtgca aggtgtccaa caaggccctg cctgccccca tcgaaaagac catcagcaag   1080
gccaagggcc agccccggga accccaggtg tacacactgc ccctagccg gaagagatg     1140
acaaaaaatc aggtgtcact gacctgtctc gtgaagggct tctacccctc cgatatcgcc   1200
gtggaatggg agtccaacgg ccagcctgag aacaactaca agaccacccc ccctgtgctg   1260
gactccgacg gctcattctt cctgtacagc aagctgacag tggacaagtc ccggtggcag   1320
cagggcaacg tgttctcctg ctccgtgatg cacgaggccc tgcacaacca ctacacccag   1380
aagtccctgt ccctgagccc cggcaaa                                      1407
```

<210> SEQ ID NO 41
<211> LENGTH: 469
<212> TYPE: PRT
<213> ORGANISM: Artificial Sequence
<220> FEATURE:
<223> OTHER INFORMATION: Humanized Antibody

<400> SEQUENCE: 41

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Lys
            20                  25                  30

Pro Ser Gln Thr Leu Ser Leu Thr Cys Thr Val Ser Gly Phe Ser Leu
        35                  40                  45

Thr Ser Phe His Val Ser Trp Val Arg Gln Pro Pro Gly Lys Gly Leu
    50                  55                  60

Glu Trp Ile Ala Thr Ile Ser Ser Gly Gly Gly Thr Tyr Tyr Asn Pro
65                  70                  75                  80

Ser Leu Lys Ser Arg Val Thr Ile Ser Arg Asp Thr Ser Lys Asn Gln
                85                  90                  95

Val Ser Leu Lys Leu Ser Ser Val Thr Ala Ala Asp Thr Ala Val Tyr
```

```
            100                 105                 110
Tyr Cys Ala Arg Ile Ser Gly Trp Gly His Tyr Tyr Val Met Asp Val
            115                 120                 125

Trp Gly Gln Gly Thr Leu Val Thr Val Ser Ser Ala Ser Thr Lys Gly
            130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 42
<211> LENGTH: 702
<212> TYPE: DNA
<213> ORGANISM: Artificial Sequence
<220> FEATURE:
<223> OTHER INFORMATION: Humanized Antibody
```

<400> SEQUENCE: 42

```
atggtgctgc agacccaggt gttcatctcc ctgctgctgt ggatctccgg cgcctacggc      60
gacatccaga tgacccagag cccttccagc ctgtccgctt ccgtgggcga cagagtgacc     120
atcacctgtc aggcctccga ggacatctac tccggcctgg cctggtatca gcagaagccc     180
ggcaagtccc ccaagctgct gatctacggc gctggatctc tgcaggacgg cgtgccctct     240
agattctccg gctctggatc cggcacccac tacaccctga ccatctccag cctgcagccc     300
gaggacttcg ctacctactt ctgtcagcaa ggcctgaagt tccccctgac cttcggccag     360
ggcaccaagg tggaaatcaa gcggaccgtg gccgctccct ccgtgtttat cttcccaccc     420
tccgacgagc agctgaagtc cggcacagct tctgtcgtgt gcctgctgaa caacttctac     480
ccccgcgagg ccaaggtgca gtggaaggtg gacaacgccc tgcagtccgg caactcccag     540
gaatccgtga ccgagcagga ctccaaggac agcacctact ccctgtcctc taccctgacc     600
ctgtccaagg ccgactacga gaagcacaag gtgtacgcct gcgaagtgac ccaccagggc     660
ctgtctagcc ccgtgaccaa gtctttcaac cggggcgagt gc                       702
```

<210> SEQ ID NO 43
<211> LENGTH: 234
<212> TYPE: PRT
<213> ORGANISM: Artificial Sequence
<220> FEATURE:
<223> OTHER INFORMATION: Humanized Antibody

<400> SEQUENCE: 43

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Glu Asp
        35                  40                  45

Ile Tyr Ser Gly Leu Ala Trp Tyr Gln Gln Lys Pro Gly Lys Ser Pro
    50                  55                  60

Lys Leu Leu Ile Tyr Gly Ala Gly Ser Leu Gln Asp Gly Val Pro Ser
65                  70                  75                  80

Arg Phe Ser Gly Ser Gly Ser Gly Thr His Tyr Thr Leu Thr Ile Ser
                85                  90                  95

Ser Leu Gln Pro Glu Asp Phe Ala Thr Tyr Phe Cys Gln Gln Gly Leu
            100                 105                 110

Lys Phe Pro Leu Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
                225                 230
```

```
<210> SEQ ID NO 44
<211> LENGTH: 34
<212> TYPE: DNA
<213> ORGANISM: Artificial Sequence
<220> FEATURE:
<223> OTHER INFORMATION: Primer F

<400> SEQUENCE: 44
cacggcaacc tgctggagcg gctgctgggg gagg                                 34

<210> SEQ ID NO 45
<211> LENGTH: 24
<212> TYPE: DNA
<213> ORGANISM: Artificial Sequence
<220> FEATURE:
<223> OTHER INFORMATION: Primer R

<400> SEQUENCE: 45
caggctgttc ccagacaggt ccag                                            24
```